(12) United States Patent
Cowman et al.

(10) Patent No.: US 10,940,190 B2
(45) Date of Patent: Mar. 9, 2021

(54) MALARIA VACCINE AND METHODS FOR PRODUCING SAME

(71) Applicants: The Walter and Eliza Hall institute of Medical Research, Melbourne (AU); Expres2ion Biotechnologies, Horsholm (DK)

(72) Inventors: Alan Cowman, Parkville (AU); Julie Healer, Parkville (AU); Willem Adriaan De Jongh, Valby (DK); Teit Max Moscote Sogaard, Kokkedal (DK); Thomas Dan Jorgensen, Helsingor (DK); Vladyslav Soroka, Taastrup (DK)

(73) Assignees: The Walter and Eliza Hall Institute of Medical Research, Melbourne (AU); Expres2ion Biotechnologies, Horsholm (DK)

( * ) Notice: Subject to any disclaimer, the term of this patent is extended or adjusted under 35 U.S.C. 154(b) by 0 days.

(21) Appl. No.: 16/488,999

(22) PCT Filed: Feb. 23, 2018

(86) PCT No.: PCT/AU2018/050155
§ 371 (c)(1),
(2) Date: Aug. 27, 2019

(87) PCT Pub. No.: WO2018/152584
PCT Pub. Date: Aug. 30, 2018

(65) Prior Publication Data
US 2020/0030427 A1    Jan. 30, 2020

(30) Foreign Application Priority Data

Feb. 27, 2017 (AU) ................................ 2017900648

(51) Int. Cl.
| | | |
|---|---|---|
| *A61K 39/015* | (2006.01) | |
| *C07K 14/445* | (2006.01) | |
| *C07K 14/705* | (2006.01) | |
| *C07K 16/20* | (2006.01) | |

(52) U.S. Cl.
CPC .......... *A61K 39/015* (2013.01); *C07K 14/445* (2013.01); *C07K 14/705* (2013.01); *C07K 16/205* (2013.01); *C07K 2317/73* (2013.01)

(58) Field of Classification Search
None
See application file for complete search history.

(56) References Cited

U.S. PATENT DOCUMENTS

2015/0366958 A1   12/2015   Chen et al.

FOREIGN PATENT DOCUMENTS

WO    2016016651 A2    2/2016

OTHER PUBLICATIONS

Houghten et al. (Vaccines, 1986, Edited by Fred Brown: Cold Spring Harbor Laboratory) (Year: 1986).*
Bahrami, S. et al., 2007 "Ligand presentation on a synthetic flexible hinge in Moloney murine leukemia virus SU supports entry via a heterologous receptor" Virology 363 pp. 303-309.
Bird, R.E., et al 1988, "Single-Chain Antigen Binding Protein" Science; 242:423-426.
De Jongh, W.A., et al. "Development of a *Drosophila* S2 insect-cell based placental malaria vaccine production process." BMC proceedings, 2013, vol. 7, No. 6, p. P20.
George & Heringa, 2003 "An analysis of protein domain linkers: their classification and role in protein folding" Protein Engineering vol. 15 No. 11 pp. 871-879.
Huston et al "Protein engineering of antibody binding sites: Recovery of specific activity in an anti-digoxin single-chain Fv analogue produced in *Escherichia coli*", Proc. Natl. Acad. Sci. USA, 1988, vol. 85, pp. 5879-5883.
Hjerrild, et al. "Production of full-length soluble Plasmodium falciparum RH5 protein vaccine using a *Drosophila melanogaster* Schneider 2 stable cell line system." Scientific reports, 2016 vol. 6, e.30357.
Jin, J. et al. "Accelerating the clinical development of protein-based vaccines for malaria by efficient purification using a four ammo acid C-terminal 'C-tag'." International journal for parasitology, 2017, vol. 47 No. 7, p. 435-446.
Malkin et al, 2005, "Phase 1 Clinical Trial of Apical Membrane Antigen 1: an Asexual Blood-Stage Vaccine for Plasmodium falciparum Malaria", Infection and Immunity, vol. 73, p. 3677-3685.
Morrison et al, 1984, "Chimeric human antibody molecules: Mouse antigen-binding domains with human constant region domains" Proc. Nati. Acad. Sci. USA, vol. 81, pp. 6851-6855.
Sabourin et al, "A flexible protein linker improves the function of epitope-tagged proteins in *Saccharomyces cerevisiae*" Yeast, 2007, 24: 39-45.
Swiech et al, "Bioreactor culture of recombinant *Drosophila melanogaster* S2 cells: characterization of metabolic features related to cell growth and production of the rabies virus glycoprotein" Cytotechnology (2008) 57:61-66 DOI 10.1007/s10616-008-9130-7.
Volz, et al. "Essential role of the PfRh5/PfRipr/CyRPA complex during Plasmodium falciparum invasion of erythrocytes." Cell host & microbe, 2016, vol. 20, No. 1, p. 60-71.

* cited by examiner

*Primary Examiner* — Padmavathi Baskar
(74) *Attorney, Agent, or Firm* — Hoffmann & Baron, LLP

(57) ABSTRACT

The present description relates to malaria vaccines comprising *Plasmodium falciparum* (Pf) polypeptide complexes and methods of producing the same. The Pf polypeptides in complexes or in a partially complexed arrangement may comprise two or more of the following polypeptides: PfRipr, PfCyrPa and PfRh5. *Drosophila* cells and expression vectors are also described.

5 Claims, 14 Drawing Sheets

Specification includes a Sequence Listing.

**SEQ ID NO: 1: *Pf*Ripr Full length (FL) nucleotide sequence**
```
AATTCGCCACCATGAAGCTGTGCATCCTGCTGGCCGTGGTGGCCTTCGTGGGACTGAGCCTGGGCATCGATCTGA
TCGAGGGCATCTTCTACGAGAAGAACGAGATCGACAAGCTGACCTTCAGCCTGGATCACCGCGTGCGCGATAAC
CTGAAGACCGACCTGATCCTGAACAACAACGGCGAGAACGATTACGCCTACCTGAACAAATACGTGTACACCATC
CTGAACCGCGACAGCACCGAGAAGATCAAGACCTTCTTCAGCCACAACAAGGACATGAAGTCCTGCGACTACTTC
ATCAGCAAGGAGTACAACAGCAGCGACAAGACCAACCAGATCTGCTACAAGAAGACGTTCTGCGGCGTCGTGAT
CCCCAACAGCGAGGAGATTAAGACGAACAAGATCACCAACGATAAGCTGTACTGCGCCCACTTCAACAGCACCCA
CATCATCATCTACTACATCAGCCAGCCCCTGCTGCTGGAGCCCCACGTGGTGTACGAGGAGACCTTTTTCGAGAA
GGGCAAGAACGACCAGATCAACTGCCAGGGCATGTACATCTCCCTGCGCTCCGTGCATGTGCACACCCACAACGC
CATCCTGCAGCAGGAGACCCTGACCTACATCAAGAACCTGTGCGACGGCAAGAACAACTGCAAGTTCGACTTCGA
CAGCATTAAGTACGAGAACAAGAGCCTGACCCACTACCTGTTCTTCATCAACATCCAGTACCAGTGCATCAGCCCC
CTGAACCTGCAGGAGAATGAGATGTGCGACGTGTACAACGACGATACGCACAAGGCCACGTGCAAATACGGCTT
CAACAAGATCGAGCTGCTGAAGAATGTGTGCGAGGAGAACTACCGCTGCACCCAGGATATCTGCAGCGTGAACC
AGTTCTGCGACGGCGAGAATGAGACCTGCACGTGCAAGACCAGCCTGCTGCCCAGCGCCAAGAACAATTGCGAG
TACAACGATCTGTGCACCGTGCTGAACTGCCCCGAGAACTCGACCTGCGAGCAGATCGGCAATGGCAAGAAGGC
CGAGTGCAAGTGCGAGAACGGCAAGTACTACCACAACAACAAGTGCTACACCAAGAACGATCTGGAGCTGGCCA
TCAAGATTGAGCCCCACAAGAAGGAGAAGTTCTATAAGAACAACCTGTACCAGGGCAAGGCCCTGAAGCCCGAG
TACATCTTCATGCAGTGCGAGAATGGCTTCAGCATCGAAGTGATCAACGCCTACGTGTCCTGCTACCGCGTGTCCT
TCAATCTGAACAAGCTGAAATACGTGACCGAGAGCCTGAAGAAGATGTGCGACGGAAAGACCAAGTGCGCCTAC
GGCAACACCATCGATCCCATCGATGATCTGAACCACCACAACATCTGCAACAACTTCAACACGATCTTTAAGTATG
ACTACCTGTGCGTGTTCAACAACCAGAACATCACCTCCGACAAGAACAGCCATCTGCACAGCAACATCCCCAGCCT
GTACAACTCCAGCATCCTGCCCGATATCAACAAGAGCAAGTTCCACCTGATCAGCCGCAACAGCCGCACCAACCA
GTACCCCCACAACAATATCAGTATGCTGGAGATCCAGAATGAGATCAGCAGCCACAACTCCAACCAGTTCTCCACC
GATCCCCACACCAACTCGAACAACATCAACAACATGAATATCAAGAAGGTGGAGATCTTCCGCAGCCGCTTCAGC
TCCAAGCTGCAGTGCCAGGGCGGCAAGATCAACATCGACAAGGCCATTCTGAAGGGCGGCGAGGGCTGCAATG
ATCTGCTGCTGACCAACAGCCTGAAGTCCTACTGCAACGACCTGAGCGAGTGCGATATCGGCCTGATCTACCACTT
CGATACCTACTGCATCAATGACCAGTACCTGTTCGTGTCCTACAGCTGCAGCAACCTGTGCAACAAGTGCCACAAC
AACTCCACGTGCTACGGCAACCGCTTCAACTACGATTGCTTCTGCGATAACCCCTACATCTCGAAGTACGGAAACA
AGCTGTGCGAGCGCCCCAACGATTGCGAGAGCGTGCTGTGCTCCCAGAACCAAGTGTGCCAGATCCTGCCGAAT
GATAAGCTGATCTGCCAGTGCGAGGAGGGCTACAAGAACGTGAAGGGAAAATGCGTGCCGGATAACAAGTGCG
ATCTGAGCTGCCCCAGCAACAAAGTGTGCGTGATCGAGAATGGAAAGCAGACCTGCAAGTGCTCCGAGCGCTTC
GTGCTGGAGAACGGCGTGTGCATCTGCGCCAACGATTACAAGATGGAGGATGGCATCAACTGCATTGCCAAGAA
CAAGTGCAAGCGCAAGGAGTACGAGAATATCTGCACCAACCCCAACGAGATGTGCGCCTACAATGAGGAGACCG
ATATCGTGAAGTGCGAGTGCAAGGAGCACTACTACCGCAGCAGCCGCGGAGAGTGCATTCTGAACGACTACTGC
AAGGACATCAATTGCAAGGAGAACGAGGAGTGCAGCATCGTGAACTTCAAGCCAGAGTGCGTGTGCAAGGAGA
ACCTGAAGAAGAACAACAAGGGCGAGTGCATCTACGAGAACAGCTGCCTGATCAACGAGGGCAACTGCCCCAAG
GATAGCAAGTGCATCTATCGCGAGTACAAGCCCCACGAGTGCGTGTGCAACAAGCAGGGACACGTGGCCGTGAA
TGGCAAATGCGTGCTGGAGGATAAGTGCGTGCACAACAAGAAGTGCAGCGAGAACAGCATCTGCGTGAACGTG
ATGAACAAGGAGCCAATCTGCGTGTGCACCTACAACTACTACAAGAAGGACGGCGTGTGCCTGATCCAGAACCC
CTGCCTGAAGGATAACGGCGGCTGCTCCCGCAACTCCGAGTGCACCTTCAAGTACAGCAAGATCAACTGCACGTG
CAAGGAGAACTACAAGAACAAGGATGATAGCTGCGTGCCCAACACGAACGAGTACGATGAGAGCTTCACCTTCC
AGTATAACGACGACGCCAGCATCATCCTGGGCGCCTGCGGCATGATCGAGTTCAGCTACATCTACAACCAGATTA
TCTGGAAGATTAACAACTCGAAGGAGTCCTACGTGTTCTACTACGATTACCCCACCGCCGGCAACATCGAGGTGC
AGATTAAGAATGAGATTTTCCACACGATCATCTATCTGAAGAAGAAGATCGGCAACAGCGTGATCTACGACGATT
TCCAGGTGGACCACCAGACCTGCATCTATGAGAATGTGTTTTACTACAGCAACCAGAATAGCGCCTGGTCCCACC
CCCAGTTCGAGAAATAAGC
```
Secretion signal
*Pf*Ripr
Strep

Figure 3

**SEQ ID NO: 2: *Pf*CyrPa nucleotide sequence**
AATTCGCCACCATGAAGCTGTGCATCCTGCTGGCCGTGGTGGCCTTCGTGGGACTGAGTCTGGGAAGCCGCCAC
GTGTTCATCCGCACCGAGCTGAGCTTCATCAAGAACAACGTGCCCTGCATCCGCGACATGTTCTTCATCTACAAGC
GCGAGCTGTACAACATCTGCCTGGATGATCTGAAGGGCGAGGAGGATGAGACCCACATCTACGTGCAGAAGAAA
GTGAAGGACAGCTGGATCACCCTGAACGACCTGTTCAAGGAGACCGATCTGACCGGACGCCCCCACATCTTCGCC
TACGTGGACGTGGAGGAGATCATCATTCTGCTGTGCGAGGATGAGGAGTTCAGCAACCGCAAGAAGGATATGAC
CTGCCACCGCTTCTACAGCAACGATGGCAAGGAGTACAACAACAGCGAGATCACCATCAGCGACTACATCCTGAA
GGATAAGCTGCTGTCCAGCTACGTGTCCCTGCCCCTGAAGATCGAGAACCGCGAGTACTTCCTGATCTGCGGCGT
GTCCCCCTACAAGTTCAAGGATGATAACAAGAAGGACGACATCCTGTGCATGGCCAGCCACGATAAGGGCGAGA
CCTGGGGCACCAAGATCGTGATTAAGTACGACAACTACAAGCTGGGCGTGCAGTACTTCTTCCTGCGCCCCTACA
TCAGCAAGAACGATCTGAGCTTCCACTTCTACGTGGGCGACAACATCAACAACGTGAAGAACGTGAACTTCATCG
AGTGCACCCACGAGAAGGATCTGGAGTTCGTGTGCTCCAACCGCGATTTTCTGAAGGACAACAAGGTGCTGCAG
GATGTGTCCACCCTGAATGATGAGTACATCGTGTCCTACGGCAACGACAACAACTTCGCCGAGTGCTACATCTTCT
TCAACAACGAGAACAGCATCCTGATCAAGCCCGAGAAGTACGGCAACACCACCGCCGGATGCTACGGCGGCACC
TTCGTGAAGATTGATGAGAACCGCACCCTGTTCATCTACTCCAGCAGCCAGGGCATCTACAACATCCACACCATCT
ACTACGCCAACTACGAG▓▓▓▓▓▓▓▓▓▓▓▓▓▓▓GC
Secretion signal
PfCyrPa
▓▓▓▓

**SEQ ID NO: 3: *Pf*Rh5 version 1 nucleotide sequence**
AATTCGCCACCATGAAGCTGTGCATCCTGCTGGCCGTGGTGGCCTTCGTGGGACTGAGTCTGGGCGACGTGAAG
AACAACGAGGACTACAAGAACGTGGACTATAAGAATGTGAACTTCCTGCAGTACCACTTCAAGGAGCTGAGCAA
CTACAATATCGCCAACAGCATCGACATTCTGCAGGAGAAGGAGGGCCACCTGGATTTCGTGATCATCCCCCACTA
CACCTTTCTGGACTACTACAAGCACCTGAGCTACAACTCCATCTACCACAAGAGCAGCACCTACGGCAAGTGCATT
GCCGTGGATGCCTTCATCAAGAAGATCAACGAGACCTACGACAAAGTGAAGTCCAAGTGCAACGACATCAAGAA
CGACCTGATCGCCACGATCAAGAAGCTGGAGCACCCCTACGATATCAACAACAAGAACGATGACAGCTACCGCTA
CGACATCAGCGAGGAGATCGACGATAAGTCCGAGGAGACGGACGACGAGACCGAGGAGGTGGAGGATAGCAT
CCAGGATACCGATAGCAACCACACCCCCAGCAACAAGAAGAAGAATGATCTGATGAACCGCACCTTTAAGAAGA
TGATGGACGAGTACAATACGAAAAAGAAGAAGCTGATCAAGTGCATCAAGAATCACGAGAACGACTTCAACAAG
ATCTGCATGGACATGAAGAACTACGGCACCAACCTGTTCGAGCAGCTGTCCTGCTACAACAACAACTTCTGCAAC
ACCAACGGCATCCGCTACCACTACGATGAGTACATCCACAAGCTGATCCTGAGCGTGAAGTCGAAGAACCTGAAC
AAGGATCTGAGCGACATGACCAACATCCTGCAGCAGAGCGAGCTGCTGCTGACCAATCTGAACAAGAAGATGGG
CAGCTACATCTACATCGACACCATCAAGTTCATTCACAAGGAGATGAAGCACATCTTCAACCGCATCGAGTACCAC
ACCAAGATCATCAACGACAAGACGAAGATCATTCAGGACAAGATCAAGCTGAACATCTGGCGCACCTTCCAGAA
GGATGAGCTGCTGAAGCGCATCCTGGATATGAGCAACGAGTACAGCCTGTTCATCACCAGCGATCATCTGCGCCA
GATGCTGTACAACACCTTCTACAGCAAGGAGAAGCACCTGAACAACATCTTCCACCACCTGATCTACGTGCTGCA
GATGAAGTTCAACGACGTGCCCATCAAGATGGAGTACTTCCAGACCTATAAGAAGAACAAGCCCCTGACCCAG▓▓
▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓
▓▓▓▓▓▓▓▓▓▓▓▓▓▓▓▓▓GC
Secretion signal
PfRh5
▓▓▓▓
▓▓▓▓▓▓▓▓▓▓▓▓

Figure 3A

SEQ ID NO: 4: *Pf*Rh5 version 2 nucleotide sequence

AATTCGCCACCATGAAGCTGTGCATCCTGCTGGCCGTGGTGGCCTTCGTGGGACTGAGTCTGGGCGACTACAAG
GATGACGACGACAAGGACGTGAAGAACAACGAGGACTACAAGAACGTGGACTATAAGAATGTGAACTTCCTGCA
GTACCACTTCAAGGAGCTGAGCAACTACAATATCGCCAACAGCATCGACATTCTGCAGGAGAAGGAGGGCCACC
TGGATTTCGTGATCATCCCCCACTACACCTTTCTGGACTACTACAAGCACCTGAGCTACAACTCCATCTACCACAAG
AGCAGCACCTACGGCAAGTGCATTGCCGTGGATGCCTTCATCAAGAAGATCAACGAGACCTACGACAAAGTGAA
GTCCAAGTGCAACGACATCAAGAACGACCTGATCGCCACGATCAAGAAGCTGGAGCACCCCTACGATATCAACAA
CAAGAACGATGACAGCTACCGCTACGACATCAGCGAGGAGATCGACGATAAGTCCGAGGAGACGGACGACGAG
ACCGAGGAGGTGGAGGATAGCATCCAGGATACCGATAGCAACCACACCCCCAGCAACAAGAAGAAGAATGATCT
GATGAACCGCACCTTTAAGAAGATGATGGACGAGTACAATACGAAAAAGAAGAAGCTGATCAAGTGCATCAAGA
ATCACGAGAACGACTTCAACAAGATCTGCATGGACATGAAGAACTACGGCACCAACCTGTTCGAGCAGCTGTCCT
GCTACAACAACAACTTCTGCAACACCAACGGCATCCGCTACCACTACGATGAGTACATCCACAAGCTGATCCTGAG
CGTGAAGTCGAAGAACCTGAACAAGGATCTGAGCGACATGACCAACATCCTGCAGCAGAGCGAGCTGCTGCTGA
CCAATCTGAACAAGAAGATGGGCAGCTACATCTACATCGACACCATCAAGTTCATTCACAAGGAGATGAAGCACA
TCTTCAACCGCATCGAGTACCACACCAAGATCATCAACGACAAGACGAAGATCATTCAGGACAAGATCAAGCTGA
ACATCTGGCGCACCTTCCAGAAGGATGAGCTGCTGAAGCGCATCCTGGATATGAGCAACGAGTACAGCCTGTTCA
TCACCAGCGATCATCTGCGCCAGATGCTGTACAACACCTTCTACAGCAAGGAGAAGCACCTGAACAACATCTTCC
ACCACCTGATCTACGTGCTGCAGATGAAGTTCAACGACGTGCCCATCAAGATGGAGTACTTCCAGACCTATAAGA
AGAACAAGCCCCTGACCCAGTAGGC

Secretion signal

Flag tag

PfRh5

---

SEQ ID NO: 5: *Pf*EBA175 nucleotide sequence

AATTCGCCACCATGAAGCTGTGCATCCTGCTGGCCGTGGTGGCCTTCGTGGGACTGAGTCTGGGACAGGAGGCC
GTGCCAGAGGAGAGCACCGAGATTGCCCACCGCACCGAGACCCGCACCGATGAGCGCAAGAATCAGGAGCCCG
CCAACAAGGATCTGAAGAACCCCCAGCAGAGCGTGGGCGAGAACGGCACGAAGGATCTGCTGCAGGAGGATCT
GGGAGGCAGCCGCAGCGAGGATGAAGTGACCCAGGAGTTCGGCGTGAACCACGGCATCCCCAAGGGCGAGGA
TCAGACCCTGGGAAAGTCCGATGCCATCCCCAACATCGGCGAGCCCGAGACCGGAATCAGTACCACCGAGGAGT
CCCGCCACGAGGAGGGCCATAACAAGCAGGCCCTGAGCACCTCCGTGGATGAGCCCGAGCTGAGCGATACCCTG
CAGCTGCACGAGGATACCAAGGAGAACGATAAGCTGCCCCTGGAGAGCAGCACCATCACCAGCCCAACCGAGAG
CGGCAGCAGCGATACCGAGGAGACCCCATCCATTAGCGAGGGCCCGAAGGGCAACGAGCAGAAGAAGCGCGAC
GACGATAGCCTGAGCAAGATCAGCGTGTCCCCCGAGAACAGCCGCCCAGAGACCGATGCCAAGGATACCAGCAA
CCTGCTGAAGCTGAAGGGCGACGTGGACATCAGCATGCCCAAGGCCGTGATCGGCAGCTCCCCAACGATAACA
TCAACGTGACCGAGCAGGGCGACAACATCTCGGGCGTGAACAGCAAGCCCCTGTCCGATGATGTGCGCCCCGAT
AAGAACCATGAGGAAGTGAAGGAGCACACCAGCAACAGCGATAACGTGCAGCAGTCCGGCGGCATCGTGAACA
TGAACGTGGAGAAGGAGCTGAAGGACACCCTGGAGAACCCCAGCTCCAGCCTGGATGAGGGAAAGGCCCATGA
GGAGCTGTCCGAGCCCAACCTGTCCAGCGATCAGGATATGAGCAACACCCCAGGCCCCTGGATAACACCTCGG
AGGAGACGACCGAGCGCATCAGCAACAACGAGTACAAAGTGAACGAGCGCGAGGGCGAGCGCACCCTGACCAA
GGAGTATGAGGATATCGTGCTGAAGTCCCACATGAACCGCGAGAGCGACGATGGCGAGCTGTACGATGAGAAC
AGCGATCTGAGCACCGTGAACGATGAGTCCGAGGATGCCGAGGCCAAGATGAAGGGCAATGATACCAGCGAGA
TGAGCCACAACAGCAGCCAGCACATCGAGAGCGATCAGCAGAAGAACGATATGAAGACCGTGGGCGACCTGGG
CACCACCCACGTGCAGAATGAGATCTCCGTGCCCGTGACCGGCGAGATCGATGAAGCTGCGCGAGAGCAAG
GAGTCCAAGATCCACAAGGCCGAGGAGGAGCGCCTGAGCCACACCGATATCCACAAGATCAACCCCGAGGATCG
CAACTCCAACACCCTGCACCTGAAGGATATCCGCAACGAGGAGAATGAGCGCCACCTGACGAACCAGAACATCA
ACATCAGCCAGGAGCGCGACCTGCAGAAGCACGGCTTCCACACCATGAACAACCTGCACGGCGACGGCGTGTCC
GAGCGCAGCCAGATCAATCACTCGCACCACGGCAACCGCCAGGATCGCGGAGGAAATAGTGGAAGCGCCTGAG
CTCACCCCAGTTCGAGAAAGC

Secretion signal
PfEBA175

Stop

Figure 3B

SEQ ID NO: 6: *Pf*RiprFL amino acid sequence

MKLCILLAVVAFVGLSLGIDLIEGIFYEKNEIDKLTFSLDHRVRDNLKTDLILNNNGENDYAYLNKYVYTILNRDSTEKIKTF
FSHNKDMKSCDYFISKEYNSSDKTNQICYKKTFCGVVIPNSEEIKTNKITNDKLYCAHFNSTHIIIYYISQPLLLEPHVVYEET
FFEKGKNDQINCQGMYISLRSVHVHTHNAILQQETLTYIKNLCDGKNNCKFDFDSIKYENKSLTHYLFFINIQYQCISPLN
LQENEMCDVYNDDTHKATCKYGFNKIELLKNVCEENYRCTQDICSVNQFCDGENETCTCKTSLLPSAKNNCEYNDLCT
VLNCPENSTCEQIGNGKKAECKCENGKYYHNNKCYTKNDLELAIKIEPHKKEKFYKNNLYQGKALKPEYIFMQCENGFSI
EVINAYVSCYRVSFNLNKLKYVTESLKKMCDGKTKCAYGNTIDPIDDLNHHNICNNFNTIFKYDYLCVFNNQNITSDKNS
HLHSNIPSLYNSSILPDINKSKFHLISRNSRTNQYPHNNISMLEIQNEISSHNSNQFSTDPHTNSNNINNMNIKKVEIFRS
RFSSKLQCQGGKINIDKAILKGGEGCNDLLLTNSLKSYCNDLSECDIGLIYHFDTYCINDQYLFVSYSCSNLCNKCHNNST
CYGNRFNYDCFCDNPYISKYGNKLCERPNDCESVLCSQNQVCQILPNDKLICQCEEGYKNVKGKCVPDNKCDLSCPSN
KVCVIENGKQTCKCSERFVLENGVCICANDYKMEDGINCIAKNKCKRKEYENICTNPNEMCAYNEETDIVKCECKEHYY
RSSRGECILNDYCKDINCKENEECSIVNFKPECVCKENLKKNNKGECIYENSCLINEGNCPKDSKCIYREYKPHECVCNKQ
GHVAVNGKCVLEDKCVHNKKCSENSICVNVMNKEPICVCTYNYYKKDGVCLIQNPCLKDNGGCSRNSECTFKYSKINC
TCKENYKNKDDSCVPNTNEYDESFTFQYNDDASIILGACGMIEFSYIYNQIIWKINNSKESYVFYYDYPTAGNIEVQIKNE
IFHTIIYLKKKIGNSVIYDDFQVDHQTCIYENVFYYSNQN

Secretion signal
PfEBA175

SEQ ID NO: 7: *Pf*CyrPa amino acid sequence

MKLCILLAVVAFVGLSLGSRHVFIRTELSFIKNNVPCIRDMFFIYKRELYNICLDDLKGEEDETHIYVQKKVKDSWITLNDL
FKETDLTGRPHIFAYVDVEEIIILLCEDEEFSNRKKDMTCHRFYSNDGKEYNNSEITISDYILKDKLLSSYVSLPLKIENREYFL
ICGVSPYKFKDDNKKDDILCMASHDKGETWGTKIVIKYDNYKLGVQYFFLRPYISKNDLSFHFYVGDNINNVKNVNFIEC
THEKDLEFVCSNRDFLKDNKVLQDVSTLNDEYIVSYGNDNNFAECYIFFNNENSILIKPEKYGNTTAGCYGGTFVKIDEN
RTLFIYSSSQGIYNIHTIYYANYE

Secretion signal
PfCyrPa

SEQ ID NO: 8: *Pf*Rh5 Full length (FL) amino acid sequence

MIRIKKKLILTIIYIHLFILNRLSFENAIKKTKNQENNLTLLPIKSTEEEKDDIKNGKDIKKEIDNDKENIKTNNAKDHSTYIKSY
LNTNVNDGLKYLFIPSHNSFIKKYSVFNQINDGMLLNEKNDVKNNEDYKNVDYKNVNFLQYHFKELSNYNIANSIDILQ
EKEGHLDFVIIPHYTFLDYYKHLSYNSIYHKSSTYGKCIAVDAFIKKINETYDKVKSKCNDIKNDLIATIKKLEHPYDINNKND
DSYRYDISEEIDDKSEETDDETEEVEDSIQDTDSNHTPSNKKKNDLMNRTFKKMMDEYNTKKKKLIKCIKNHENDFNKI
CMDMKNYGTNLFEQLSCYNNNFCNTNGIRYHYDEYIHKLILSVKSKNLNKDLSDMTNILQQSELLLTNLNKKMGSYIYI
DTIKFIHKEMKHIFNRIEYHTKIINDKTKIIQDKIKLNIWRTFQKDELLKRILDMSNEYSLFITSDHLRQMLYNTFYSKEKHL
NNIFHHLIYVLQMKFNDVPIKMEYFQTYKKNKPLTQ*

SEQ ID NO: 9: *Pf*Rh5 version 1 amino acid sequence

MKLCILLAVVAFVGLSLGDVKNNEDYKNVDYKNVNFLQYHFKELSNYNIANSIDILQEKEGHLDFVIIPHYTFLDYYKHLS
YNSIYHKSSTYGKCIAVDAFIKKINETYDKVKSKCNDIKNDLIATIKKLEHPYDINNKNDDSYRYDISEEIDDKSEETDDETE
EVEDSIQDTDSNHTPSNKKKNDLMNRTFKKMMDEYNTKKKKLIKCIKNHENDFNKICMDMKNYGTNLFEQLSCYNN
NFCNTNGIRYHYDEYIHKLILSVKSKNLNKDLSDMTNILQQSELLLTNLNKKMGSYIYIDTIKFIHKEMKHIFNRIEYHTKII
NDKTKIIQDKIKLNIWRTFQKDELLKRILDMSNEYSLFITSDHLRQMLYNTFYSKEKHLNNIFHHLIYVLQMKFNDVPIKM
EYFQTYKKNKPLTQ

Secretion signal
PfRh5

Figure 3C

SEQ ID NO: 10: *Pf*EBA175 amino acid sequence (760-1298 3D7)

QEAVPEESTEIAHRTETRTDERKNQEPANKDLKNPQQSVGENGTKDLLQEDLGGSRSEDEVTQEFGVNHGIPKGEDQ
TLGKSDAIPNIGEPETGISTTEESRHEEGHNKQALSTSVDEPELSDTLQLHEDTKENDKLPLESSTITSPTESGSSDTEETPS
ISEGPKGNEQKKRDDDSLSKISVSPENSRPETDAKDTSNLLKLKGDVDISMPKAVIGSSPNDNINVTEQGDNISGVNSKP
LSDDVRPDKNHEEVKEHTSNSDNVQQSGGIVNMNVEKELKDTLENPSSSLDEGKAHEELSEPNLSSDQDMSNTPGPL
DNTSEETTERISNNEYKVNEREGERTLTKEYEDIVLKSHMNRESDDGELYDENSDLSTVNDESEDAEAKMKGNDTSEM
SHNSSQHIESDQQKNDMKTVGDLGTTHVQNEISVPVTGEIDEKLRESKESKIHKAEEERLSHTDIHKINPEDRNSNTLHL
KDIRNEENERHLTNQNINISQERDLQKHGFHTMNNLHGDGVSERSQINHSHHGNRQDRGGNSG

SEQ ID NO: 18: *Pf*Rh5 version 2 amino acid sequence

MKLCILLAVVAFVGLSLG▓▓▓▓▓▓▓DVKNNEDYKNVDYKNVNFLQYHFKELSNYNIANSIDILQEKEGHLDFVIIPHYT
FLDYYKHLSYNSIYHKSSTYGKCIAVDAFIKKINETYDKVKSKCNDIKNDLIATIKKLEHPYDINNKNDDSYRYDISEEIDDKS
EETDDETEEVEDSIQDTDSNHTPSNKKKNDLMNRTFKKMMDEYNTKKKKLIKCIKNHENDFNKICMDMKNYGTNLFE
QLSCYNNNFCNTNGIRYHYDEYIHKLILSVKSKNLNKDLSDMTNILQQSELLLTNLNKKMGSYIYIDTIKFIHKEMKHIFNR
IEYHTKIINDKTKIIQDKIKLNIWRTFQKDELLKRILDMSNEYSLFITSDHLRQMLYNTFYSKEKHLNNIFHHLIYVLQMKFN
DVPIKMEYFQTYKKNKPLTQ▓

Secretion signal
▓▓▓▓
PfRh5
▓▓▓▓

SEQ ID NO: 11: pExpreS2-1 vector nucleotide sequence
CGTAAGTATCAAGGTTACAAGACAGGTTTAAGGAGACCAATAGAAACTGGGCTTGTCGAGACAGAGAAGACTCT
TGCGTTTCTGATAGGCACCTATTGGTCTTACTGACATCCACTTTGCCTTTCTCTCCACAGGAATTCTGGATCCTCTA
GACCGGTCATATGCGGCCGCGGATCGATCGATATCTGACTAAATCTTAGTTTGTATTGTCATGTTTTAATACAATA
TGTTATGTTTAAATATGTTTTTAATAAATTTTATAAAATAATTTCAACTTTTATTGTAACAACATTGTCCATTTACACA
CTCCTTTCAAGCGCGTGGGACTCGATGCTCGGCGCCACTCAAAGGCGGTAATACGGTTATCCACAGAATCAGGGG
ATAACGCAGGAAAGAACATGTGAGCAAAAGGCCAGCAAAAGGCCAGGAACCGTAAAAAGGCCGCGTTGCTGGC
GTTTTTCCATAGGCTCCGCCCCCCTGACGAGCATCACAAAAATCGACGCTCAAGTCAGAGGTGGCGAAACCCGAC
AGGACTATAAAGATACCAGGCGTTTCCCCCTGGAAGCTCCCTCGTGCGCTCTCCTGTTCCGACCCTGCCGCTTACC
GGATACCTGTCCGCCTTTCTCCCTTCGGGAAGCGTGGCGCTTTCTCAATGCTCACGCTGTAGGTATCTCAGTTCGG
TGTAGGTCGTTCGCTCCAAGCTGGGCTGTGTGCACGAACCCCCCGTTCAGCCCGACCGCTGCGCCTTATCGGTA
ACTATCGTCTTGAGTCCAACCCGGTAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACTACGGCTACACTAGAAGGACAGTA
TTTGGTATCTGCGCTCTGCTGAAGCCAGTTACCTTCGGAAAAAGAGTTGGTAGCTCTTGATCCGGCAAACAAACC
ACCGCTGGTAGCGGTGGTTTTTTTGTTTGCAAGCAGCAGATTACGCGCAGAAAAAAAGGATCTCAAGAAGATCCT
TTGATCTTTTCTACGGGGTCTGACGCTCAGTGGAACGAAAACTCACGTTAAGGGATTTTGCATGCGCTAAGCGGG
CTTTATAAAACGGGCTGCGGGACCAGTTTTCATATCACTACCGTTTGAGTTCTTGTGCTGTGTGGATACTCCTCCC
GACACCGAATTAATTCGGATCTCTGCAAGGGATTTTGGTCATGAACAATAAAACTGTCTGCTTACATAAACAGTAA
TACAAGGGGTGTTCATAGTATAATACGACTCACTATAGGAGGGCCACCATGGCCAAGTTGACCAGTGCCGTTCCG
GTGCTCACCGCGCGCGACGTCGCCGGAGCGGTCGAGTTCTGGACCGACCGGCTCGGGTTCAGCCGGGACTTCGT
GGAGGACGACTTCGCCGGTGTGGTCCGGGACGACGTGACCCTGTTCATCAGCGCGGTCCAGGACCAGGTGGTGC
CGGACAACACCCTGGCCTGGGTGTGGGTGCGCGGCCTGGACGAGCTGTACGCCGAGTGGTCGGAGGTCGTGTC
CACGAACTTCCGGGACGCCTCCGGGCCGGCCATGACCGAGATCGGCGAGCAGCCGTGGGGCGGGAGTTCGCC
CTGCGCGACCCGGCCGGCAACTGCGTGCACTTCGTGGCCGAGGAGCAGGACTGACCGACGCCGACCAACACCGC
CGGTCCGACGGCGGCCCACGGGTCCCAGGGGGTCGACCTCGAAACTTGTTTATTGCAGCTTATAATGGTTACAA
ATAAAGCAATAGCATCACAAATTTCACAAATAAAGCATTTTTTTCACTGCATTCTAGTTGTGGTTTGTCCAAACTCA
TCAATGTATCTTATCATGTCTTCACGTAATAAGTGTGCGGCTAGCAGTCAACTACTAGTGAATGCCCTACTAGAAG
ATGTGTGTTGCACAAAATGTCCCTGGAATAACCAATTTGAAGTGCAGATAGCAGTAAACGTAAGCTAATATGAAT
ATTATTTAACTGTAATGTTTTAATATCGCTGGACATTACTAATAAACCCACTATAAACACATGTACATATGTATGTT
TTGGCATACAATGAGTAGTTGGGGAAAAAATGTGTAAAAGCACCGTGACCATCACAGCATAAAGATAACCAGCT
GAAGTATCGAATATGAGTAACCCCCAAATTGAATCACATGCCGCAACTGATAGGACCCATGGAAGTACACTCTTC
ATGGCGATATACAAGACACACACAAGCACGAACACCCAGTTGCGGAGGAAATTCTCCGTAAATGAAAACCCAATC

Figure 3D

GGCGAACAATTCATACCCATATATGGTAAAAGTTTTGAACGCGACTTAAGAGCGCCGGAGTATAAATAGAGGCG
CTTCGTCTACGGAGCGACAATTCAATTCAAACAAGCAAAGTGAACACGTCGCTAAGCGAAAGCTAAGCAAATAAA
CAAGCGCAGCTGAACAAGCTAAACAATCTGCAGAAGCTTGGTACCCTCGAGCT

SEQ ID NO: 12: pExpreS2-2 vector nucleotide sequence
AATTCGGATCTCTGCAAGGGATTTTGGTCATGAACAATAAAACTGTCTGCTTACATAAACAGTAATACAAGGGGT
GTTCATAGTATAATACGACTCACTATAGGAGGGCCACCATGAGCCACATCCAGCGCGAAACCAGCTGCAGCCGTC
CGCGCCTGAACAGCAACATGGATGCCGATCTGTACGGCTACAAATGGGCCCGCGATAACGTGGGCCAGAGCGGC
GCTACCATCTACCGCCTGTACGGCAAACCGGATGCCCCGGAACTGTTCCTGAAACACGGCAAAGGCAGCGTGGC
CAACGATGTGACCGATGAAATGGTGCGCCTGAACTGGCTGACCGAGTTCATGCCGCTGCCGACCATCAAACACTT
CATCCGCACCCCGGATGATGCCTGGCTGCTGACCACCGCCATTCCGGGCAAAACCGCCTTCCAGGTGCTGGAAGA
ATACCCGGATAGCGGCGAAAACATCGTGGATGCCCTGGCCGTGTTCCTGCGCCGCCTGCACAGCATCCCGGTGTG
CAACTGCCCGTTCAACAGCGATCGCGTGTTCCGCCTGGCTCAGGCCCAGAGCCGCATGAACAACGGCCTGGTGG
ATGCCAGCGATTTCGATGATGAACGCAACGGCTGGCCGGTGGAACAGGTGTGGAAAGAGATGCACAAACTGCT
GCCGTTCAGCCCGGATTCCGTGGTGACCCACGGCGATTTCAGCCTGGATAACCTGATCTTCGATGAGGGCAAACT
GATCGGCTGCATCGATGTGGGCCGCGTGGGCATTGCCGATCGCTACCAGGATCTGGCCATCCTGTGGAACTGCCT
GGGCGAGTTCAGCCCGAGCCTGCAGAAACGCCTGTTCCAGAAGTACGGCATCGATAACCCGGATATGAACAAAC
TGCAGTTCCACCTGATGCTGGATGAGTTCTTCTAATAAGTCGACCTCGAAACTTGTTTATTGCAGCTTATAATGGTT
ACAAATAAAGCAATAGCATCACAAATTTCACAAATAAAGCATTTTTTTCACTGCATTCTAGTTGTGGTTTGTCCAAA
CTCATCAATGTATCTTATCATGTCTTCACGTAATAAGTGTGCGGCTAGCAGTCAACTACTAGTGAATGCCCTACTA
GAAGATGTGTGTTGCACAAAATGTCCCTGGAATAACCAATTTGAAGTGCAGATAGCAGTAAACGTAAGCTAATAT
GAATATTATTTAACTGTAATGTTTTAATATCGCTGGACATTACTAATAAACCCACTATAAACACATGTACATATGTA
TGTTTTGGCATACAATGAGTAGTTGGGGAAAAAATGTGTAAAAGCACCGTGACCATCACAGCATAAAGATAACCA
GCTGAAGTATCGAATATGAGTAACCCCCAAATTGAATCACATGCCGCAACTGATAGGACCCATGGAAGTACACTC
TTCATGGCGATATACAAGACACACACAAGCACGAACACCCAGTTGCGGAGGAAATTCTCCGTAAATGAAAACCCA
ATCGGCGAACAATTCATACCCATATATGGTAAAAGTTTTGAACGCGAGCGAACTTAAGAGCGCCGGAGTATAAAT
AGAGGCGCTTCGTCTACGGAGCGACAATTCAATTCAAACAAGCAAAGTGAACACGTCGCTAAGCGAAAGCTAAG
CAAATAAACAAGCGCAGCTGAACAAGCTAAACAATCTGCAGAAGCTTGGTACCCTCGAGCTCAGCTGAATTCTGG
ATCCTCTAGACCGGTCATATGCGGCCGCGGATCGATCGATATCTGACTAAATCTTAGTTTGTATTGTCATGTTTTAA
TACAATATGTTATGTTTAAATATGTTTTTAATAAATTTTATAAAATAATTTCAACTTTTATTGTAACAACATTGTCCA
TTTACACACTCCTTTCAAGCGCGTGGGACTCGATGCTCGGCGCCACTCAAAGGCGGTAATACGGTTATCCACAGA
ATCAGGGGATAACGCAGGAAAGAACATGTGAGCAAAAGGCCAGCAAAAGGCCAGGAACCGTAAAAAGGCCGC
GTTGCTGGCGTTTTTCCATAGGCTCCGCCCCCTGACGAGCATCACAAAAATCGACGCTCAAGTCAGAGGTGGCG
AAACCCGACAGGACTATAAAGATACCAGGCGTTTCCCCCTGGAAGCTCCCTCGTGCGCTCTCCTGTTCCGACCCTG
CCGCTTACCGGATACCTGTCCGCCTTTCTCCCTTCGGGAAGCGTGGCGCTTTCTCAATGCTCACGCTGTAGGTATCT
CAGTTCGGTGTAGGTCGTTCGCTCCAAGCTGGGCTGTGTGCACGAACCCCCCGTTCAGCCCGACCGCTGCGCCTT
ATCCGGTAACTATCGTCTTGAGTCCAACCCGGTAAGACACGACTTATCGCCACTGGCAGCAGCCACTGGTAACAG
GATTAGCAGAGCGAGGTATGTAGGCGGTGCTACAGAGTTCTTGAAGTGGTGGCCTAACTACGGCTACACTAGAA
GGACAGTATTTGGTATCTGCGCTCTGCTGAAGCCAGTTACCTTCGGAAAAAGAGTTGGTAGCTCTTGATCCGGCA
AACAAACCACCGCTGGTAGCGGTGGTTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAACTCACGTTAAGGGATTTTGCATGCGCT
AAGCGGGCTTTATAAAACGGGCTGCGGGACCAGTTTTCATATCACTACCGTTTGAGTTCTTGTGCTGTGTGGATAC
TCCTCCCGACACCGAATT

SEQ ID NO: 13: pExpreS2-PAC vector nucleotide sequence
TAATTCGGATCTCTGCAAGGGATTTTGGTCATGAACAATAAAACTGTCTGCTTACATAAACAGTAATACAAGGGG
TGTTCATAGTATAATACGACTCACTATAGGAGGGCCACCATGACCGAGTACAAGCCCACCGTGCGCCTGGCCACC
CGCGACGATGTGCCACGCGCCGTGCGCACCCTGGCCGCCGCCTTTGCCGATTATCCAGCCACCCGCCATACCGTG
GACCCCGATCGCCATATTGAGCGCGTGACCGAGCTGCAGGAGCTGTTCCTGACCCGCGTGGGCCTGGATATTGG
CAAAGTGTGGGTGGCCGATGACGGAGCCGCCGTGGCCGTGTGGACCACCCCAGAGAGTGTGGAGGCCGGAGCC
GTGTTCGCCGAGATTGGACCACGCATGGCCGAGCTGAGTGGAAGTCGCCTGGCCGCCCAGCAGCAGATGGAGG
GACTGCTGGCCCCACACCGCCCAAAGGAGCCAGCCTGGTTTCTGGCCACCGTGGGAGTGTCCCAGATCACCAG
GGAAAGGGACTGGGAAGTGCCGTGGTGCTGCCAGGCGTGGAGGCCGCCGAGCGCGCCGGCGTGCCAGCCTTTC

Figure 3E

TGGAGACCAGTGCCCCACGCAACCTGCCCTTTTACGAGCGCCTGGGCTTTACCGTGACCGCCGATGTGGAGGTGC
CAGAGGGCCCACGCACCTGGTGCATGACCCGCAAGCCAGGCGCCTAAGTCGACCTCGAAACTTGTTTATTGCAGC
TTATAATGGTTACAAATAAAGCAATAGCATCACAAATTTCACAAATAAAGCATTTTTTTCACTGCATTCTAGTTGTG
GTTTGTCCAAACTCATCAATGTATCTTATCATGTCTTCACGTAATAAGTGTGCGGCTAGCAGTCAACTACTAGTGA
ATGCCCTACTAGAAGATGTGTGTTGCACAAAATGTCCCTGGAATAACCAATTTGAAGTGCAGATAGCAGTAAACG
TAAGCTAATATGAATATTATTTAACTGTAATGTTTTAATATCGCTGGACATTACTAATAAACCCACTATAAACACAT
GTACATATGTATGTTTTGGCATACAATGAGTAGTTGGGGAAAAAATGTGTAAAAGCACCGTGACCATCACAGCAT
AAAGATAACCAGCTGAAGTATCGAATATGAGTAACCCCCAAATTGAATCACATGCCGCAACTGATAGGACCCATG
GAAGTACACTCTTCATGGCGATATACAAGACACACACAAGCACGAACACCCAGTTGCGGAGGAAATTCTCCGTAA
ATGAAAACCCAATCGGCGAACAATTCATACCCATATATGGTAAAAGTTTTGAACGCGAGCGAACTTAAGAGCGCC
GGAGTATAAATAGAGGCGCTTCGTCTACGGAGCGACAATTCAATTCAAACAAGCAAAGTGAACACGTCGCTAAG
CGAAAGCTAAGCAAATAAACAAGCGCAGCTGAACAAGCTAAACAATCTGCAGAAGCTTGGTACCCTCGAGCTCG
TAAGTATCAAGGTTACAAGACAGGTTTAAGGAGACCAATAGAAACTGGGCTTGTCGAGACAGAGAAGACTCTTG
CGTTTCTGATAGGCACCTATTGGTCTTACTGACATCCACTTTGCCTTTCTCTCCACAGGAATTCTGGATCCTCTAGA
CCGGTCATATGCGGCCGCGGATCGATCGATATCTGACTAAATCTTAGTTTGTATTGTCATGTTTTAATACAATATGT
TATGTTTAAATATGTTTTTAATAAATTTTATAAAATAATTTCAACTTTTATTGTAACAACATTGTCCATTTACACACTC
CTTTCAAGCGCGTGGGACTCGATGCTCGGCGCCACTCAAAGGCGGTAATACGGTTATCCACAGAATCAGGGGAT
AACGCAGGAAAGAACATGTGAGCAAAAGGCCAGCAAAAGGCCAGGAACCGTAAAAAGGCCGCGTTGCTGGCGT
TTTTCCATAGGCTCCGCCCCCCTGACGAGCATCACAAAAATCGACGCTCAAGTCAGAGGTGGCGAAACCCGACAG
GACTATAAAGATACCAGGCGTTTCCCCCTGGAAGCTCCCTCGTGCGCTCTCCTGTTCCGACCCTGCCGCTTACCGG
ATACCTGTCCGCCTTTCTCCCTTCGGGAAGCGTGGCGCTTTCTCAATGCTCACGCTGTAGGTATCTCAGTTCGGTGT
AGGTCGTTCGCTCCAAGCTGGGCTGTGTGCACGAACCCCCGTTCAGCCCGACCGCTGCGCCTTATCCGGTAACT
ATCGTCTTGAGTCCAACCCGGTAAGACACGACTTATCGCCACTGGCAGCAGCCACTGGTAACAGGATTAGCAGAG
CGAGGTATGTAGGCGGTGCTACAGAGTTCTTGAAGTGGTGGCCTAACTACGGCTACACTAGAAGGACAGTATTT
GGTATCTGCGCTCTGCTGAAGCCAGTTACCTTCGGAAAAAGAGTTGGTAGCTCTTGATCCGGCAAACAAACCACC
GCTGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGCATGCGCTAAGCGGGCTT
TATAAAACGGGCTGCGGGACCAGTTTTCATATCACTACCGTTTGAGTTCTTGTGCTGTGTGGATACTCCTCCCGAC
ACCGAAT

SEQ ID NO: 14: pExpreS2-1 vector expressing PfRiprFL
CGTAAGTATCAAGGTTACAAGACAGGTTTAAGGAGACCAATAGAAACTGGGCTTGTCGAGACAGAGAAGACTCT
TGCGTTTCTGATAGGCACCTATTGGTCTTACTGACATCCACTTTGCCTTTCTCTCCACAGGAATTCGCCACCATGAA
GCTGTGCATCCTGCTGGCCGTGGTGGCCTTCGTGGGACTGAGCCTGGGCATCGATCTGATCGAGGGCATCTTCTA
CGAGAAGAACGAGATCGACAAGCTGACCTTCAGCCTGGATCACCGCGTGCGCGATAACCTGAAGACCGACCTGA
TCCTGAACAACAACGGCGAGAACGATTACGCCTACCTGAACAAATACGTGTACACCATCCTGAACCGCGACAGCA
CCGAGAAGATCAAGACCTTCTTCAGCCACAACAAGGACATGAAGTCCTGCGACTACTTCATCAGCAAGGAGTACA
ACAGCAGCGACAAGACCAACCAGATCTGCTACAAGAAGACGTTCTGCGGCGTCGTGATCCCCAACAGCGAGGAG
ATTAAGACGAACAAGATCACCAACGATAAGCTGTACTGCGCCCACTTCAACAGCACCCACATCATCATCTACTACA
TCAGCCAGCCCCTGCTGCTGGAGCCCCACGTGGTGTACGAGGAGACCTTTTTCGAGAAGGGCAAGAACGACCAG
ATCAACTGCCAGGGCATGTACATCTCCCTGCGCTCCGTGCATGTGCACACCCACAACGCCATCCTGCAGCAGGAG
ACCCTGACCTACATCAAGAACCTGTGCGACGGCAAGAACAACTGCAAGTTCGACTTCGACAGCATTAAGTACGAG
AACAAGAGCCTGACCCACTACCTGTTCTTCATCAACATCCAGTACCAGTGCATCAGCCCCCTGAACCTGCAGGAGA
ATGAGATGTGCGACGTGTACAACGACGATACGCACAAGGCCACGTGCAAATACGGCTTCAACAAGATCGAGCTG
CTGAAGAATGTGTGCGAGGAGAACTACCGCTGCACCCAGGATATCTGCAGCGTGAACCAGTTCTGCGACGGCGA
GAATGAGACCTGCACGTGCAAGACCAGCCTGCTGCCCAGCGCCAAGAACAATTGCGAGTACAACGATCTGTGCA
CCGTGCTGAACTGCCCCGAGAACTCGACCTGCGAGCAGATCGGCAATGGCAAGAAGGCCGAGTGCAAGTGCGA
GAACGGCAAGTACTACCACAACAACAAGTGCTACACCAAGAACGATCTGGAGCTGGCCATCAAGATTGAGCCCC
ACAAGAAGGAGAAGTTCTATAAGAACAACCTGTACCAGGGCAAGGCCCTGAAGCCCGAGTACATCTTCATGCAG
TGCGAGAATGGCTTCAGCATCGAAGTGATCAACGCCTACGTGTCCTGCTACCGCGTGTCCTTCAATCTGAACAAG
CTGAAATACGTGACCGAGAGCCTGAAGAAGATGTGCGACGGAAAGACCAAGTGCGCCTACGGCAACACCATCGA
TCCCATCGATGATCTGAACCACCACAACATCTGCAACAACTTCAACACGATCTTTAAGTATGACTACCTGTGCGTG
TTCAACAACCAGAACATCACCTCCGACAAGAACAGCCATCTGCACAGCAACATCCCCAGCCTGTACAACTCCAGCA

```
TCCTGCCCGATATCAACAAGAGCAAGTTCCACCTGATCAGCCGCAACAGCCGCACCAACCAGTACCCCCACAACA
ATATCAGTATGCTGGAGATCCAGAATGAGATCAGCAGCCACAACTCCAACCAGTTCTCCACCGATCCCCACACCAA
CTCGAACAACATCAACAACATGAATATCAAGAAGGTGGAGATCTTCCGCAGCCGCTTCAGCTCCAAGCTGCAGTG
CCAGGGCGGCAAGATCAACATCGACAAGGCCATTCTGAAGGGCGGCGAGGGCTGCAATGATCTGCTGCTGACCA
ACAGCCTGAAGTCCTACTGCAACGACCTGAGCGAGTGCGATATCGGCCTGATCTACCACTTCGATACCTACTGCAT
CAATGACCAGTACCTGTTCGTGTCCTACAGCTGCAGCAACCTGTGCAACAAGTGCCACAACAACTCCACGTGCTAC
GGCAACCGCTTCAACTACGATTGCTTCTGCGATAACCCCTACATCTCGAAGTACGGAAACAAGCTGTGCGAGCGC
CCCAACGATTGCGAGAGCGTGCTGTGCTCCCAGAACCAAGTGTGCCAGATCCTGCCGAATGATAAGCTGATCTGC
CAGTGCGAGGAGGGCTACAAGAACGTGAAGGGAAAATGCGTGCCGGATAACAAGTGCGATCTGAGCTGCCCCA
GCAACAAAGTGTGCGTGATCGAGAATGGAAAGCAGACCTGCAAGTGCTCCGAGCGCTTCGTGCTGGAGAACGG
CGTGTGCATCTGCGCCAACGATTACAAGATGGAGGATGGCATCAACTGCATTGCCAAGAACAAGTGCAAGCGCA
AGGAGTACGAGAATATCTGCACCAACCCCAACGAGATGTGCGCCTACAATGAGGAGACCGATATCGTGAAGTGC
GAGTGCAAGGAGCACTACTACCGCAGCAGCCGCGGAGAGTGCATTCTGAACGACTACTGCAAGGACATCAATTG
CAAGGAGAACGAGGAGTGCAGCATCGTGAACTTCAAGCCAGAGTGCGTGTGCAAGGAGAACCTGAAGAAGAAC
AACAAGGGCGAGTGCATCTACGAGAACAGCTGCCTGATCAACGAGGGCAACTGCCCCAAGGATAGCAAGTGCAT
CTATCGCGAGTACAAGCCCCACGAGTGCGTGTGCAACAAGCAGGGACACGTGGCCGTGAATGGCAAATGCGTGC
TGGAGGATAAGTGCGTGCACAACAAGAAGTGCAGCGAGAACAGCATCTGCGTGAACGTGATGAACAAGGAGCC
AATCTGCGTGTGCACCTACAACTACTACAAGAAGGACGGCGTGTGCCTGATCCAGAACCCCTGCCTGAAGGATAA
CGGCGGCTGCTCCCGCAACTCCGAGTGCACCTTCAAGTACAGCAAGATCAACTGCACGTGCAAGGAGAACTACA
AGAACAAGGATGATAGCTGCGTGCCCAACACGAACGAGTACGATGAGAGCTTCACCTTCCAGTATAACGACGAC
GCCAGCATCATCCTGGGCGCCTGCGGCATGATCGAGTTCAGCTACATCTACAACCAGATTATCTGGAAGATTAAC
AACTCGAAGGAGTCCTACGTGTTCTACTACGATTACCCCACCGCCGGCAACATCGAGGTGCAGATTAAGAATGAG
ATTTTCCACACGATCATCTATCTGAAGAAGAAGATCGGCAACAGCGTGATCTACGACGATTTCCAGGTGGACCAC
CAGACCTGCATCTATGAGAATGTGTTTTACTACAGCAACCAGAATAGCGCCTGGTCCCACCCCCAGTTCGAGAAAT
GAGCGGCCGCGGATCGATCGATATCTGACTAAATCTTAGTTTGTATTGTCATGTTTTAATACAATATGTTATGTTTA
AATATGTTTTTAATAAATTTTATAAAATAATTTCAACTTTTATTGTAACAACATTGTCCATTTACACACTCCTTTCAA
GCGCGTGGGACTCGATGCTCGGCGCCACTCAAAGGCGGTAATACGGTTATCCACAGAATCAGGGGATAACGCAG
GAAAGAACATGTGAGCAAAAGGCCAGCAAAAGGCCAGGAACCGTAAAAAGGCCGCGTTGCTGGCGTTTTTCCAT
AGGCTCCGCCCCCTGACGAGCATCACAAAAATCGACGCTCAAGTCAGAGGTGGCGAAACCCGACAGGACTATA
AAGATACCAGGCGTTTCCCCCTGGAAGCTCCCTCGTGCGCTCTCCTGTTCCGACCCTGCCGCTTACCGGATACCTG
TCCGCCTTTCTCCCTTCGGGAAGCGTGGCGCTTTCTCAATGCTCACGCTGTAGGTATCTCAGTTCGGTGTAGGTCG
TTCGCTCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGAGGT
ATGTAGGCGGTGCTACAGAGTTCTTGAAGTGGTGGCCTAACTACGGCTACACTAGAAGGACAGTATTTGGTATCT
GCGCTCTGCTGAAGCCAGTTACCTTCGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGATCTCAAGAAGATCCTTTGATCTTTTC
TACGGGGTCTGACGCTCAGTGGAACGAAAACTCACGTTAAGGGATTTTGCATGCGCTAAGCGGGCTTTATAAAAC
GGGCTGCGGGACCAGTTTTCATATCACTACCGTTTGAGTTCTTGTGCTGTGTGGATACTCCTCCCGACACCGAATT
AATTCGGATCTCTGCAAGGGATTTTGGTCATGAACAATAAAACTGTCTGCTTACATAAACAGTAATACAAGGGGT
GTTCATAGTATAATACGACTCACTATAGGAGGGCCACCATGGCCAAGTTGACCAGTGCCGTTCCGGTGCTCACCG
CGCGCGACGTCGCCGGAGCGGTCGAGTTCTGGACCGACCGGCTCGGGTTCAGCCGGGACTTCGTGGAGGACGA
CTTCGCCGGTGTGGTCCGGGACGACGTGACCCTGTTCATCAGCGCGGTCCAGGACCAGGTGGTGCCGGACAACA
CCCTGGCCTGGGTGTGGGTGCGCGGCCTGGACGAGCTGTACGCCGAGTGGTCGGAGGTCGTGTCCACGAACTTC
CGGGACGCCTCCGGGCCGGCCATGACCGAGATCGGCGAGCAGCCGTGGGGGCGGGAGTTCGCCCTGCGCGACC
CGGCCGGCAACTGCGTGCACTTCGTGGCCGAGGAGCAGGACTGACCGACGCCGACCAACACCGCCGGTCCGACG
GCGGCCCACGGGTCCCAGGGGGTCGACCTCGAAACTTGTTTATTGCAGCTTATAATGGTTACAAATAAAGCAAT
AGCATCACAAATTTCACAAATAAAGCATTTTTTTCACTGCATTCTAGTTGTGGTTTGTCCAAACTCATCAATGTATCT
TATCATGTCTTCACGTAATAAGTGTGCGGCTAGCAGTCAACTACTAGTGAATGCCCTACTAGAAGATGTGTGTTGC
ACAAAATGTCCCTGGAATAACCAATTTGAAGTGCAGATAGCAGTAAACGTAAGCTAATATGAATATTATTTAACTG
TAATGTTTTAATATCGCTGGACATTACTAATAAACCCACTATAAACACATGTACATATGTATGTTTTGGCATACAAT
GAGTAGTTGGGGAAAAAATGTGTAAAAGCACCGTGACCATCACAGCATAAAGATAACCAGCTGAAGTATCGAAT
ATGAGTAACCCCCAAATTGAATCACATGCCGCAACTGATAGGACCCATGGAAGTACACTCTTCATGGCGATATAC
AAGACACACACAAGCACGAACACCCAGTTGCGGAGGAAATTCTCCGTAAATGAAAACCCAATCGGCGAACAATT
```

Figure 3G

CATACCCATATATGGTAAAAGTTTTGAACGCGAGCGAACTTAAGAGCGCCGGAGTATAAATAGAGGCGCTTCGTC
TACGGAGCGACAATTCAATTCAAACAAGCAAAGTGAACACGTCGCTAAGCGAAAGCTAAGCAAATAAACAAGCG
CAGCTGAACAAGCTAAACAATCTGCAGAAGCTTGGTACCCTCGAGCT

SEQ ID NO: 15: pExpreS2-2 vector expressing PfRh5 version 1

AATTCGGATCTCTGCAAGGGATTTTGGTCATGAACAATAAAACTGTCTGCTTACATAAACAGTAATACAAGGGGT
GTTCATAGTATAATACGACTCACTATAGGAGGGCCACCATGAGCCACATCCAGCGCGAAACCAGCTGCAGCCGTC
CGCGCCTGAACAGCAACATGGATGCCGATCTGTACGGCTACAAATGGGCCCGCGATAACGTGGGCCAGAGCGGC
GCTACCATCTACCGCCTGTACGGCAAACCGGATGCCCCGGAACTGTTCCTGAAACACGGCAAAGGCAGCGTGGC
CAACGATGTGACCGATGAAATGGTGCGCCTGAACTGGCTGACCGAGTTCATGCCGCTGCCGACCATCAAACACTT
CATCCGCACCCCGGATGATGCCTGGCTGCTGACCACCGCCATTCCGGGCAAAACCGCCTTCCAGGTGCTGGAAGA
ATACCCGGATAGCGGCGAAAACATCGTGGATGCCCTGGCCGTGTTCCTGCGCCGCCTGCACAGCATCCCGGTGTG
CAACTGCCCGTTCAACAGCGATCGCGTGTTCCGCCTGGCTCAGGCCCAGAGCCGCATGAACAACGGCCTGGTGG
ATGCCAGCGATTTCGATGATGAACGCAACGGCTGGCCGGTGGAACAGGTGTGGAAAGAGATGCACAAACTGCT
GCCGTTCAGCCCGGATTCCGTGGTGACCCACGGCGATTTCAGCCTGGATAACCTGATCTTCGATGAGGGCAAACT
GATCGGCTGCATCGATGTGGGCCGCGTGGGCATTGCCGATCGCTACCAGGATCTGGCCATCCTGTGGAACTGCCT
GGGCGAGTTCAGCCCGAGCCTGCAGAAACGCCTGTTCCAGAAGTACGGCATCGATAACCCGGATATGAACAAAC
TGCAGTTCCACCTGATGCTGGATGAGTTCTTCTAATAAGTCGACCTCGAAACTTGTTTATTGCAGCTTATAATGGTT
ACAAATAAAGCAATAGCATCACAAATTTCACAAATAAAGCATTTTTTTCACTGCATTCTAGTTGTGGTTTGTCCAAA
CTCATCAATGTATCTTATCATGTCTTCACGTAATAAGTGTGCGGCTAGCAGTCAACTACTAGTGAATGCCCTACTA
GAAGATGTGTGTTGCACAAAATGTCCCTGGAATAACCAATTTGAAGTGCAGATAGCAGTAAACGTAAGCTAATAT
GAATATTATTTAACTGTAATGTTTTAATATCGCTGGACATTACTAATAAACCCACTATAAACACATGTACATATGTA
TGTTTTGGCATACAATGAGTAGTTGGGGAAAAAATGTGTAAAAGCACCGTGACCATCACAGCATAAAGATAACCA
GCTGAAGTATCGAATATGAGTAACCCCCAAATTGAATCACATGCCGCAACTGATAGGACCCATGGAAGTACACTC
TTCATGGCGATATACAAGACACACACAAGCACGAACACCCAGTTGCGGAGGAAATTCTCCGTAAATGAAAACCCA
ATCGGCGAACAATTCATACCCATATATGGTAAAAGTTTTGAACGCGAGCGAACTTAAGAGCGCCGGAGTATAAAT
AGAGGCGCTTCGTCTACGGAGCGACAATTCAATTCAAACAAGCAAAGTGAACACGTCGCTAAGCGAAAGCTAAG
CAAATAAACAAGCGCAGCTGAACAAGCTAAACAATCTGCAGAAGCTTGGTACCCTCGAGCTCAGCTGAATTCGCC
ACCATGAAGCTGTGCATCCTGCTGGCCGTGGTGGCCTTCGTGGGACTGAGTCTGGGCGACGTGAAGAACAACGA
GGACTACAAGAACGTGGACTATAAGAATGTGAACTTCCTGCAGTACCACTTCAAGGAGCTGAGCAACTACAATAT
CGCCAACAGCATCGACATTCTGCAGGAGAAGGAGGGCCACCTGGATTTCGTGATCATCCCCACTACACCTTTCT
GGACTACTACAAGCACCTGAGCTACAACTCCATCTACCACAAGAGCAGCACCTACGGCAAGTGCATTGCCGTGGA
TGCCTTCATCAAGAAGATCAACGAGACCTACGACAAAGTGAAGTCCAAGTGCAACGACATCAAGAACGACCTGAT
CGCCACGATCAAGAAGCTGGAGCACCCCTACGATATCAACAACAAGAACGATGACAGCTACCGCTACGACATCA
GCGAGGAGATCGACGATAAGTCCGAGGAGACGGACGACGAGACCGAGGAGGTGGAGGATAGCATCCAGGATA
CCGATAGCAACCACACCCCCAGCAACAAGAAGAAGAATGATCTGATGAACCGCACCTTTAAGAAGATGATGGAC
GAGTACAATACGAAAAAGAAGAAGCTGATCAAGTGCATCAAGAATCACGAGAACGACTTCAACAAGATCTGCAT
GGACATGAAGAACTACGGCACCAACCTGTTCGAGCAGCTGTCCTGCTACAACAACAACTTCTGCAACACCAACGG
CATCCGCTACCACTACGATGAGTACATCCACAAGCTGATCCTGAGCGTGAAGTCGAAGAACCTGAACAAGGATCT
GAGCGACATGACCAACATCCTGCAGCAGAGCGAGCTGCTGCTGACCAATCTGAACAAGAAGATGGGCAGCTACA
TCTACATCGACACCATCAAGTTCATTCACAAGGAGATGAAGCACATCTTCAACCGCATCGAGTACCACACCAAGAT
CATCAACGACAAGACGAAGATCATTCAGGACAAGATCAAGCTGAACATCTGGCGCACCTTCCAGAAGGATGAGC
TGCTGAAGCGCATCCTGGATATGAGCAACGAGTACAGCCTGTTCATCACCAGCGATCATCTGCGCCAGATGCTGT
ACAACACCTTCTACAGCAAGGAGAAGCACCTGAACAACATCTTCCACCACCTGATCTACGTGCTGCAGATGAAGTT
CAACGACGTGCCCATCAAGATGGAGTACTTCCAGACCTATAAGAAGAACAAGCCCCTGACCCAGCACCACCATCA
CCACCACAAGCGCCGCTGGAAGAAGAACTTTATCGCCGTGTCCGCCGCCAACCGCTTCAAGAAGATTAGCAGCAG
CGGAGCCCTGTAGGCGGCCGCGGATCGATCGATATCTGACTAAATCTTAGTTTGTATTGTCATGTTTTAATACAAT
ATGTTATGTTTAAATATGTTTTTAATAAATTTTATAAAATAATTTCAACTTTTATTGTAACAACATTGTCCATTTACAC
ACTCCTTTCAAGCGCGTGGGACTCGATGCTCGGCGCCACTCAAAGGCGGTAATACGGTTATCCACAGAATCAGGG
GATAACGCAGGAAAGAACATGTGAGCAAAAGGCCAGCAAAAGGCCAGGAACCGTAAAAAGGCCGCGTTGCTGG
CGTTTTTCCATAGGCTCCGCCCCCTGACGAGCATCACAAAAATCGACGCTCAAGTCAGAGGTGGCGAAACCCGA
CAGGACTATAAAGATACCAGGCGTTTCCCCCTGGAAGCTCCCTCGTGCGCTCTCCTGTTCCGACCCTGCCGCTTAC
CGGATACCTGTCCGCCTTTCTCCCTTCGGGAAGCGTGGCGCTTTCTCAATGCTCACGCTGTAGGTATCTCAGTTCG

Figure 3H

GTGTAGGTCGTTCGCTCCAAGCTGGGCTGTGTGCACGAACCCCCGTTCAGCCCGACCGCTGCGCCTTATCCGGT
AACTATCGTCTTGAGTCCAACCCGGTAAGACACGACTTATCGCCACTGGCAGCAGCCACTGGTAACAGGATTAGC
AGAGCGAGGTATGTAGGCGGTGCTACAGAGTTCTTGAAGTGGTGGCCTAACTACGGCTACACTAGAAGGACAGT
ATTTGGTATCTGCGCTCTGCTGAAGCCAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGCAGAAAAAAAGGATCTCAAGAAGATCC
TTTGATCTTTTCTACGGGGTCTGACGCTCAGTGGAACGAAAACTCACGTTAAGGGATTTTGCATGCGCTAAGCGG
GCTTTATAAAACGGGCTGCGGGACCAGTTTTCATATCACTACCGTTTGAGTTCTTGTGCTGTGTGGATACTCCTCC
CGACACCGAATT

SEQ ID NO: 16: pExpreS2-PAC vector expressing PfCyrPa
TAATTCGGATCTCTGCAAGGGATTTTGGTCATGAACAATAAAACTGTCTGCTTACATAAACAGTAATACAAGGGG
TGTTCATAGTATAATACGACTCACTATAGGAGGGCCACCATGACCGAGTACAAGCCCACCGTGCGCCTGGCCACC
CGCGACGATGTGCCACGCGCCGTGCGCACCCTGGCCGCCGCCTTTGCCGATTATCCAGCCACCCGCCATACCGTG
GACCCCGATCGCCATATTGAGCGCGTGACCGAGCTGCAGGAGCTGTTCCTGACCCGCGTGGGCCTGGATATTGG
CAAAGTGTGGGTGGCCGATGACGGAGCCGCCGTGGCCGTGTGGACCACCCCAGAGAGTGTGGAGGCCGGAGCC
GTGTTCGCCGAGATTGGACCACGCATGGCCGAGCTGAGTGGAAGTCGCCTGGCCGCCCAGCAGCAGATGGAGG
GACTGCTGGCCCCACACCGCCCAAAGGAGCCAGCCTGGTTTCTGGCCACCGTGGGAGTGTCCCCAGATCACCAG
GGAAAGGGACTGGGAAGTGCCGTGGTGCTGCCAGGCGTGGAGGCCGCCGAGCGCGCCGGCGTGCCAGCCTTTC
TGGAGACCAGTGCCCCACGCAACCTGCCCTTTTACGAGCGCCTGGGCTTTACCGTGACCGCCGATGTGGAGGTGC
CAGAGGGCCCACGCACCTGGTGCATGACCCGCAAGCCAGGCGCCTAAGTCGACCTCGAAACTTGTTTATTGCAGC
TTATAATGGTTACAAATAAAGCAATAGCATCACAAATTTCACAAATAAAGCATTTTTTTCACTGCATTCTAGTTGTG
GTTTGTCCAAACTCATCAATGTATCTTATCATGTCTTCACGTAATAAGTGTGCGGTAGCAGTCAACTACTAGTGA
ATGCCCTACTAGAAGATGTGTGTTGCACAAAATGTCCCTGGAATAACCAATTTGAAGTGCAGATAGCAGTAAACG
TAAGCTAATATGAATATTATTTAACTGTAATGTTTTAATATCGCTGGACATTACTAATAAACCCACTATAAACACAT
GTACATATGTATGTTTTGGCATACAATGAGTAGTTGGGGAAAAAATGTGTAAAAGCACCGTGACCATCACAGCAT
AAAGATAACCAGCTGAAGTATCGAATATGAGTAACCCCCAAATTGAATCACATGCCGCAACTGATAGGACCCATG
GAAGTACACTCTTCATGGCGATATACAAGACACACACAAGCACGAACACCCAGTTGCGGAGGAAATTCTCCGTAA
ATGAAAACCCAATCGGCGAACAATTCATACCCATATATGGTAAAAGTTTTGAACGCGAGCGAACTTAAGAGCGCC
GGAGTATAAATAGAGGCGCTTCGTCTACGGAGCGACAATTCAATTCAAACAAGCAAAGTGAACACGTCGCTAAG
CGAAAGCTAAGCAAATAAACAAGCGCAGCTGAACAAGCTAAACAATCTGCAGAAGCTTGGTACCCTCGAGCTCG
TAAGTATCAAGGTTACAAGACAGGTTTAAGGAGACCAATAGAAACTGGGCTTGTCGAGACAGAGAAGACTCTTG
CGTTTCTGATAGGCACCTATTGGTCTTACTGACATCCACTTTGCCTTTCTCTCCACAGGAATTCGCCACCATGAAGC
TGTGCATCCTGCTGGCCGTGGTGGCCTTCGTGGGACTGAGTCTGGGAAGCCGCCACGTGTTCATCCGCACCGAGC
TGAGCTTCATCAAGAACAACGTGCCCTGCATCCGCGACATGTTCTTCATCTACAAGCGCGAGCTGTACAACATCTG
CCTGGATGATCTGAAGGGCGAGGAGGATGAGACCCACATCTACGTGCAGAAGAAAGTGAAGGACAGCTGGATC
ACCCTGAACGACCTGTTCAAGGAGACCGATCTGACCGGACGCCCCCACATCTTCGCCTACGTGGACGTGGAGGA
GATCATCATTCTGCTGTGCGAGGATGAGGAGTTCAGCAACCGCAAGAAGGATATGACCTGCCACCGCTTCTACAG
CAACGATGGCAAGGAGTACAACAACAGCGAGATCACCATCAGCGACTACATCCTGAAGGATAAGCTGCTGTCCA
GCTACGTGTCCCTGCCCCTGAAGATCGAGAACCGCGAGTACTTCCTGATCTGCGGCGTGTCCCCCTACAAGTTCAA
GGATGATAACAAGAAGGACGACATCCTGTGCATGGCCAGCCACGATAAGGGCGAGACCTGGGGCACCAAGATC
GTGATTAAGTACGACAACTACAAGCTGGGCGTGCAGTACTTCTTCCTGCGCCCCTACATCAGCAAGAACGATCTG
AGCTTCCACTTCTACGTGGGCGACAACATCAACAACGTGAAGAACGTGAACTTCATCGAGTGCACCCACGAGAAG
GATCTGGAGTTCGTGTGCTCCAACCGCGATTTTCTGAAGGACAACAAGGTGCTGCAGGATGTGTCCACCCTGAAT
GATGAGTACATCGTGTCCTACGGCAACGACAACAACTTCGCCGAGTGCTACATCTTCTTCAACAACGAGAACAGC
ATCCTGATCAAGCCCGAGAAGTACGGCAACACCACCGCCGGATGCTACGGCGGCACCTTCGTGAAGATTGATGA
GAACCGCACCCTGTTCATCTACTCCAGCAGCCAGGGCATCTACAACATCCACACCATCTACTACGCCAACTACGAG
CACCACCACCATCACCACTAAGCGGCCGCGGATCGATCGATATCTGACTAAATCTTAGTTTGTATTGTCATGTTTTA
ATACAATATGTTATGTTTAAATATGTTTTTAATAAATTTTATAAAATAATTTCAACTTTTATTGTAACAACATTGTCC
ATTTACACACTCCTTTCAAGCGCGTGGGACTCGATGCTCGGCGCCACTCAAAGGCGGTAATACGGTTATCCACAG
AATCAGGGGATAACGCAGGAAAGAACATGTGAGCAAAAGGCCAGCAAAAGGCCAGGAACCGTAAAAAGGCCG
CGTTGCTGGCGTTTTTCCATAGGCTCCGCCCCCCTGACGAGCATCACAAAAATCGACGCTCAAGTCAGAGGTGGC
GAAACCCGACAGGACTATAAAGATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTCAATGCTCACGCTGTAGGTAT

Figure 3I

CTCAGTTCGGTGTAGGTCGTTCGCTCCAAGCTGGGCTGTGTGCACGAACCCCCCGTTCAGCCCGACCGCTGCGCC
TTATCCGGTAACTATCGTCTTGAGTCCAACCCGGTAAGACACGACTTATCGCCACTGGCAGCAGCCACTGGTAACA
GGATTAGCAGAGCGAGGTATGTAGGCGGTGCTACAGAGTTCTTGAAGTGGTGGCCTAACTACGGCTACACTAGA
AGGACAGTATTTGGTATCTGCGCTCTGCTGAAGCCAGTTACCTTCGGAAAAAGAGTTGGTAGCTCTTGATCCGGC
AAACAAACCACCGCTGGTAGCGGTGGTTTTTTTGTTTGCAAGCAGCAGATTACGCGCAGAAAAAAAGGATCTCAA
GAAGATCCTTTGATCTTTTCTACGGGGTCTGACGCTCAGTGGAACGAAAACTCACGTTAAGGGATTTTGCATGCG
CTAAGCGGGCTTTATAAAACGGGCTGCGGGACCAGTTTTCATATCACTACCGTTTGAGTTCTTGTGCTGTGTGGAT
ACTCCTCCCGACACCGAAT

SEQ ID NO: 17: pExpreS2-1 vector expressing PfEBA175
CGTAAGTATCAAGGTTACAAGACAGGTTTAAGGAGACCAATAGAAACTGGGCTTGTCGAGACAGAGAAGACTCT
TGCGTTTCTGATAGGCACCTATTGGTCTTACTGACATCCACTTTGCCTTTCTCTCCACAGGAATTCGCCACCATGAA
GCTGTGCATCCTGCTGGCCGTGGTGGCCTTCGTGGGACTGAGTCTGGGACAGGAGGCCGTGCCAGAGGAGAGC
ACCGAGATTGCCCACCGCACCGAGACCCGCACCGATGAGCGCAAGAATCAGGAGCCCGCCAACAAGGATCTGAA
GAACCCCCAGCAGAGCGTGGGCGAGAACGGCACGAAGGATCTGCTGCAGGAGGATCTGGGAGGCAGCCGCAG
CGAGGATGAAGTGACCCAGGAGTTCGGCGTGAACCACGGCATCCCCAAGGGCGAGGATCAGACCCTGGGAAAG
TCCGATGCCATCCCCAACATCGGCGAGCCCGAGACCGGAATCAGTACCACCGAGGAGTCCCGCCACGAGGAGGG
CCATAACAAGCAGGCCCTGAGCACCTCCGTGGATGAGCCCGAGCTGAGCGATACCCTGCAGCTGCACGAGGATA
CCAAGGAGAACGATAAGCTGCCCCTGGAGAGCAGCACCATCACCAGCCCAACCGAGAGCGGCAGCAGCGATACC
GAGGAGACCCCATCCATTAGCGAGGGCCCGAAGGGCAACGAGCAGAAGAAGCGCGACGACGATAGCCTGAGCA
AGATCAGCGTGTCCCCCGAGAACAGCCGCCCAGAGACCGATGCCAAGGATACCAGCAACCTGCTGAAGCTGAAG
GGCGACGTGGACATCAGCATGCCCAAGGCCGTGATCGGCAGCTCCCCCAACGATAACATCAACGTGACCGAGCA
GGGCGACAACATCTCGGGCGTGAACAGCAAGCCCCTGTCCGATGATGTGCGCCCCGATAAGAACCATGAGGAAG
TGAAGGAGCACACCAGCAACAGCGATAACGTGCAGCAGTCCGGCGGCATCGTGAACATGAACGTGGAGAAGGA
GCTGAAGGACACCCTGGAGAACCCCAGCTCCAGCCTGGATGAGGGAAAGGCCCATGAGGAGCTGTCCGAGCCC
AACCTGTCCAGCGATCAGGATATGAGCAACACCCCAGGCCCCCTGGATAACACCTCGGAGGAGACGACCGAGCG
CATCAGCAACAACGAGTACAAAGTGAACGAGCGCGAGGGCGAGCGCACCCTGACCAAGGAGTATGAGGATATC
GTGCTGAAGTCCCACATGAACCGCGAGAGCGACGATGGCGAGCTGTACGATGAGAACAGCGATCTGAGCACCGT
GAACGATGAGTCCGAGGATGCCGAGGCCAAGATGAAGGGCAATGATACCAGCGAGATGAGCCACAACAGCAGC
CAGCACATCGAGAGCGATCAGCAGAAGAACGATATGAAGACCGTGGGCGACCTGGGCACCACCCACGTGCAGA
ATGAGATCTCCGTGCCCGTGACCGGCGAGATCGATGAGAAGCTGCGCGAGAGCAAGGAGTCCAAGATCCACAA
GGCCGAGGAGGAGCGCCTGAGCCACACCGATATCCACAAGATCAACCCCGAGGATCGCAACTCCAACACCCTGC
ACCTGAAGGATATCCGCAACGAGGAGAATGAGCGCCACCTGACGAACCAGAACATCAACATCAGCCAGGAGCGC
GACCTGCAGAAGCACGGCTTCCACACCATGAACAACCTGCACGGCGACGGCGTGTCCGAGCGCAGCCAGATCAA
TCACTCGCACCACGGCAACCGCCAGGATCGCGGAGGAAATAGTGGAAGCGCCTGGTCCCACCCCCAGTTCGAGA
AATGAGCGGCCGCGGATCGATCGATATCTGACTAAATCTTAGTTTGTATTGTCATGTTTTAATACAATATGTTATG
TTTAAATATGTTTTTAATAAATTTTATAAAATAATTTCAACTTTTATTGTAACAACATTGTCCATTTACACACTCCTTT
CAAGCGCGTGGGACTCGATGCTCGGCGCCACTCAAAGGCGGTAATACGGTTATCCACAGAATCAGGGGATAACG
CAGGAAAGAACATGTGAGCAAAAGGCCAGCAAAAGGCCAGGAACCGTAAAAAGGCCGCGTTGCTGGCGTTTTTC
CATAGGCTCCGCCCCCCTGACGAGCATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTGTTCCGACCCTGCCGCTTACCGGATAC
CTGTCCGCCTTTCTCCCTTCGGGAAGCGTGGCGCTTTCTCAATGCTCACGCTGTAGGTATCTCAGTTCGGTGTAGG
TCGTTCGCTCCAAGCTGGGCTGTGTGCACGAACCCCCCGTTCAGCCCGACCGCTGCGCCTTATCCGGTAACTATCG
TCTTGAGTCCAACCCGGTAAGACACGACTTATCGCCACTGGCAGCAGCCACTGGTAACAGGATTAGCAGAGCGA
GGTATGTAGGCGGTGCTACAGAGTTCTTGAAGTGGTGGCCTAACTACGGCTACACTAGAAGGACAGTATTTGGT
ATCTGCGCTCTGCTGAAGCCAGTTACCTTCGGAAAAAGAGTTGGTAGCTCTTGATCCGGCAAACAAACCACCGCT
GGTAGCGGTGGTTTTTTTGTTTGCAAGCAGCAGATTACGCGCAGAAAAAAAGGATCTCAAGAAGATCCTTTGATC
TTTTCTACGGGGTCTGACGCTCAGTGGAACGAAAACTCACGTTAAGGGATTTTGCATGCGCTAAGCGGGCTTTAT
AAAACGGGCTGCGGGACCAGTTTTCATATCACTACCGTTTGAGTTCTTGTGCTGTGTGGATACTCCTCCCGACACC
GAATTAATTCGGATCTCTGCAAGGGATTTTGGTCATGAACAATAAAACTGTCTGCTTACATAAACAGTAATACAAG
GGGTGTTCATAGTATAATACGACTCACTATAGGAGGGCCACCATGGCCAAGTTGACCAGTGCCGTTCCGGTGCTC
ACCGCGCGCGACGTCGCCGGAGCGGTCGAGTTCTGGACCGACCGGCTCGGGTTCAGCCGGGACTTCGTGGAGG

Figure 3J

ACGACTTCGCCGGTGTGGTCCGGGACGACGTGACCCTGTTCATCAGCGCGGTCCAGGACCAGGTGGTGCCGGAC
AACACCCTGGCCTGGGTGTGGGTGCGCGGCCTGGACGAGCTGTACGCCGAGTGGTCGGAGGTCGTGTCCACGA
ACTTCCGGGACGCCTCCGGGCCGGCCATGACCGAGATCGGCGAGCAGCCGTGGGGGCGGGAGTTCGCCCTGCG
CGACCCGGCCGGCAACTGCGTGCACTTCGTGGCCGAGGAGCAGGACTGACCGACGCCGACCAACACCGCCGGTC
CGACGGCGGCCCACGGGTCCCAGGGGGGTCGACCTCGAAACTTGTTTATTGCAGCTTATAATGGTTACAAATAAA
GCAATAGCATCACAAATTTCACAAATAAAGCATTTTTTTCACTGCATTCTAGTTGTGGTTTGTCCAAACTCATCAAT
GTATCTTATCATGTCTTCACGTAATAAGTGTGCGGCTAGCAGTCAACTACTAGTGAATGCCCTACTAGAAGATGTG
TGTTGCACAAAATGTCCCTGGAATAACCAATTTGAAGTGCAGATAGCAGTAAACGTAAGCTAATATGAATATTATT
TAACTGTAATGTTTTAATATCGCTGGACATTACTAATAAACCCACTATAAACACATGTACATATGTATGTTTTGGCA
TACAATGAGTAGTTGGGGAAAAAATGTGTAAAAGCACCGTGACCATCACAGCATAAAGATAACCAGCTGAAGTA
TCGAATATGAGTAACCCCCAAATTGAATCACATGCCGCAACTGATAGGACCCATGGAAGTACACTCTTCATGGCG
ATATACAAGCACACACAAGCACGAACACCCAGTTGCGGAGGAAATTCTCCGTAAATGAAAACCCAATCGGCGA
ACAATTCATACCCATATATGGTAAAAGTTTTGAACGCGAGCGAACTTAAGAGCGCCGGAGTATAAATAGAGGCGC
TTCGTCTACGGAGCGACAATTCAATTCAAACAAGCAAAGTGAACACGTCGCTAAGCGAAAGCTAAGCAAATAAAC
AAGCGCAGCTGAACAAGCTAAACAATCTGCAGAAGCTTGGTACCCTCGAGCT

SEQ ID NO: 27: *Pf*EBA175 amino acid sequence (760-1271 W2MEF)

QEAVPEESTEIAHRTETRTDERKNQEPANKDLKNPQQSVGENGTKDLLQEDLGGSRSEDEVTQEFGVNHGIPKGEDQ
TLGKSDAIPNIGEPETGISTTEESRHEEGHNKQALSTSVDEPELSDTLQLHEDTKENDKLPLESSTITSPTESGSSDTEETPS
ISEGPKGNEQKKRDDDSLSKISVSPENSRPETDAKDTSNLLKLKGDVDISMPKAVIGSSPNDNINVTEQGDNISGVNSKP
LSDDVRPDKNHEEVKEHTSNSDNVQQSGGIVNMNVEKELKDTLENPSSSLDEGKAHEELSEPNLSSDQDMSNTPGPL
DNTSEETTERISNNEYKVNEREGERTLTKEYEDIVLKSHMNRESDDGELYDENSDLSTVNDESEDAEAKMKGNDTSEM
SHNSSQHIESDQQKNDMKTVGDLGTTHVQNEISVPVTGEIDEKLRESKESKIHKAEEERLSHTDIHKINPEDRNSNTLHL
KDIRNEENERHLTNQNINISQERDLQKHGFHTMNNL

Figure 3K

SEQUENCE LISTING

```
<160> NUMBER OF SEQ ID NOS: 27

<210> SEQ ID NO 1
<211> LENGTH: 3207
<212> TYPE: DNA
<213> ORGANISM: Plasmodium falciparum

<400> SEQUENCE: 1
atcgatctga tcgagggcat cttctacgag aagaacgaga tcgacaagct gaccttcagc     60
ctggatcacc gcgtgcgcga taacctgaag accgacctga tcctgaacaa caacggcgag    120
aacgattacg cctacctgaa caaatacgtg tacaccatcc tgaaccgcga cagcaccgag    180
aagatcaaga ccttcttcag ccacaacaag gacatgaagt cctgcgacta cttcatcagc    240
aaggagtaca acagcagcga caagaccaac cagatctgct acaagaagac gttctgcggc    300
gtcgtgatcc ccaacagcga ggagattaag acgaacaaga tcaccaacga taagctgtac    360
tgcgcccact tcaacagcac ccacatcatc atctactaca tcagccagcc cctgctgctg    420
gagccccacg tggtgtacga ggagaccttt ttcgagaagg gcaagaacga ccagatcaac    480
tgccagggca tgtacatctc cctgcgctcc gtgcatgtgc acacccacaa cgccatcctg    540
cagcaggaga ccctgaccta catcaagaac ctgtgcgacg gcaagaacaa ctgcaagttc    600
gacttcgaca gcattaagta cgagaacaag agcctgaccc actacctgtt cttcatcaac    660
atccagtacc agtgcatcag ccccctgaac ctgcaggaga atgagatgtg cgacgtgtac    720
aacgacgata cgcacaaggc cacgtgcaaa tacggcttca acaagatcga gctgctgaag    780
aatgtgtgcg aggagaacta ccgctgcacc caggatatct gcagcgtgaa ccagttctgc    840
gacggcgaga atgagacctg cacgtgcaag accagcctgc tgcccagcgc caagaacaat    900
tgcgagtaca acgatctgtg caccgtgctg aactgccccg agaactcgac ctgcgagcag    960
atcggcaatg gcaagaaggc cgagtgcaag tgcgagaacg gcaagtacta ccacaacaac   1020
aagtgctaca ccaagaacga tctggagctg gccatcaaga ttgagcccca caagaaggag   1080
aagttctata agaacaacct gtaccagggc aaggccctga agcccgagta catcttcatg   1140
cagtgcgaga atggcttcag catcgaagtg atcaacgcct acgtgtcctg ctaccgcgtg   1200
tccttcaatc tgaacaagct gaaatacgtg accgagagcc tgaagaagat gtgcgacgga   1260
aagaccaagt gcgcctacgg caacaccatc gatcccatcg atgatctgaa ccaccacaac   1320
```

```
atctgcaaca acttcaacac gatctttaag tatgactacc tgtgcgtgtt caacaaccag   1380
aacatcacct ccgacaagaa cagccatctg cacagcaaca tccccagcct gtacaactcc   1440
agcatcctgc ccgatatcaa caagagcaag ttccacctga tcagccgcaa cagccgcacc   1500
aaccagtacc cccacaacaa tatcagtatg ctggagatcc agaatgagat cagcagccac   1560
aactccaacc agttctccac cgatccccac accaactcga caacatcaa caacatgaat   1620
atcaagaagg tggagatctt ccgcagccgc ttcagctcca agctgcagtg ccagggcggc   1680
aagatcaaca tcgacaaggc cattctgaag ggcggcgagg gctgcaatga tctgctgctg   1740
accaacagcc tgaagtccta ctgcaacgac ctgagcgagt gcgatatcgg cctgatctac   1800
cacttcgata cctactgcat caatgaccag tacctgttcg tgtcctacag ctgcagcaac   1860
ctgtgcaaca gtgccacaa caactccacg tgctacggca accgcttcaa ctacgattgc   1920
ttctgcgata ccccctacat ctcgaagtac ggaaacaagc tgtgcgagcg ccccaacgat   1980
tgcgagagcg tgctgtgctc ccagaaccaa gtgtgccaga tcctgccgaa tgataagctg   2040
atctgccagt gcgaggaggg ctacaagaac gtgaaggaa aatgcgtgcc ggataacaag   2100
tgcgatctga gctgccccag caacaaagtg tgcgtgatcg agaatggaaa gcagacctgc   2160
aagtgctccg agcgcttcgt gctggagaac ggcgtgtgca tctgcgccaa cgattacaag   2220
atggaggatg gcatcaactg cattgccaag aacaagtgca agcgcaagga gtacgagaat   2280
atctgcacca ccccaacga gatgtgcgcc tacaatgagg agaccgatat cgtgaagtgc   2340
gagtgcaagg agcactacta ccgcagcagc gcgagagt gcattctgaa cgactactgc   2400
aaggacatca attgcaagga gaacgaggag tgcagcatcg tgaacttcaa gccagagtgc   2460
gtgtgcaagg agaacctgaa gaagaacaac aagggcgagt gcatctacga aacagctgc   2520
ctgatcaacg agggcaactg cccccaagga tagcaagtgca tctatcgcga gtacaagccc   2580
cacgagtgcg tgtgcaacaa gcagggacac gtggccgtga atggcaaatg cgtgctggag   2640
gataagtgcg tgcacaacaa gaagtgcagc gagaacagca tctgcgtgaa cgtgatgaac   2700
aaggagccaa tctgcgtgtg cacctacaac tactacaaga aggacggcgt gtgcctgatc   2760
cagaacccct gcctgaagga taacggcggc tgctcccgca actccgagtg caccttcaag   2820
tacagcaaga tcaactgcac gtgcaaggag aactacaaga caaggatga tagctgcgtg   2880
cccaacacga acgagtacga tgagagcttc accttccagt ataacgacga cgccagcatc   2940
atcctgggcg cctgcggcat gatcgagttc agctacatct acaaccagat tatctggaag   3000
attaacaact cgaaggagtc ctacgtgttc tactacgatt accccaccgc cggcaacatc   3060
gaggtgcaga ttaagaatga gatttttccac acgatcatct atctgaagaa gaagatcggc   3120
aacagcgtga tctacgacga tttccaggtg gaccaccaga cctgcatcta tgagaatgtg   3180
ttttactaca gcaaccagaa tagcgcc                                        3207
```

<210> SEQ ID NO 2
<211> LENGTH: 999
<212> TYPE: DNA
<213> ORGANISM: Plasmodium falciparum

<400> SEQUENCE: 2

```
agccgccacg tgttcatccg caccgagctg agcttcatca agaacaacgt gccctgcatc      60
cgcgacatgt tcttcatcta caagcgcgag ctgtacaaca tctgcctgga tgatctgaag     120
ggcgaggagg atgagaccca catctacgtg cagaagaaag tgaaggacag ctggatcacc     180
ctgaacgacc tgttcaagga gaccgatctg accggacgcc cccacatctt cgcctacgtg     240
```

```
gacgtggagg agatcatcat tctgctgtgc gaggatgagg agttcagcaa ccgcaagaag    300
gatatgacct gccaccgctt ctacagcaac gatggcaagg agtacaacaa cagcgagatc    360
accatcagcg actacatcct gaaggataag ctgctgtcca gctacgtgtc cctgcccctg    420
aagatcgaga accgcgagta cttcctgatc tgcggcgtgt cccctacaa gttcaaggat    480 gataacaaga aggacgacat cctgtgcatg gccagccacg ataagggcga gacctggggc    540
accaagatcg tgattaagta cgacaactac aagctgggcg tgcagtactt cttcctgcgc    600
ccctacatca gcaagaacga tctgagcttc cacttctacg tgggcgacaa catcaacaac    660
gtgaagaacg tgaacttcat cgagtgcacc cacgagaagg atctggagtt cgtgtgctcc    720
aaccgcgatt ttctgaagga caacaaggtg ctgcaggatg tgtccaccct gaatgatgag    780
tacatcgtgt cctacggcaa cgacaacaac ttcgccgagt gctacatctt cttcaacaac    840
gagaacagca tcctgatcaa gcccgagaag tacggcaaca ccaccgccgg atgctacggc    900
ggcaccttcg tgaagattga tgagaaccgc accctgttca tctactccag cagccagggc    960
atctacaaca tccacaccat ctactacgcc aactacgag                           999

<210> SEQ ID NO 3
<211> LENGTH: 1200
<212> TYPE: DNA
<213> ORGANISM: Plasmodium falciparum

<400> SEQUENCE: 3
gacgtgaaga caacgagga ctacaagaac gtggactata agaatgtgaa cttcctgcag      60
taccacttca aggagctgag caactacaat atcgccaaca gcatcgacat tctgcaggag    120
aaggagggcc acctggattt cgtgatcatc ccccactaca cctttctgga ctactacaag    180
cacctgagct acaactccat ctaccacaag agcagcacct acggcaagtg cattgccgtg    240
gatgccttca tcaagaagat caacgagacc tacgacaaag tgaagtccaa gtgcaacgac    300
atcaagaacg acctgatcgc cacgatcaag aagctggagc accctacga tatcaacaac    360 aagaacgatg acagctaccg ctacgacatc agcgaggaga tcgacgataa gtccgaggag    420
acggacgacg agaccgagga ggtggaggat agcatccagg ataccgatag caaccacacc    480
cccagcaaca agaagaagaa tgatctgatg aaccgcacct ttaagaagat gatggacgag    540
tacaatacga aaagaagaa gctgatcaag tgcatcaaga atcacgagaa cgacttcaac    600
aagatctgca tggacatgaa gaactacggc accaacctgt tcgagcagct gtcctgctac    660
aacaacaact tctgcaacac caacggcatc cgctaccact acgatgagta catccacaag    720
ctgatcctga gcgtgaagtc gaagaacctg aacaaggatc tgagcgacat gaccaacatc    780
ctgcagcaga gcgagctgct gctgaccaat ctgaacaaga agatgggcag ctacatctac    840
atcgacacca tcaagttcat tcacaaggag atgaagcaca tcttcaaccg catcgagtac    900
cacaccaaga tcatcaacga caagacgaag atcattcagg acaagatcaa gctgaacatc    960
tggcgcacct tccagaagga tgagctgctg aagcgcatcc tggatatgag caacgagtac   1020
agcctgttca tcaccagcga tcatctgcgc cagatgctgt acaacacctt ctacagcaag   1080
gagaagcacc tgaacaacat cttccaccac ctgatctacg tgctgcagat gaagttcaac   1140
gacgtgccca tcaagatgga gtacttccag acctataaga gaacaagcc cctgacccag   1200

<210> SEQ ID NO 4
<211> LENGTH: 1200
<212> TYPE: DNA
```

<213> ORGANISM: Plasmodium falciparum

<400> SEQUENCE: 4

| | |
|---|---|
| gacgtgaaga acaacgagga ctacaagaac gtggactata agaatgtgaa cttcctgcag | 60 |
| taccacttca aggagctgag caactacaat atcgccaaca gcatcgacat tctgcaggag | 120 |
| aaggagggcc acctggattt cgtgatcatc ccccactaca cctttctgga ctactacaag | 180 |
| cacctgagct acaactccat ctaccacaag agcagcacct acggcaagtg cattgccgtg | 240 |
| gatgccttca tcaagaagat caacgagacc tacgacaaag tgaagtccaa gtgcaacgac | 300 |
| atcaagaacg acctgatcgc cacgatcaag aagctggagc accctacga tatcaacaac | 360 |
| aagaacgatg acagctaccg ctacgacatc agcgaggaga tcgacgataa gtccgaggag | 420 |
| acggacgacg agaccgagga ggtggaggat agcatccagg ataccgatag caaccacacc | 480 |
| cccagcaaca agaagaagaa tgatctgatg aaccgcacct ttaagaagat gatggacgag | 540 |
| tacaatacga aaagaagaa gctgatcaag tgcatcaaga atcacgagaa cgacttcaac | 600 |
| aagatctgca tggacatgaa gaactacggc accaacctgt tcgagcagct gtcctgctac | 660 |
| aacaacaact tctgcaacac caacggcatc cgctaccact acgatgagta catccacaag | 720 |
| ctgatcctga gcgtgaagtc gaagaacctg aacaaggatc tgagcgacat gaccaacatc | 780 |
| ctgcagcaga gcgagctgct gctgaccaat ctgaacaaga agatgggcag ctacatctac | 840 |
| atcgacacca tcaagttcat tcacaaggag atgaagcaca tcttcaaccg catcgagtac | 900 |
| cacaccaaga tcatcaacga caagacgaag atcattcagg acaagatcaa gctgaacatc | 960 |
| tggcgcaccc tccagaagga tgagctgctg aagcgcatcc tggatatgag caacgagtac | 1020 |
| agcctgttca tcaccagcga tcatctgcgc cagatgctgt acaacaccctt ctacagcaag | 1080 |
| gagaagcacc tgaacaacat cttccaccac ctgatctacg tgctgcagat gaagttcaac | 1140 |
| gacgtgccca tcaagatgga gtacttccag acctataaga gaacaagcc cctgacccag | 1200 |

<210> SEQ ID NO 5
<211> LENGTH: 1620
<212> TYPE: DNA
<213> ORGANISM: Plasmodium falciparum

<400> SEQUENCE: 5

| | |
|---|---|
| caggaggccg tgccagagga gagcaccgag attgcccacc gcaccgagac ccgcaccgat | 60 |
| gagcgcaaga tcaggagcc cgccaacaag gatctgaaga accccagca gagcgtgggc | 120 |
| gagaacggca cgaaggatct gctgcaggag gatctgggag cagccgcag cgaggatgaa | 180 |
| gtgacccagg agttcggcgt gaaccacggc atccccaagg gcgaggatca gaccctggga | 240 |
| aagtccgatg ccatccccaa catcggcgag cccgagaccg gaatcagtac caccgaggag | 300 |
| tcccgccacg aggagggcca taacaagcag gccctgagca cctccgtgga tgagcccgag | 360 |
| ctgagcgata ccctgcagct gcacgaggat accaaggaga cgataagct gcccctggag | 420 |
| agcagcacca tcaccagccc aaccgagagc ggcagcagcg ataccgagga cccccatcc | 480 |
| attagcgagg gcccgaaggg caacgagcag aagaagcgcg acgacgatag cctgagcaag | 540 |
| atcagcgtgt cccccgagaa cagccgccca gagaccgatg ccaaggatac cagcaacctg | 600 |
| ctgaagctga agggcgacgt ggacatcagc atgcccaagg ccgtgatcgg cagctccccc | 660 |
| aacgataaca tcaacgtgac cgagcagggc gacaacatct cgggcgtgaa cagcaagccc | 720 |
| ctgtccgatg atgtgcgccc cgataagaac catgaggaag tgaaggagca caccagcaac | 780 |
| agcgataacg tgcagcagtc cggcggcatc gtgaacatga acgtggagaa ggagctgaag | 840 |

```
gacaccctgg agaaccccag ctccagcctg gatgagggaa aggcccatga ggagctgtcc    900
gagcccaacc tgtccagcga tcaggatatg agcaacaccc caggccccct ggataacacc    960
tcggaggaga cgaccgagcg catcagcaac aacgagtaca agtgaacga gcgcgagggc   1020
gagcgcaccc tgaccaagga gtatgaggat atcgtgctga agtccacat gaaccgcgag   1080
agcgacgatg gcgagctgta cgatgagaac agcgatctga gcaccgtgaa cgatgagtcc   1140
gaggatgccg aggccaagat gaagggcaat gataccagcg agatgagcca acagcagc   1200
cagcacatcg agagcgatca gcagaagaac gatatgaaga ccgtgggcga cctgggcacc   1260
acccacgtgc agaatgagat ctccgtgccc gtgaccggcg agatcgatga agctgcgc   1320
gagagcaagg agtccaagat ccacaaggcc gaggaggagc gcctgagcca caccgatatc   1380
cacaagatca accccgagga tcgcaactcc aacaccctgc acctgaagga tatccgcaac   1440
gaggagaatg agcgccacct gacgaaccag aacatcaaca tcagccagga gcgcgacctg   1500
cagaagcacg gcttccacac catgaacaac ctgcacggcg acggcgtgtc cgagcgcagc   1560
cagatcaatc actcgcacca cggcaaccgc caggatcgcg aggaaatag tggaagcgcc   1620
```

<210> SEQ ID NO 6
<211> LENGTH: 1067
<212> TYPE: PRT
<213> ORGANISM: Plasmodium falciparum

<400> SEQUENCE: 6

```
Ile Asp Leu Ile Glu Gly Ile Phe Tyr Glu Lys Asn Glu Ile Asp Lys
1               5                   10                  15

Leu Thr Phe Ser Leu Asp His Arg Val Arg Asp Asn Leu Lys Thr Asp
            20                  25                  30

Leu Ile Leu Asn Asn Asn Gly Glu Asn Asp Tyr Ala Tyr Leu Asn Lys
        35                  40                  45

Tyr Val Tyr Thr Ile Leu Asn Arg Asp Ser Thr Glu Lys Ile Lys Thr
    50                  55                  60

Phe Phe Ser His Asn Lys Asp Met Lys Ser Cys Asp Tyr Phe Ile Ser
65                  70                  75                  80

Lys Glu Tyr Asn Ser Ser Asp Lys Thr Asn Gln Ile Cys Tyr Lys Lys
                85                  90                  95

Thr Phe Cys Gly Val Val Ile Pro Asn Ser Glu Glu Ile Lys Thr Asn
            100                 105                 110

Lys Ile Thr Asn Asp Lys Leu Tyr Cys Ala His Phe Asn Ser Thr His
        115                 120                 125

Ile Ile Ile Tyr Tyr Ile Ser Gln Pro Leu Leu Leu Glu Pro His Val
    130                 135                 140

Val Tyr Glu Glu Thr Phe Phe Glu Lys Gly Lys Asn Asp Gln Ile Asn
145                 150                 155                 160

Cys Gln Gly Met Tyr Ile Ser Leu Arg Ser Val His Val His Thr His
                165                 170                 175

Asn Ala Ile Leu Gln Gln Glu Thr Leu Thr Tyr Ile Lys Asn Leu Cys
            180                 185                 190

Asp Gly Lys Asn Asn Cys Lys Phe Asp Phe Asp Ser Ile Lys Tyr Glu
        195                 200                 205

Asn Lys Ser Leu Thr His Tyr Leu Phe Phe Ile Asn Ile Gln Tyr Gln
    210                 215                 220

Cys Ile Ser Pro Leu Asn Leu Gln Glu Asn Glu Met Cys Asp Val Tyr
225                 230                 235                 240
```

Asn Asp Asp Thr His Lys Ala Thr Cys Lys Tyr Gly Phe Asn Lys Ile
            245                 250                 255

Glu Leu Leu Lys Asn Val Cys Glu Glu Asn Tyr Arg Cys Thr Gln Asp
            260                 265                 270

Ile Cys Ser Val Asn Gln Phe Cys Asp Gly Glu Asn Glu Thr Cys Thr
            275                 280                 285

Cys Lys Thr Ser Leu Leu Pro Ser Ala Lys Asn Asn Cys Glu Tyr Asn
        290                 295                 300

Asp Leu Cys Thr Val Leu Asn Cys Pro Glu Asn Ser Thr Cys Glu Gln
305                 310                 315                 320

Ile Gly Asn Gly Lys Lys Ala Glu Cys Lys Cys Glu Asn Gly Lys Tyr
                325                 330                 335

Tyr His Asn Asn Lys Cys Tyr Thr Lys Asn Asp Leu Glu Leu Ala Ile
                340                 345                 350

Lys Ile Glu Pro His Lys Lys Glu Lys Phe Tyr Lys Asn Asn Leu Tyr
            355                 360                 365

Gln Gly Lys Ala Leu Lys Pro Glu Tyr Ile Phe Met Gln Cys Glu Asn
        370                 375                 380

Gly Phe Ser Ile Glu Val Ile Asn Ala Tyr Val Ser Cys Tyr Arg Val
385                 390                 395                 400

Ser Phe Asn Leu Asn Lys Leu Lys Tyr Val Thr Glu Ser Leu Lys Lys
                405                 410                 415

Met Cys Asp Gly Lys Thr Lys Cys Ala Tyr Gly Asn Thr Ile Asp Pro
            420                 425                 430

Ile Asp Asp Leu Asn His His Asn Ile Cys Asn Asn Phe Asn Thr Ile
            435                 440                 445

Phe Lys Tyr Asp Tyr Leu Cys Val Phe Asn Asn Gln Asn Ile Thr Ser
        450                 455                 460

Asp Lys Asn Ser His Leu His Ser Asn Ile Pro Ser Leu Tyr Asn Ser
465                 470                 475                 480

Ser Ile Leu Pro Asp Ile Asn Lys Ser Lys Phe His Leu Ile Ser Arg
                485                 490                 495

Asn Ser Arg Thr Asn Gln Tyr Pro His Asn Asn Ile Ser Met Leu Glu
            500                 505                 510

Ile Gln Asn Glu Ile Ser Ser His Asn Ser Gln Phe Ser Thr Asp
        515                 520                 525

Pro His Thr Asn Ser Asn Asn Ile Asn Asn Met Asn Ile Lys Lys Val
    530                 535                 540

Glu Ile Phe Arg Ser Arg Phe Ser Ser Lys Leu Gln Cys Gln Gly Gly
545                 550                 555                 560

Lys Ile Asn Ile Asp Lys Ala Ile Leu Lys Gly Gly Glu Gly Cys Asn
                565                 570                 575

Asp Leu Leu Thr Asn Ser Leu Lys Ser Tyr Cys Asn Asp Leu Ser
            580                 585                 590

Glu Cys Asp Ile Gly Leu Ile Tyr His Phe Asp Thr Tyr Cys Ile Asn
        595                 600                 605

Asp Gln Tyr Leu Phe Val Ser Tyr Ser Cys Ser Asn Leu Cys Asn Lys
        610                 615                 620

Cys His Asn Asn Ser Thr Cys Tyr Gly Asn Arg Phe Asn Tyr Asp Cys
625                 630                 635                 640

Phe Cys Asp Asn Pro Tyr Ile Ser Lys Tyr Gly Asn Lys Leu Cys Glu
            645                 650                 655

-continued

Arg Pro Asn Asp Cys Glu Ser Val Leu Cys Ser Gln Asn Gln Val Cys
            660                 665                 670

Gln Ile Leu Pro Asn Asp Lys Leu Ile Cys Gln Cys Glu Glu Gly Tyr
        675                 680                 685

Lys Asn Val Lys Gly Lys Cys Val Pro Asp Asn Lys Cys Asp Leu Ser
        690                 695                 700

Cys Pro Ser Asn Lys Val Cys Val Ile Glu Asn Gly Lys Gln Thr Cys
705                 710                 715                 720

Lys Cys Ser Glu Arg Phe Val Leu Glu Asn Gly Val Cys Ile Cys Ala
                725                 730                 735

Asn Asp Tyr Lys Met Glu Asp Gly Ile Asn Cys Ile Ala Lys Asn Lys
            740                 745                 750

Cys Lys Arg Lys Glu Tyr Glu Asn Ile Cys Thr Asn Pro Asn Glu Met
        755                 760                 765

Cys Ala Tyr Asn Glu Glu Thr Asp Ile Val Lys Cys Glu Cys Lys Glu
        770                 775                 780

His Tyr Tyr Arg Ser Ser Arg Gly Glu Cys Ile Leu Asn Asp Tyr Cys
785                 790                 795                 800

Lys Asp Ile Asn Cys Lys Glu Asn Glu Glu Cys Ser Ile Val Asn Phe
                805                 810                 815

Lys Pro Glu Cys Val Cys Lys Glu Asn Leu Lys Lys Asn Asn Lys Gly
            820                 825                 830

Glu Cys Ile Tyr Glu Asn Ser Cys Leu Ile Asn Glu Gly Asn Cys Pro
        835                 840                 845

Lys Asp Ser Lys Cys Ile Tyr Arg Glu Tyr Lys Pro His Glu Cys Val
850                 855                 860

Cys Asn Lys Gln Gly His Val Ala Val Asn Gly Lys Cys Val Leu Glu
865                 870                 875                 880

Asp Lys Cys Val His Asn Lys Lys Cys Ser Glu Asn Ser Ile Cys Val
                885                 890                 895

Asn Val Met Asn Lys Glu Pro Ile Cys Val Cys Thr Tyr Asn Tyr Tyr
            900                 905                 910

Lys Lys Asp Gly Val Cys Leu Ile Gln Asn Pro Cys Leu Lys Asp Asn
        915                 920                 925

Gly Gly Cys Ser Arg Asn Ser Glu Cys Thr Phe Lys Tyr Ser Lys Ile
    930                 935                 940

Asn Cys Thr Cys Lys Glu Asn Tyr Lys Asn Lys Asp Asp Ser Cys Val
945                 950                 955                 960

Pro Asn Thr Asn Glu Tyr Asp Glu Ser Phe Thr Phe Gln Tyr Asn Asp
                965                 970                 975

Asp Ala Ser Ile Ile Leu Gly Ala Cys Gly Met Ile Glu Phe Ser Tyr
            980                 985                 990

Ile Tyr Asn Gln Ile Ile Trp Lys Ile Asn Asn Ser Lys Glu Ser Tyr
        995                 1000                1005

Val Phe Tyr Tyr Asp Tyr Pro Thr Ala Gly Asn Ile Glu Val Gln
        1010                1015                1020

Ile Lys Asn Glu Ile Phe His Thr Ile Ile Tyr Leu Lys Lys Lys
        1025                1030                1035

Ile Gly Asn Ser Val Ile Tyr Asp Asp Phe Gln Val Asp His Gln
        1040                1045                1050

Thr Cys Ile Tyr Glu Asn Val Phe Tyr Tyr Ser Asn Gln Asn
        1055                1060                1065

<210> SEQ ID NO 7
<211> LENGTH: 333
<212> TYPE: PRT
<213> ORGANISM: Plasmodium falciparum

<400> SEQUENCE: 7

Ser Arg His Val Phe Ile Arg Thr Glu Leu Ser Phe Ile Lys Asn Asn
1               5                   10                  15

Val Pro Cys Ile Arg Asp Met Phe Phe Ile Tyr Lys Arg Glu Leu Tyr
                20                  25                  30

Asn Ile Cys Leu Asp Asp Leu Lys Gly Glu Glu Asp Glu Thr His Ile
            35                  40                  45

Tyr Val Gln Lys Lys Val Lys Asp Ser Trp Ile Thr Leu Asn Asp Leu
50                  55                  60

Phe Lys Glu Thr Asp Leu Thr Gly Arg Pro His Ile Phe Ala Tyr Val
65                  70                  75                  80

Asp Val Glu Glu Ile Ile Ile Leu Leu Cys Glu Asp Glu Glu Phe Ser
                85                  90                  95

Asn Arg Lys Lys Asp Met Thr Cys His Arg Phe Tyr Ser Asn Asp Gly
            100                 105                 110

Lys Glu Tyr Asn Asn Ser Glu Ile Thr Ile Ser Asp Tyr Ile Leu Lys
        115                 120                 125

Asp Lys Leu Leu Ser Ser Tyr Val Ser Leu Pro Leu Lys Ile Glu Asn
130                 135                 140

Arg Glu Tyr Phe Leu Ile Cys Gly Val Ser Pro Tyr Lys Phe Lys Asp
145                 150                 155                 160

Asp Asn Lys Lys Asp Asp Ile Leu Cys Met Ala Ser His Asp Lys Gly
                165                 170                 175

Glu Thr Trp Gly Thr Lys Ile Val Ile Lys Tyr Asp Asn Tyr Lys Leu
            180                 185                 190

Gly Val Gln Tyr Phe Phe Leu Arg Pro Tyr Ile Ser Lys Asn Asp Leu
        195                 200                 205

Ser Phe His Phe Tyr Val Gly Asp Asn Ile Asn Asn Val Lys Asn Val
210                 215                 220

Asn Phe Ile Glu Cys Thr His Glu Lys Asp Leu Glu Phe Val Cys Ser
225                 230                 235                 240

Asn Arg Asp Phe Leu Lys Asp Asn Lys Val Leu Gln Asp Val Ser Thr
                245                 250                 255

Leu Asn Asp Glu Tyr Ile Val Ser Tyr Gly Asn Asp Asn Asn Phe Ala
            260                 265                 270

Glu Cys Tyr Ile Phe Phe Asn Asn Glu Asn Ser Ile Leu Ile Lys Pro
        275                 280                 285

Glu Lys Tyr Gly Asn Thr Thr Ala Gly Cys Tyr Gly Gly Thr Phe Val
290                 295                 300

Lys Ile Asp Glu Asn Arg Thr Leu Phe Ile Tyr Ser Ser Ser Gln Gly
305                 310                 315                 320

Ile Tyr Asn Ile His Thr Ile Tyr Tyr Ala Asn Tyr Glu
                325                 330

<210> SEQ ID NO 8
<211> LENGTH: 526
<212> TYPE: PRT
<213> ORGANISM: Plasmodium falciparum

<400> SEQUENCE: 8

Met Ile Arg Ile Lys Lys Lys Leu Ile Leu Thr Ile Ile Tyr Ile His

-continued

```
 1               5                  10                 15
Leu Phe Ile Leu Asn Arg Leu Ser Phe Glu Asn Ala Ile Lys Lys Thr
             20                 25                 30
Lys Asn Gln Glu Asn Asn Leu Thr Leu Leu Pro Ile Lys Ser Thr Glu
             35                 40                 45
Glu Glu Lys Asp Asp Ile Lys Asn Gly Lys Asp Ile Lys Lys Glu Ile
             50                 55                 60
Asp Asn Asp Lys Glu Asn Ile Lys Thr Asn Asn Ala Lys Asp His Ser
 65                 70                 75                 80
Thr Tyr Ile Lys Ser Tyr Leu Asn Thr Asn Val Asn Asp Gly Leu Lys
             85                 90                 95
Tyr Leu Phe Ile Pro Ser His Asn Ser Phe Ile Lys Lys Tyr Ser Val
             100                105                110
Phe Asn Gln Ile Asn Asp Gly Met Leu Leu Asn Glu Lys Asn Asp Val
             115                120                125
Lys Asn Asn Glu Asp Tyr Lys Asn Val Asp Tyr Lys Asn Val Asn Phe
             130                135                140
Leu Gln Tyr His Phe Lys Glu Leu Ser Asn Tyr Asn Ile Ala Asn Ser
145                150                155                160
Ile Asp Ile Leu Gln Glu Lys Glu Gly His Leu Asp Phe Val Ile Ile
             165                170                175
Pro His Tyr Thr Phe Leu Asp Tyr Tyr Lys His Leu Ser Tyr Asn Ser
             180                185                190
Ile Tyr His Lys Ser Ser Thr Tyr Gly Lys Cys Ile Ala Val Asp Ala
             195                200                205
Phe Ile Lys Lys Ile Asn Glu Thr Tyr Asp Lys Val Lys Ser Lys Cys
             210                215                220
Asn Asp Ile Lys Asn Asp Leu Ile Ala Thr Ile Lys Lys Leu Glu His
225                230                235                240
Pro Tyr Asp Ile Asn Asn Lys Asn Asp Ser Tyr Arg Tyr Asp Ile
             245                250                255
Ser Glu Glu Ile Asp Asp Lys Ser Glu Glu Thr Asp Asp Glu Thr Glu
             260                265                270
Glu Val Glu Asp Ser Ile Gln Asp Thr Asp Ser Asn His Thr Pro Ser
             275                280                285
Asn Lys Lys Lys Asn Asp Leu Met Asn Arg Thr Phe Lys Lys Met Met
             290                295                300
Asp Glu Tyr Asn Thr Lys Lys Lys Leu Ile Lys Cys Ile Lys Asn
305                310                315                320
His Glu Asn Asp Phe Asn Lys Ile Cys Met Asp Met Lys Asn Tyr Gly
             325                330                335
Thr Asn Leu Phe Glu Gln Leu Ser Cys Tyr Asn Asn Phe Cys Asn
             340                345                350
Thr Asn Gly Ile Arg Tyr His Tyr Asp Glu Tyr Ile His Lys Leu Ile
             355                360                365
Leu Ser Val Lys Ser Lys Asn Leu Asn Lys Asp Leu Ser Asp Met Thr
             370                375                380
Asn Ile Leu Gln Gln Ser Glu Leu Leu Leu Thr Asn Leu Asn Lys Lys
385                390                395                400
Met Gly Ser Tyr Ile Tyr Ile Asp Thr Ile Lys Phe Ile His Lys Glu
             405                410                415
Met Lys His Ile Phe Asn Arg Ile Glu Tyr His Thr Lys Ile Ile Asn
             420                425                430
```

```
Asp Lys Thr Lys Ile Ile Gln Asp Lys Ile Lys Leu Asn Ile Trp Arg
            435                 440                 445

Thr Phe Gln Lys Asp Glu Leu Leu Lys Arg Ile Leu Asp Met Ser Asn
450                 455                 460

Glu Tyr Ser Leu Phe Ile Thr Ser Asp His Leu Arg Gln Met Leu Tyr
465                 470                 475                 480

Asn Thr Phe Tyr Ser Lys Glu Lys His Leu Asn Asn Ile Phe His His
                485                 490                 495

Leu Ile Tyr Val Leu Gln Met Lys Phe Asn Asp Val Pro Ile Lys Met
                500                 505                 510

Glu Tyr Phe Gln Thr Tyr Lys Lys Asn Lys Pro Leu Thr Gln
                515                 520                 525

<210> SEQ ID NO 9
<211> LENGTH: 400
<212> TYPE: PRT
<213> ORGANISM: Plasmodium falciparum

<400> SEQUENCE: 9

Asp Val Lys Asn Asn Glu Asp Tyr Lys Asn Val Asp Tyr Lys Asn Val
1               5                   10                  15

Asn Phe Leu Gln Tyr His Phe Lys Glu Leu Ser Asn Tyr Asn Ile Ala
                20                  25                  30

Asn Ser Ile Asp Ile Leu Gln Lys Glu Gly His Leu Asp Phe Val
            35                  40                  45

Ile Ile Pro His Tyr Thr Phe Leu Asp Tyr Tyr Lys His Leu Ser Tyr
50                  55                  60

Asn Ser Ile Tyr His Lys Ser Ser Thr Tyr Gly Lys Cys Ile Ala Val
65                  70                  75                  80

Asp Ala Phe Ile Lys Lys Ile Asn Glu Thr Tyr Asp Lys Val Lys Ser
                85                  90                  95

Lys Cys Asn Asp Ile Lys Asn Asp Leu Ile Ala Thr Ile Lys Lys Leu
            100                 105                 110

Glu His Pro Tyr Asp Ile Asn Asn Lys Asn Asp Asp Ser Tyr Arg Tyr
        115                 120                 125

Asp Ile Ser Glu Glu Ile Asp Asp Lys Ser Glu Glu Thr Asp Asp Glu
    130                 135                 140

Thr Glu Glu Val Glu Asp Ser Ile Gln Asp Thr Asp Ser Asn His Thr
145                 150                 155                 160

Pro Ser Asn Lys Lys Asn Asp Leu Met Asn Arg Thr Phe Lys Lys
                165                 170                 175

Met Met Asp Glu Tyr Asn Thr Lys Lys Lys Leu Ile Lys Cys Ile
            180                 185                 190

Lys Asn His Glu Asn Asp Phe Asn Lys Ile Cys Met Asp Met Lys Asn
        195                 200                 205

Tyr Gly Thr Asn Leu Phe Glu Gln Leu Ser Cys Tyr Asn Asn Asn Phe
    210                 215                 220

Cys Asn Thr Asn Gly Ile Arg Tyr His Tyr Asp Glu Tyr Ile His Lys
225                 230                 235                 240

Leu Ile Leu Ser Val Lys Ser Lys Asn Leu Asn Lys Asp Leu Ser Asp
                245                 250                 255

Met Thr Asn Ile Leu Gln Gln Ser Glu Leu Leu Leu Thr Asn Leu Asn
            260                 265                 270

Lys Lys Met Gly Ser Tyr Ile Tyr Ile Asp Thr Ile Lys Phe Ile His
```

```
            275                 280                 285
Lys Glu Met Lys His Ile Phe Asn Arg Ile Glu Tyr His Thr Lys Ile
            290                 295                 300

Ile Asn Asp Lys Thr Lys Ile Ile Gln Asp Lys Ile Lys Leu Asn Ile
305                 310                 315                 320

Trp Arg Thr Phe Gln Lys Asp Glu Leu Leu Lys Arg Ile Leu Asp Met
            325                 330                 335

Ser Asn Glu Tyr Ser Leu Phe Ile Thr Ser Asp His Leu Arg Gln Met
            340                 345                 350

Leu Tyr Asn Thr Phe Tyr Ser Lys Glu Lys His Leu Asn Asn Ile Phe
            355                 360                 365

His His Leu Ile Tyr Val Leu Gln Met Lys Phe Asn Asp Val Pro Ile
            370                 375                 380

Lys Met Glu Tyr Phe Gln Thr Tyr Lys Lys Asn Lys Pro Leu Thr Gln
385                 390                 395                 400

<210> SEQ ID NO 10
<211> LENGTH: 538
<212> TYPE: PRT
<213> ORGANISM: Plasmodium falciparum

<400> SEQUENCE: 10

Gln Glu Ala Val Pro Glu Ser Thr Glu Ile Ala His Arg Thr Glu
1               5                   10                  15

Thr Arg Thr Asp Glu Arg Lys Asn Gln Glu Pro Ala Asn Lys Asp Leu
                20                  25                  30

Lys Asn Pro Gln Gln Ser Val Gly Glu Asn Gly Thr Lys Asp Leu Leu
            35                  40                  45

Gln Glu Asp Leu Gly Gly Ser Arg Ser Glu Asp Glu Val Thr Gln Glu
        50                  55                  60

Phe Gly Val Asn His Gly Ile Pro Lys Gly Glu Asp Gln Thr Leu Gly
65                  70                  75                  80

Lys Ser Asp Ala Ile Pro Asn Ile Gly Glu Pro Thr Gly Ile Ser
                85                  90                  95

Thr Thr Glu Glu Ser Arg His Glu Glu Gly His Asn Lys Gln Ala Leu
                100                 105                 110

Ser Thr Ser Val Asp Glu Pro Glu Leu Ser Asp Thr Leu Gln Leu His
            115                 120                 125

Glu Asp Thr Lys Glu Asn Asp Lys Leu Pro Leu Glu Ser Ser Thr Ile
        130                 135                 140

Thr Ser Pro Thr Glu Ser Gly Ser Ser Asp Thr Glu Glu Thr Pro Ser
145                 150                 155                 160

Ile Ser Glu Gly Pro Lys Gly Asn Glu Gln Lys Lys Arg Asp Asp
                165                 170                 175

Ser Leu Ser Lys Ile Ser Val Ser Pro Glu Asn Ser Arg Pro Glu Thr
            180                 185                 190

Asp Ala Lys Asp Thr Ser Asn Leu Lys Leu Lys Gly Asp Val Asp
        195                 200                 205

Ile Ser Met Pro Lys Ala Val Ile Gly Ser Pro Asn Asp Asn Ile
210                 215                 220

Asn Val Thr Glu Gln Gly Asp Asn Ile Ser Gly Val Asn Ser Lys Pro
225                 230                 235                 240

Leu Ser Asp Asp Val Arg Pro Asp Lys Asn His Glu Glu Val Lys Glu
                245                 250                 255
```

```
His Thr Ser Asn Ser Asp Asn Val Gln Ser Gly Gly Ile Val Asn
            260                 265                 270

Met Asn Val Glu Lys Glu Leu Lys Asp Thr Leu Glu Asn Pro Ser Ser
        275                 280                 285

Ser Leu Asp Glu Gly Lys Ala His Glu Glu Leu Ser Glu Pro Asn Leu
    290                 295                 300

Ser Ser Asp Gln Asp Met Ser Asn Thr Pro Gly Pro Leu Asp Asn Thr
305                 310                 315                 320

Ser Glu Glu Thr Thr Glu Arg Ile Ser Asn Asn Glu Tyr Lys Val Asn
                325                 330                 335

Glu Arg Glu Gly Glu Arg Thr Leu Thr Lys Glu Tyr Glu Asp Ile Val
            340                 345                 350

Leu Lys Ser His Met Asn Arg Glu Ser Asp Asp Gly Glu Leu Tyr Asp
        355                 360                 365

Glu Asn Ser Asp Leu Ser Thr Val Asn Asp Glu Ser Glu Asp Ala Glu
    370                 375                 380

Ala Lys Met Lys Gly Asn Asp Thr Ser Glu Met Ser His Asn Ser Ser
385                 390                 395                 400

Gln His Ile Glu Ser Asp Gln Gln Lys Asn Asp Met Lys Thr Val Gly
                405                 410                 415

Asp Leu Gly Thr Thr His Val Gln Asn Glu Ile Ser Val Pro Val Thr
            420                 425                 430

Gly Glu Ile Asp Glu Lys Leu Arg Glu Ser Lys Glu Ser Lys Ile His
        435                 440                 445

Lys Ala Glu Glu Arg Leu Ser His Thr Asp Ile His Lys Ile Asn
    450                 455                 460

Pro Glu Asp Arg Asn Ser Asn Thr Leu His Leu Lys Asp Ile Arg Asn
465                 470                 475                 480

Glu Glu Asn Glu Arg His Leu Thr Asn Gln Asn Ile Asn Ile Ser Gln
                485                 490                 495

Glu Arg Asp Leu Gln Lys His Gly Phe His Thr Met Asn Asn Leu His
            500                 505                 510

Gly Asp Gly Val Ser Glu Arg Ser Gln Ile Asn His Ser His His Gly
        515                 520                 525

Asn Arg Gln Asp Arg Gly Gly Asn Ser Gly
    530                 535

<210> SEQ ID NO 11
<211> LENGTH: 2531
<212> TYPE: DNA
<213> ORGANISM: Artificial Sequence
<220> FEATURE:
<223> OTHER INFORMATION: Vector

<400> SEQUENCE: 11
cgtaagtatc aaggttacaa gacaggttta aggagaccaa tagaaactgg gcttgtcgag    60
acagagaaga ctcttgcgtt tctgataggc acctattggt cttactgaca tccactttgc   120
ctttctctcc acaggaattc tggatcctct agaccggtca tatgcggccg cggatcgatc   180
gatatctgac taaatcttag tttgtattgt catgttttaa tacaatatgt tatgtttaaa   240
tatgttttta ataaatttta taaaataatt tcaacttttta ttgtaacaac attgtccatt   300
tacacactcc tttcaagcgc gtgggactcg atgctcggcg ccactcaaag gcggtaatac   360
ggttatccac agaatcaggg gataacgcag gaaagaacat gtgagcaaaa ggccagcaaa   420
aggccaggaa ccgtaaaaag gccgcgttgc tggcgttttt ccataggctc cgcccccctg   480
```

```
acgagcatca caaaaatcga cgctcaagtc agaggtggcg aaacccgaca ggactataaa    540
gataccaggc gtttccccct ggaagctccc tcgtgcgctc tcctgttccg accctgccgc    600
ttaccggata cctgtccgcc tttctcccct cgggaagcgt ggcgctttct caatgctcac    660
gctgtaggta tctcagttcg gtgtaggtcg ttcgctccaa gctgggctgt gtgcacgaac    720
cccccgttca gcccgaccgc tgcgccttat ccggtaacta tcgtcttgag tccaacccgg    780
taagacacga cttatcgcca ctggcagcag ccactggtaa caggattagc agagcgaggt    840
atgtaggcgg tgctacagag ttcttgaagt ggtggcctaa ctacggctac actagaagga    900
cagtatttgg tatctgcgct ctgctgaagc cagttacctt cggaaaaaga gttggtagct    960
cttgatccgg caaacaaacc accgctggta gcggtggttt ttttgtttgc aagcagcaga    1020
ttacgcgcag aaaaaaagga tctcaagaag atcctttgat cttttctacg ggtctgacg    1080
ctcagtggaa cgaaaactca cgttaaggga ttttgcatgc gctaagcggg ctttataaaa    1140
cgggctgcgg gaccagtttt catatcacta ccgtttgagt tcttgtgctg tgtggatact    1200
cctcccgaca ccgaattaat tcggatctct gcaagggatt ttggtcatga acaataaaac    1260
tgtctgctta cataaacagt aatacaaggg gtgttcatag tataatacga ctcactatag    1320
gagggccacc atggccaagt tgaccagtgc cgttccggtg ctcaccgcgc gcgacgtcgc    1380
cggagcggtc gagttctgga ccgaccggct cgggttcagc cgggacttcg tggaggacga    1440
cttcgccggt gtggtccggg acgacgtgac cctgttcatc agcgcggtcc aggaccaggt    1500
ggtgccggac aacaccctgg cctgggtgtg gtgcgcggc ctggacgagc tgtacgccga    1560
gtggtcggag gtcgtgtcca cgaacttccg ggacgcctcc gggccggcca tgaccgagat    1620
cggcgagcag ccgtggggc gggagttcgc cctgcgcgac ccggccggca actgcgtgca    1680
cttcgtggcc gaggagcagg actgaccgac gccgaccaac accgccggtc cgacggcggc    1740
ccacgggtcc caggggggtc gacctcgaaa cttgtttatt gcagcttata atggttacaa    1800
ataaagcaat agcatcacaa atttcacaaa taaagcattt ttttcactgc attctagttg    1860
tggtttgtcc aaactcatca atgtatctta tcatgtcttc acgtaataag tgtgcggcta    1920
gcagtcaact actagtgaat gccctactag aagatgtgtg ttgcacaaaa tgtccctgga    1980
ataaccaatt tgaagtgcag atagcagtaa acgtaagcta atatgaatat tatttaactg    2040
taatgtttta atatcgctgg acattactaa taaacccact ataaacacat gtacatatgt    2100
atgttttggc atacaatgag tagttgggga aaaatgtgt aaaagcaccg tgaccatcac    2160
agcataaaga taaccagctg aagtatcgaa tatgagtaac ccccaaattg aatcacatgc    2220
cgcaactgat aggacccatg gaagtacact cttcatggcg atatacaaga cacacacaag    2280
cacgaacacc cagttgcgga ggaaattctc cgtaaatgaa acccaatcg gcgaacaatt    2340
catacccata tatggtaaaa gttttgaacg cgacttaaga gcgccggagt ataaatagag    2400
gcgcttcgtc tacggagcga caattcaatt caaacaagca aagtgaacac gtcgctaagc    2460
gaaagctaag caaataaaca agcgcagctg aacaagctaa acaatctgca gaagcttggt    2520
accctcgagc t                                                         2531
```

<210> SEQ ID NO 12
<211> LENGTH: 2799
<212> TYPE: DNA
<213> ORGANISM: Artificial Sequence
<220> FEATURE:
<223> OTHER INFORMATION: Vector

```
<400> SEQUENCE: 12
aattcggatc tctgcaaggg attttggtca tgaacaataa aactgtctgc ttacataaac      60
agtaatacaa ggggtgttca tagtataata cgactcacta taggagggcc accatgagcc     120
acatccagcg cgaaaccagc tgcagccgtc cgcgcctgaa cagcaacatg gatgccgatc     180
tgtacggcta caaatgggcc cgcgataacg tgggccagag cggcgctacc atctaccgcc     240
tgtacggcaa accggatgcc ccggaactgt tcctgaaaca cggcaaaggc agcgtggcca     300
acgatgtgac cgatgaaatg gtgcgcctga actggctgac cgagttcatg ccgctgccga     360
ccatcaaaca cttcatccgc accccggatg atgcctggct gctgaccacc gccattccgg     420
gcaaaaccgc cttccaggtg ctggaagaat acccggatag cggcgaaaac atcgtggatg     480
ccctggccgt gttcctgcgc cgcctgcaca gcatcccggt gtgcaactgc ccgttcaaca     540
gcgatcgcgt gttccgcctg gctcaggccc agagccgcat gaacaacggc ctggtggatg     600
ccagcgattt cgatgatgaa cgcaacggct ggccggtgga acaggtgtgg aaagagatgc     660
acaaactgct gccgttcagc ccggattccg tggtgaccca cggcgatttc agcctggata     720
acctgatctt cgatgagggc aaactgatcg gctgcatcga tgtgggccgc gtgggcattg     780
ccgatcgcta ccaggatctg gccatcctgt ggaactgcct gggcgagttc agcccgagcc     840
tgcagaaacg cctgttccag aagtacggca tcgataaccc ggatatgaac aaactgcagt     900
tccacctgat gctggatgag ttcttctaat aagtcgacct cgaaacttgt ttattgcagc     960
ttataatggt tacaaataaa gcaatagcat cacaaatttc acaaataaag cattttttc     1020 actgcattct agttgtggtt tgtccaaact catcaatgta tcttatcatg tcttcacgta     1080
ataagtgtgc ggctagcagt caactactag tgaatgccct actagaagat gtgtgttgca     1140
caaaatgtcc ctggaataac caatttgaag tgcagatagc agtaaacgta agctaatatg     1200
aatattattt aactgtaatg ttttaatatc gctggacatt actaataaac ccactataaa     1260
cacatgtaca tatgtatgtt ttggcataca atgagtagtg ggggaaaaaa tgtgtaaaag     1320
caccgtgacc atcacagcat aaagataacc agctgaagta tcgaatatga gtaaccccca     1380
aattgaatca catgccgcaa ctgataggac ccatggaagt acactcttca tggcgatata     1440
caagacacac acaagcacga acacccagtt gcggaggaaa ttctccgtaa atgaaaaccc     1500
aatcggcgaa caattcatac ccatatatgg taaaagtttt gaacgcgagc gaacttaaga     1560
gcgccggagt ataaatagag gcgcttcgtc tacggagcga caattcaatt caaacaagca     1620
aagtgaacac gtcgctaagc gaaagctaag caaataaaca agcgcagctg aacaagctaa     1680
acaatctgca gaagcttggt accctcgagc tcagctgaat tctggatcct ctagaccggt     1740
catatgcggc cgcggatcga tcgatatctg actaaatctt agtttgtatt gtcatgtttt     1800
aatacaatat gttatgttta aatatgtttt taataaattt tataaaataa tttcaacttt     1860
tattgtaaca acattgtcca tttacacact cctttcaagc gcgtgggact cgatgctcgg     1920
cgccactcaa aggcggtaat acggttatcc acagaatcag gggataacgc aggaaagaac     1980
atgtgagcaa aaggccagca aaaggccagg aaccgtaaaa aggccgcgtt gctggcgttt     2040
ttccataggc tccgcccccc tgacgagcat cacaaaaatc gacgctcaag tcagaggtgg     2100
cgaaacccga caggactata aagataccag gcgtttcccc ctggaagctc cctcgtgcgc     2160
tctcctgttc cgaccctgcc gcttaccgga tacctgtccg cctttctccc ttcgggaagc     2220
gtggcgcttt ctcaatgctc acgctgtagg tatctcagtt cggtgtaggt cgttcgctcc     2280
aagctgggct gtgtgcacga accccccgtt cagcccgacc gctgcgcctt atccggtaac     2340
```

```
tatcgtcttg agtccaaccc ggtaagacac gacttatcgc cactggcagc agccactggt    2400
aacaggatta gcagagcgag gtatgtaggc ggtgctacag agttcttgaa gtggtggcct    2460
aactacggct acactagaag gacagtattt ggtatctgcg ctctgctgaa gccagttacc    2520 ttcgaaaaa gagttggtag ctcttgatcc ggcaaacaaa ccaccgctgg tagcggtggt    2580 tttttgttt gcaagcagca gattacgcgc agaaaaaag gatctcaaga agatcctttg    2640
atcttttcta cggggtctga cgctcagtgg aacgaaaact cacgttaagg gattttgcat    2700
gcgctaagcg ggctttataa acgggctgcg ggaccagtt ttcatatcac taccgtttga    2760
gttcttgtgc tgtgtggata ctcctcccga caccgaatt                          2799

<210> SEQ ID NO 13
<211> LENGTH: 2709
<212> TYPE: DNA
<213> ORGANISM: Artificial Sequence
<220> FEATURE:
<223> OTHER INFORMATION: Vector

<400> SEQUENCE: 13
taattcggat ctctgcaagg gattttggtc atgaacaata aaactgtctg cttacataaa      60
cagtaataca aggggtgttc atagtataat acgactcact ataggagggc accatgacc    120 gagtacaagc ccaccgtgcg cctggccacc cgcgacgatg tgccacgcgc cgtgcgcacc    180
ctggccgccg cctttgccga ttatccagcc acccgccata ccgtggaccc cgatcgccat    240
attgagcgcg tgaccgagct gcaggagctg ttcctgaccc cgtgggcct ggatattggc    300 aaagtgtggg tggccgatga cggagccgcc gtggccgtgt ggaccacccc agagagtgtg    360
gaggccggag ccgtgttcgc cgagattgga ccacgcatgg ccgagctgag tggaagtcgc    420
ctggccgccc agcagcagat ggagggactg ctggccccac accgcccaaa ggagccagcc    480
tggtttctgg ccaccgtggg agtgtcccca gatcaccagg gaaagggact gggaagtgcc    540
gtggtgctgc caggcgtgga ggccgccgag cgcgccggcg tgccagcctt tctggagacc    600
agtgccccac gcaacctgcc cttttacgag cgcctgggct ttaccgtgac cgccgatgtg    660
gaggtgccag agggcccacg cacctggtgc atgacccgca agccaggcgc ctaagtcgac    720
ctcgaaactt gtttattgca gcttataatg gttacaaata aagcaatagc atcacaaatt    780
tcacaaataa agcattttt tcactgcatt ctagttgtgg tttgtccaaa ctcatcaatg    840
tatcttatca tgtcttcacg taataagtgt gcggctagca gtcaactact agtgaatgcc    900
ctactagaag atgtgtgttg cacaaaatgt ccctggaata accaatttga agtgcagata    960
gcagtaaacg taagctaata tgaatattat ttaactgtaa tgttttaata tcgctggaca   1020
ttactaataa accccactata aacacatgta catatgtatg ttttggcata caatgagtag   1080
ttggggaaaa aatgtgtaaa agcaccgtga ccatcacagc ataaagataa ccagctgaag   1140
tatcgaatat gagtaacccc caaattgaat cacatgccgc aactgatagg acccatggaa   1200
gtacactctt catggcgata tacaagacac acacaagcac gaacacccag ttgcggagga   1260
aattctccgt aaatgaaaac ccaatcggcg aacaattcat acccatatat ggtaaaagtt   1320
ttgaacgcga gcgaacttaa gagcgccgga gtataaatag aggcgcttcg tctacggagc   1380
gacaattcaa ttcaaacaag caaagtgaac acgtcgctaa gcgaaagcta agcaaataaa   1440
caagcgcagc tgaacaagct aaacaatctg cagaagcttg gtaccctcga gctcgtaagt   1500
atcaaggtta caagacaggt ttaaggagac caatagaaac tgggcttgtc gagacagaga   1560
```

```
agactcttgc gtttctgata ggcacctatt ggtcttactg acatccactt tgcctttctc    1620
tccacaggaa ttctggatcc tctagaccgg tcatatgcgg ccgcggatcg atcgatatct    1680
gactaaatct tagtttgtat tgtcatgttt aatacaata tgttatgttt aaatatgttt    1740
ttaataaatt ttataaaata atttcaactt ttattgtaac aacattgtcc atttacacac    1800
tcctttcaag cgcgtgggac tcgatgctcg gcgccactca aaggcggtaa tacggttatc    1860
cacagaatca ggggataacg caggaaagaa catgtgagca aaaggccagc aaaaggccag    1920
gaaccgtaaa aaggccgcgt tgctggcgtt tttccatagg ctccgccccc ctgacgagca    1980
tcacaaaaat cgacgctcaa gtcagaggtg gcgaaacccg acaggactat aaagatacca    2040
ggcgtttccc cctggaagct ccctcgtgcg ctctcctgtt ccgaccctgc cgcttaccgg    2100
atacctgtcc gcctttctcc cttcgggaag cgtggcgctt tctcaatgct cacgctgtag    2160
gtatctcagt tcggtgtagg tcgttcgctc caagctgggc tgtgtgcacg aaccccccgt    2220
tcagcccgac cgctgcgcct tatccggtaa ctatcgtctt gagtccaacc cggtaagaca    2280
cgacttatcg ccactggcag cagccactgg taacaggatt agcagagcga ggtatgtagg    2340
cggtgctaca gagttcttga agtggtggcc taactacggc tacactagaa ggacagtatt    2400
tggtatctgc gctctgctga agccagttac cttcggaaaa agagttggta gctcttgatc    2460
cggcaaacaa accaccgctg gtagcggtgg tttttttgtt tgcaagcagc agattacgcg    2520
cagaaaaaaa ggatctcaag aagatccttt gatcttttct acggggtctg acgctcagtg    2580
gaacgaaaac tcacgttaag ggattttgca tgcgctaagc gggctttata aacgggctg    2640 cgggaccagt tttcatatca ctaccgtttg agttcttgtg ctgtgtggat actcctcccg    2700
acaccgaat                                                             2709

<210> SEQ ID NO 14
<211> LENGTH: 5807
<212> TYPE: DNA
<213> ORGANISM: Artificial Sequence
<220> FEATURE:
<223> OTHER INFORMATION: Vector

<400> SEQUENCE: 14
cgtaagtatc aaggttacaa gacaggttta aggagaccaa tagaaactgg gcttgtcgag      60
acagagaaga ctcttgcgtt tctgataggc acctattggt cttactgaca tccactttgc     120
ctttctctcc acaggaattc gccaccatga gctgtgcat cctgctggcc gtggtggcct     180
tcgtgggact gagcctgggc atcgatctga tcgaggcat cttctacgag aagaacgaga     240
tcgacaagct gaccttcagc ctggatcacc gcgtgcgcga taacctgaag accgacctga     300
tcctgaacaa caacggcgag aacgattacg cctacctgaa caaatacgtg tacaccatcc     360
tgaaccgcga cagcaccgag aagatcaaga ccttcttcag ccacaacaag gacatgaagt     420
cctgcgacta cttcatcagc aaggagtaca acagcagcga caagaccaac cagatctgct     480
acaagaagac gttctgcggc gtcgtgatcc ccaacagcga ggagattaag acgaacaaga     540
tcaccaacga taagctgtac tgcgcccact caacagcac ccacatcatc atctactaca     600
tcagccagcc cctgctgctg gagccccacg tggtgtacga ggagaccttt ttcgagaagg     660
gcaagaacga ccagatcaac tgccagggca tgtacatctc cctgcgctcc gtgcatgtgc     720
acacccacaa cgccatcctg cagcaggaga ccctgaccta catcaagaac ctgtgcgacg     780
gcaagaacaa ctgcaagttc gacttcgaca gcattaagta cgagaacaag agcctgaccc     840
actacctgtt cttcatcaac atccagtacc agtgcatcag ccccctgaac ctgcaggaga     900
```

```
atgagatgtg cgacgtgtac aacgacgata cgcacaaggc cacgtgcaaa tacggcttca    960
acaagatcga gctgctgaag aatgtgtgcg aggagaacta ccgctgcacc caggatatct   1020
gcagcgtgaa ccagttctgc gacggcgaga atgagacctg cacgtgcaag accagcctgc   1080
tgcccagcgc caagaacaat tgcgagtaca cgatctgtg caccgtgctg aactgccccg    1140
agaactcgac ctgcgagcag atcggcaatg caagaaggc cgagtgcaag tgcgagaacg    1200
gcaagtacta ccacaacaac aagtgctaca ccaagaacga tctggagctg ccatcaaga    1260
ttgagcccca caagaaggag aagttctata agaacaacct gtaccagggc aaggccctga   1320
agcccgagta catcttcatg cagtgcgaga tggcttcag catcgaagtg atcaacgcct    1380
acgtgtcctg ctaccgcgtg tccttcaatc tgaacaagct gaaatacgtg accgagagcc   1440
tgaagaagat gtgcgacgga aagaccaagt gcgcctacgg caacaccatc gatcccatcg   1500
atgatctgaa ccaccacaac atctgcaaca acttcaacac gatctttaag tatgactacc   1560
tgtgcgtgtt caacaaccag aacatcaccct ccgacaagaa cagccatctg cacagcaaca  1620
tccccagcct gtacaactcc agcatcctgc ccgatatcaa caagagcaag ttccacctga   1680
tcagccgcaa cagccgcacc aaccagtacc ccacaacaa tatcagtatg ctggagatcc    1740
agaatgagat cagcagccac aactccaacc agttctccac cgatccccac accaactcga   1800
acaacatcaa caacatgaat atcaagaagg tggagatctt ccgcagccgc ttcagctcca   1860
agctgcagtg ccagggcggc aagatcaaca tcgacaaggc cattctgaag ggcggcgagg   1920
gctgcaatga tctgctgctg accaacagcc tgaagtccta ctgcaacgac ctgagcgagt   1980
gcgatatcgg cctgatctac cacttcgata cctactgcat caatgaccag tacctgttcg   2040
tgtcctacag ctgcagcaac ctgtgcaaca agtgccacaa caactccacg tgctacggca   2100
accgcttcaa ctacgattgc ttctgcgata ccccctacat ctcgaagtac ggaaacaagc   2160
tgtgcgagcg ccccaacgat tgcgagagcg tgctgtgctc ccagaaccaa gtgtgccaga   2220
tcctgccgaa tgataagctg atctgccagt gcgaggaggg ctacaagaac gtgaagggaa   2280
aatgcgtgcc ggataacaag tgcgatctga gctgccccag caacaaagtg tgcgtgatcg   2340
agaatggaaa gcagacctgc aagtgctccg agcgcttcgt gctggagaac ggcgtgtgca   2400
tctgcgccaa cgattacaag atggaggatg catcaactg cattgccaag aacaagtgca   2460
agcgcaagga gtacgagaat atctgcacca accccaacga tgtgcgcc tacaatgagg    2520
agaccgatat cgtgaagtgc gagtgcaagg agcactacta ccgcagcagc cgcggagagt   2580
gcattctgaa cgactactgc aaggacatca attgcaagga gaacgaggag tgcagcatcg   2640
tgaacttcaa gccagagtgc gtgtgcaagg agaacctgaa gaagaacaac aagggcgagt   2700
gcatctacga gaacagctgc ctgatcaacg agggcaactg ccccaaggat agcaagtgca   2760
tctatcgcga gtacaagccc cacgagtgcg tgtgcaacaa gcagggacac gtggccgtga   2820
atggcaaatg cgtgctggag ataagtgcg tgcacaacaa gaagtgcagc gagaacagca   2880
tctgcgtgaa cgtgatgaac aaggagccaa tctgcgtgtg cacctacaac tactacaaga   2940
aggacggcgt gtgcctgatc cagaacccct gcctgaagga taacggcggc tgctcccgca   3000
actccgagtg caccttcaag tacagcaaga tcaactgcac gtgcaaggag aactacaaga   3060
acaaggatga tagctgcgtg cccaacacga acgagtacga tgagagcttc accttccagt   3120
ataacgacga cgccagcatc atcctgggcg cctgcggcat gatcgagttc agctacatct   3180
acaaccagat tatctggaag attaacaact cgaaggagtc ctacgtgttc tactacgatt   3240
```

```
accccaccgc cggcaacatc gaggtgcaga ttaagaatga gattttccac acgatcatct    3300
atctgaagaa gaagatcggc aacagcgtga tctacgacga tttccaggtg gaccaccaga    3360
cctgcatcta tgagaatgtg ttttactaca gcaaccagaa tagcgcctgg tcccacccc     3420
agttcgagaa atgagcggcc gcggatcgat cgatatctga ctaaatctta gtttgtattg    3480
tcatgtttta atacaatatg ttatgtttaa atatgttttt aataaatttt ataaaataat    3540
ttcaacttttt attgtaacaa cattgtccat ttacacactc ctttcaagcg cgtgggactc   3600
gatgctcggc gccactcaaa ggcggtaata cggttatcca cagaatcagg ggataacgca    3660
ggaaagaaca tgtgagcaaa aggccagcaa aaggccagga accgtaaaaa ggccgcgttg    3720
ctggcgtttt tccataggct ccgcccccct gacgagcatc acaaaaatcg acgctcaagt    3780
cagaggtggc gaaacccgac aggactataa agataccagg cgtttccccc tggaagctcc    3840
ctcgtgcgct ctcctgttcc gaccctgccg cttaccggat acctgtccgc ctttctccct    3900
tcggaagcg tggcgctttc tcaatgctca cgctgtaggt atctcagttc ggtgtaggtc     3960
gttcgctcca agctgggctg tgtgcacgaa ccccccgttc agcccgaccg ctgcgcctta    4020
tccggtaact atcgtcttga gtccaacccg gtaagacacg acttatcgcc actggcagca    4080
gccactggta acaggattag cagagcgagg tatgtaggcg gtgctacaga gttcttgaag    4140
tggtggccta actacggcta cactagaagg acagtatttg gtatctgcgc tctgctgaag    4200
ccagttacct tcggaaaaag agttggtagc tcttgatccg gcaaacaaac caccgctggt    4260
agcggtggtt ttttgtttg caagcagcag attacgcgca gaaaaaaagg atctcaagaa     4320
gatcctttga tctttctac ggggtctgac gctcagtgga acgaaaactc acgttaaggg     4380
attttgcatg cgctaagcgg gctttataaa acgggctgcg ggaccagttt tcatatcact    4440
accgtttgag ttcttgtgct gtgtggatac tcctcccgac accgaattaa ttcggatctc    4500
tgcaagggat tttggtcatg aacaataaaa ctgtctgctt acataaacag taatacaagg    4560
ggtgttcata gtataatacg actcactata ggagggccac catggccaag ttgaccagtg    4620
ccgttccggt gctcaccgcg cgcgacgtcg ccggagcggt cgagttctgg accgaccggc    4680
tcgggttcag ccgggacttc gtggaggacg acttcgccgg tgtggtccgg gacgacgtga    4740
ccctgttcat cagcgcggtc caggaccagg tggtgccgga caacaccctg gcctgggtgt    4800
gggtgcgcgg cctggacgag ctgtacgccg agtggtcgga ggtcgtgtcc acgaacttcc    4860
gggacgcctc cgggccggcc atgaccgaga tcggcgagca gccgtggggg cgggagttcg    4920
ccctgcgcga cccggccggc aactgcgtgc acttcgtggc cgaggagcag gactgaccga    4980
cgccgaccaa caccgccggt ccgacggcgg cccacgggtc cagggggt cgacctcgaa      5040
acttgtttat tgcagcttat aatggttaca aataaagcaa tagcatcaca aatttcacaa    5100
ataaagcatt tttttcactg cattctagtt gtggtttgtc caaactcatc aatgtatctt    5160
atcatgtctt cacgtaataa gtgtgcggct agcagtcaac tactagtgaa tgccctacta    5220
gaagatgtgt gttgcacaaa atgtccctgg aataaccaat ttgaagtgca gatagcagta    5280
aacgtaagct aatatgaata ttatttaact gtaatgtttt aatatcgctg acattacta    5340
ataaacccac tataaacaca tgtacatatg tatgttttgg catacaatga gtagttgggg   5400
aaaaaatgtg taaaagcacc gtgaccatca cagcataaag ataaccagct gaagtatcga    5460
atatgagtaa ccccccaaatt gaatcacatg ccgcaactga taggacccat ggaagtacac    5520
tcttcatggc gatatacaag acacacacaa gcacgaacac ccagttgcgg aggaaattct    5580
ccgtaaatga aaacccaatc ggcgaacaat tcatacccat atatggtaaa agttttgaac    5640
```

```
gcgagcgaac ttaagagcgc cggagtataa atagaggcgc ttcgtctacg gagcgacaat   5700
tcaattcaaa caagcaaagt gaacacgtcg ctaagcgaaa gctaagcaaa taaacaagcg   5760
cagctgaaca agctaaacaa tctgcagaag cttggtaccc tcgagct                 5807

<210> SEQ ID NO 15
<211> LENGTH: 4135
<212> TYPE: DNA
<213> ORGANISM: Artificial Sequence
<220> FEATURE:
<223> OTHER INFORMATION: Vector

<400> SEQUENCE: 15
aattcggatc tctgcaaggg attttggtca tgaacaataa aactgtctgc ttacataaac     60
agtaatacaa ggggtgttca tagtataata cgactcacta taggagggcc accatgagcc    120
acatccagcg cgaaaccagc tgcagccgtc cgcgcctgaa cagcaacatg gatgccgatc    180
tgtacggcta caaatgggcc cgcgataacg tgggccagag cggcgctacc atctaccgcc    240
tgtacggcaa accggatgcc ccggaactgt tcctgaaaca cggcaaaggc agcgtggcca    300
acgatgtgac cgatgaaatg gtgcgcctga actggctgac cgagttcatg ccgctgccga    360
ccatcaaaca cttcatccgc accccggatg atgcctggct gctgaccacc gccattccgg    420
gcaaaaccgc cttccaggtg ctggaagaat acccggatag cggcgaaaac atcgtggatg    480
ccctggccgt gttcctgcgc cgcctgcaca gcatcccggt gtgcaactgc ccgttcaaca    540
gcgatcgcgt gttccgcctg gctcaggccc agagccgcat gaacaacggc ctggtggatg    600
ccagcgattt cgatgatgaa cgcaacggct ggccggtgga acaggtgtgg aaagagatgc    660
acaaactgct gccgttcagc ccggattccg tggtgaccca cggcgatttc agcctggata    720
acctgatctt cgatgagggc aaactgatcg gctgcatcga tgtgggccgc gtgggcattg    780
ccgatcgcta ccaggatctg gccatcctgt ggaactgcct gggcgagttc agcccgagcc    840
tgcagaaacg cctgttccag aagtacggca tcgataaccc ggatatgaac aaactgcagt    900
tccacctgat gctggatgag ttcttctaat aagtcgacct cgaaacttgt ttattgcagc    960
ttataatggt tacaaataaa gcaatagcat cacaaatttc acaaataaag catttttttc   1020
actgcattct agttgtggtt tgtccaaact catcaatgta tcttatcatg tcttcacgta   1080
ataagtgtgc ggctagcagt caactactag tgaatgccct actagaagat gtgtgttgca   1140
caaaatgtcc ctggaataac caatttgaag tgcagatagc agtaaacgta agctaatatg   1200
aatattattt aactgtaatg ttttaatatc gctggacatt actaataaac ccactataaa   1260
cacatgtaca tatgtatgtt ttggcataca atgagtagtt ggggaaaaaa tgtgtaaaag   1320
caccgtgacc atcacagcat aaagataacc agctgaagta tcgaatatga gtaaccccca   1380
aattgaatca catgccgcaa ctgataggac ccatggaagt acactcttca tggcgatata   1440
caagacacac acaagcacga cacccagtt gcggaggaaa ttctccgtaa atgaaaaccc   1500
aatcggcgaa caattcatac ccatatatgg taaaagtttt gaacgcgagc gaacttaaga   1560
gcgccggagt ataaatagag gcgcttcgtc tacggagcga caattcaatt caaacaagca   1620
aagtgaacac gtcgctaagc gaaagctaag caaataaaca gcgcagctg aacaagctaa    1680 acaatctgca gaagcttggt accctcgagc tcagctgaat tcgccaccat gaagctgtgc   1740
atcctgctgg ccgtggtggc cttcgtggga ctgagtctgg gcgacgtgaa gaacaacgag   1800
gactacaaga acgtggacta taagaatgtg aacttcctgc agtaccactt caaggagctg   1860
```

```
agcaactaca atatcgccaa cagcatcgac attctgcagg agaaggaggg ccacctggat    1920
ttcgtgatca tcccccacta caccttctg gactactaca agcacctgag ctacaactcc    1980
atctaccaca agagcagcac ctacggcaag tgcattgccg tggatgcctt catcaagaag    2040
atcaacgaga cctacgacaa agtgaagtcc aagtgcaacg acatcaagaa cgacctgatc    2100
gccacgatca agaagctgga gcaccctac gatatcaaca acaagaacga tgacagctac    2160
cgctacgaca tcagcgagga gatcgacgat aagtccgagg agacggacga cgagaccgag    2220
gaggtggagg atagcatcca ggataccgat agcaaccaca cccccagcaa caagaagaag    2280
aatgatctga tgaaccgcac ctttaagaag atgatggacg agtacaatac gaaaaagaag    2340
aagctgatca agtgcatcaa gaatcacgag aacgacttca acaagatctg catggacatg    2400
aagaactacg gcaccaacct gttcgagcag ctgtcctgct acaacaacaa cttctgcaac    2460
accaacggca tccgctacca ctacgatgag tacatccaca agctgatcct gagcgtgaag    2520
tcgaagaacc tgaacaagga tctgagcgac atgaccaaca tcctgcagca gagcgagctg    2580
ctgctgacca atctgaacaa gaagatgggc agctacatct acatcgacac catcaagttc    2640
attcacaagg agatgaagca catcttcaac cgcatcgagt accacaccaa gatcatcaac    2700
gacaagacga agatcattca ggacaagatc aagctgaaca tctggcgcac cttccagaag    2760
gatgagctgc tgaagcgcat cctggatatg agcaacgagt acagcctgtt catcaccagc    2820
gatcatctgc gccagatgct gtacaacacc ttctacagca aggagaagca cctgaacaac    2880
atcttccacc acctgatcta cgtgctgcag atgaagttca cgacgtgcc catcaagatg    2940 gagtacttcc agacctataa gaagaacaag cccctgaccc agcaccacca tcaccaccac    3000
aagcgccgct ggaagaagaa ctttatcgcc gtgtccgccg ccaaccgctt caagaagatt    3060
agcagcagcg agcccctgta ggcggccgcg gatcgatcga tatctgacta aatcttagtt    3120
tgtattgtca tgttttaata caatatgtta tgtttaaata tgtttttaat aaattttata    3180 aaataattc aacttttatt gtaacaacat tgtccattta cactcccttt caagcgcgt     3240 gggactcgat gctcggcgcc actcaaaggc ggtaatacgg ttatccacag aatcagggga    3300
taacgcagga aagaacatgt gagcaaaagg ccagcaaaag ccaggaacc gtaaaaaggc    3360 cgcgttgctg gcgttttcc ataggctccg cccccctgac gagcatcaca aaaatcgacg    3420
ctcaagtcag aggtggcgaa acccgacagg actataaaga taccaggcgt ttccccctgg    3480
aagctccctc gtgcgctctc ctgttccgac cctgccgctt accggatacc tgtccgcctt    3540
tctcccttcg ggaagcgtgg cgctttctca atgctcacgc tgtaggtatc tcagttcggt    3600
gtaggtcgtt cgctccaagc tgggctgtgt gcacgaaccc cccgttcagc ccgaccgctg    3660
cgccttatcc ggtaactatc gtcttgagtc caacccggta agacacgact tatcgccact    3720
ggcagcagcc actggtaaca ggattagcag agcgaggtat gtaggcggtg ctacagagtt    3780
cttgaagtgg tggcctaact acggctacac tagaaggaca gtatttggta tctgcgctct    3840
gctgaagcca gttaccttcg gaaaaagagt tggtagctct tgatccggca acaaaccac    3900 cgctggtagc ggtggttttt tgtttgcaa gcagcagatt acgcgcagaa aaaaggatc    3960 tcaagaagat cctttgatct tttctacggg gtctgacgct cagtggaacg aaaactcacg    4020
ttaagggatt ttgcatgcgc taagcgggct ttataaaacg ggctgcggga ccagttttca    4080
tatcactacc gtttgagttc ttgtgctgtg tggatactcc tcccgacacc gaatt         4135
```

<210> SEQ ID NO 16
<211> LENGTH: 3766

<212> TYPE: DNA
<213> ORGANISM: Artificial Sequence
<220> FEATURE:
<223> OTHER INFORMATION: Vector

<400> SEQUENCE: 16

| | | | | |
|---|---|---|---|---|
| taattcggat | ctctgcaagg | gattttggtc | atgaacaata | aaactgtctg cttacataaa | 60 |
| cagtaataca | aggggtgttc | atagtataat | acgactcact | ataggagggc caccatgacc | 120 |
| gagtacaagc | ccaccgtgcg | cctggccacc | cgcgacgatg | tgccacgcgc cgtgcgcacc | 180 |
| ctggccgccg | cctttgccga | ttatccagcc | acccgccata | ccgtggaccc cgatcgccat | 240 |
| attgagcgcg | tgaccgagct | gcaggagctg | ttcctgaccc | gcgtgggcct ggatattggc | 300 |
| aaagtgtggg | tggccgatga | cggagccgcc | gtggccgtgt | ggaccacccc agagagtgtg | 360 |
| gaggccggag | ccgtgttcgc | cgagattgga | ccacgcatgg | ccgagctgag tggaagtcgc | 420 |
| ctggccgccc | agcagcagat | ggagggactg | ctggccccac | accgcccaaa ggagccagcc | 480 |
| tggtttctgg | ccaccgtggg | agtgtcccca | gatcaccagg | gaaagggact gggaagtgcc | 540 |
| gtggtgctgc | caggcgtgga | ggccgccgag | cgcgccggcg | tgccagcctt tctggagacc | 600 |
| agtgccccac | gcaacctgcc | cttttacgag | cgcctgggct | ttaccgtgac cgccgatgtg | 660 |
| gaggtgccag | agggcccacg | cacctggtgc | atgacccgca | agccaggcgc ctaagtcgac | 720 |
| ctcgaaactt | gtttattgca | gcttataatg | gttacaaata | aagcaatagc atcacaaatt | 780 |
| tcacaaataa | agcatttttt | tcactgcatt | ctagttgtgg | tttgtccaaa ctcatcaatg | 840 |
| tatcttatca | tgtcttcacg | taataagtgt | gcggctagca | gtcaactact agtgaatgcc | 900 |
| ctactagaag | atgtgtgttg | cacaaaatgt | ccctggaata | accaatttga agtgcagata | 960 |
| gcagtaaacg | taagctaata | tgaatattat | ttaactgtaa | tgttttaata tcgctggaca | 1020 |
| ttactaataa | acccactata | aacacatgta | catatgtatg | ttttggcata caatgagtag | 1080 |
| ttggggaaaa | aatgtgtaaa | agcaccgtga | ccatcacagc | ataaagataa ccagctgaag | 1140 |
| tatcgaatat | gagtaacccc | caaattgaat | cacatgccgc | aactgatagg acccatggaa | 1200 |
| gtacactctt | catggcgata | tacaagacac | acacaagcac | gaacacccag ttgcggagga | 1260 |
| aattctccgt | aaatgaaaac | ccaatcggcg | aacaattcat | acccatatat ggtaaaagtt | 1320 |
| ttgaacgcga | gcgaacttaa | gagcgccgga | gtataaatag | aggcgcttcg tctacggagc | 1380 |
| gacaattcaa | ttcaaacaag | caaagtgaac | acgtcgctaa | gcgaaagcta agcaaataaa | 1440 |
| caagcgcagc | tgaacaagct | aaacaatctg | cagaagcttg | gtaccctcga gctcgtaagt | 1500 |
| atcaaggtta | caagacaggt | ttaaggagac | caatagaaac | tgggcttgtc gagacagaga | 1560 |
| agactcttgc | gtttctgata | ggcacctatt | ggtcttactg | acatccactt tgcctttctc | 1620 |
| tccacaggaa | ttcgccacca | tgaagctgtg | catcctgctg | gccgtggtgg ccttcgtggg | 1680 |
| actgagtctg | ggaagccgcc | acgtgttcat | ccgcaccgag | ctgagcttca tcaagaacaa | 1740 |
| cgtgccctgc | atccgcgaca | tgttcttcat | ctacaagcgc | gagctgtaca acatctgcct | 1800 |
| ggatgatctg | aagggcgagg | aggatgagac | ccacatctac | gtgcagaaga agtgaagga | 1860 |
| cagctggatc | accctgaacg | acctgttcaa | ggagaccgat | ctgaccggac gcccccacat | 1920 |
| cttcgcctac | gtgacgtgg | aggagatcat | cattctgctg | tgcgaggatg aggagttcag | 1980 |
| caaccgcaag | aaggatatga | cctgccaccg | cttctacagc | aacgatggca aggagtacaa | 2040 |
| caacagcgag | atcaccatca | gcgactacat | cctgaaggat | aagctgctgt ccagctacgt | 2100 |
| gtccctgccc | ctgaagatcg | agaaccgcga | gtacttcctg | atctgcggcg tgtcccccta | 2160 |

```
caagttcaag gatgataaca agaaggacga catcctgtgc atggccagcc acgataaggg    2220
cgagacctgg ggcaccaaga tcgtgattaa gtacgacaac tacaagctgg gcgtgcagta    2280
cttcttcctg cgcccctaca tcagcaagaa cgatctgagc ttccacttct acgtgggcga    2340
caacatcaac aacgtgaaga acgtgaactt catcgagtgc acccacgaga aggatctgga    2400
gttcgtgtgc tccaaccgcg attttctgaa ggacaacaag gtgctgcagg atgtgtccac    2460
cctgaatgat gagtacatcg tgtcctacgg caacgcaaca aacttcgccg agtgctacat    2520
cttcttcaac aacgagaaca gcatcctgat caagcccgag aagtacggca caccaccgc    2580 cggatgctac ggcggcacct tcgtgaagat tgatgagaac cgcacccctgt tcatctactc    2640 cagcagccag ggcatctaca acatccacac catctactac gccaactacg agcaccacca    2700
ccatcaccac taagcggccg cggatcgatc gatatctgac taaatcttag tttgtattgt    2760
catgttttaa tacaatatgt tatgtttaaa tatgttttta ataaattta taaaataatt    2820 tcaacttttta ttgtaacaac attgtccatt tacacactcc tttcaagcgc gtgggactcg    2880
atgctcggcg ccactcaaag gcggtaatac ggttatccac agaatcaggg gataacgcag    2940
gaaagaacat gtgagcaaaa ggccagcaaa aggccaggaa ccgtaaaaag gccgcgttgc    3000
tggcgttttt ccataggctc cgcccccctg acgagcatca caaaaatcga cgctcaagtc    3060
agaggtggcg aaacccgaca ggactataaa gataccaggc gtttccccct ggaagctccc    3120
tcgtgcgctc tcctgttccg accctgccgc ttaccggata cctgtccgcc tttctccctt    3180
cgggaagcgt ggcgctttct caatgctcac gctgtaggta tctcagttcg gtgtaggtcg    3240
ttcgctccaa gctgggctgt gtgcacgaac ccccgttca gcccgaccgc tgcgccttat    3300
ccggtaacta tcgtcttgag tccaacccgg taagacacga cttatcgcca ctggcagcag    3360
ccactggtaa caggattagc agagcgaggt atgtaggcgg tgctacagag ttcttgaagt    3420
ggtggcctaa ctacggctac actagaagga cagtatttgg tatctgcgct ctgctgaagc    3480 cagttaccctt cggaaaaaga gttggtagct cttgatccgg caaacaaacc accgctggta    3540
gcggtggttt ttttgtttgc aagcagcaga ttacgcgcag aaaaaaagga tctcaagaag    3600
atcctttgat cttttctacg gggtctgacg ctcagtggaa cgaaaactca cgttaaggga    3660
ttttgcatgc gctaagcggg cttttataaaa cgggctgcgg gaccagtttt catatcacta    3720
ccgtttgagt tcttgtgctg tgtggatact cctcccgaca ccgaat            3766
```

<210> SEQ ID NO 17  
<211> LENGTH: 4220  
<212> TYPE: DNA  
<213> ORGANISM: Artificial Sequence  
<220> FEATURE:  
<223> OTHER INFORMATION: Vector

<400> SEQUENCE: 17

```
cgtaagtatc aaggttacaa gacaggttta aggagaccaa tagaaactgg gcttgtcgag      60
acagagaaga ctcttgcgtt tctgataggc acctattggt cttactgaca tccactttgc     120 cttttctctcc acaggaattc gccaccatga agctgtgcat cctgctggcc gtggtggcct    180
tcgtgggact gagtctggga caggaggccg tgccagagga gagcaccgag attgccacc     240 gcaccgagac ccgcaccgat gagcgcaaga atcaggagcc cgccaacaag gatctgaaga    300
acccccagca gagcgtgggc gagaacggcc gaaggatct gctgcaggag gatctgggag    360
gcagccgcag cgaggatgaa gtgacccagg agttcgcgt gaaccacggc atccccaagg    420
gcgaggatca gaccctggga aagtccgatg ccatccccaa catcggcgag cccgagaccg    480
```

```
gaatcagtac caccgaggag tcccgccacg aggagggcca taacaagcag gccctgagca    540
cctccgtgga tgagcccgag ctgagcgata ccctgcagct gcacgaggat accaaggaga    600
acgataagct gccctggag agcagcacca tcaccagccc aaccgagagc ggcagcagcg     660
ataccgagga gaccccatcc attagcgagg cccgaaggg caacgagcag aagaagcgcg     720
acgacgatag cctgagcaag atcagcgtgt ccccgagaa cagccgccca gagaccgatg     780
ccaaggatac cagcaacctg ctgaagctga agggcgacgt ggacatcagc atgcccaagg    840
ccgtgatcgg cagctccccc aacgataaca tcaacgtgac cgagcagggc gacaacatct    900
cgggcgtgaa cagcaagccc ctgtccgatg atgtgcgccc cgataagaac catgaggaag    960
tgaaggagca caccagcaac agcgataacg tgcagcagtc cggcggcatc gtgaacatga   1020
acgtggagaa ggagctgaag gacaccctgg agaaccccag ctccagcctg gatgagggaa   1080
aggcccatga ggagctgtcc gagcccaacc tgtccagcga tcaggatatg agcaacaccc   1140 caggcccct ggataacacc tcggaggaga cgaccgagcg catcagcaac aacgagtaca    1200
aagtgaacga gcgcgagggc gagcgcaccc tgaccaagga gtatgaggat atcgtgctga   1260
agtcccacat gaaccgcgag agcgacgatg gcgagctgta cgatgagaac agcgatctga   1320
gcaccgtgaa cgatgagtcc gaggatgccg aggccaagat gaagggcaat gataccagcg   1380
agatgagcca caacagcagc cagcacatcg agagcgatca gcagaagaac gatatgaaga   1440
ccgtgggcga cctgggcacc acccacgtgc agaatgagat ctccgtgccc gtgaccggcg   1500
agatcgatga gaagctgcgc gagagcaagg agtccaagat ccacaaggcc gaggaggagc   1560
gcctgagcca caccgatatc cacaagatca accccgagga tcgcaactcc aacaccctgc   1620
acctgaagga tatccgcaac gaggagaatg agcgccacct gacgaaccag aacatcaaca   1680
tcagccagga gcgcgacctg cagaagcacg gcttccacac catgaacaac ctgcacggcg   1740
acggcgtgtc cgagcgcagc cagatcaatc actcgcacca cggcaaccgc caggatcgcg   1800
gaggaaatag tggaagcgcc tggtcccacc cccagttcga gaaatgagcg gccgcggatc   1860
gatcgatatc tgactaaatc ttagtttgta ttgtcatgtt ttaatacaat atgttatgtt   1920
taaatatgtt tttaataaat tttataaaat aatttcaact tttattgtaa caacattgtc   1980
catttacaca ctcctttcaa gcgcgtggga ctcgatgctc ggcgccactc aaaggcggta   2040
atacggttat ccacagaatc aggggataac gcaggaaaga acatgtgagc aaaaggccag   2100
caaaaggcca ggaaccgtaa aaaggccgcg ttgctggcgt ttttccatag gctccgcccc   2160
cctgacgagc atcacaaaaa tcgacgctca agtcagaggt ggcgaaaccc gacaggacta   2220
taaagatacc aggcgtttcc ccctggaagc tccctcgtgc gctctcctgt tccgaccctg   2280
ccgcttaccg gatacctgtc cgcctttctc ccttcgggaa gcgtggcgct ttctcaatgc   2340
tcacgctgta ggtatctcag ttcggtgtag tcgttcgct ccaagctggg ctgtgtgcac    2400
gaaccccccg ttcagcccga ccgctgcgcc ttatccggta actatcgtct tgagtccaac   2460
ccggtaagac acgacttatc gccactggca gcagccactg gtaacaggat tagcagagcg   2520
aggtatgtag gcggtgctac agagttcttg aagtggtggc ctaactacgg ctacactaga   2580
aggacagtat ttggtatctg cgctctgctg aagccagtta ccttcggaaa aagagttggt   2640
agctcttgat ccggcaaaca aaccaccgct ggtagcggtg gttttttgt ttgcaagcag    2700 cagattacgc gcagaaaaaa aggatctcaa gaagatcctt tgatcttttc tacgggtct    2760 gacgctcagt ggaacgaaaa ctcacgttaa gggattttgc atgcgctaag cgggctttat   2820
```

-continued

```
aaaacgggct gcgggaccag ttttcatatc actaccgttt gagttcttgt gctgtgtgga    2880
tactcctccc gacaccgaat taattcggat ctctgcaagg gatttggtc atgaacaata      2940 aaactgtctg cttacataaa cagtaataca aggggtgttc atagtataat acgactcact    3000
ataggagggc caccatggcc aagttgacca gtgccgttcc ggtgctcacc gcgcgcgacg    3060
tcgccggagc ggtcgagttc tggaccgacc ggctcgggtt cagccgggac ttcgtggagg    3120
acgacttcgc cggtgtggtc cgggacgacg tgaccctgtt catcagcgcg gtccaggacc    3180
aggtggtgcc ggacaacacc ctggcctggg tgtgggtgcg cggcctggac gagctgtacg    3240
ccgagtggtc ggaggtcgtg tccacgaact tccgggacgc ctccgggccg gccatgaccg    3300
agatcggcga gcagccgtgg gggcgggagt tcgccctgcg cgacccggcc ggcaactgcg    3360
tgcacttcgt ggccgaggag caggactgac cgacgccgac caacaccgcc ggtccgacgg    3420
cggcccacgg gtcccagggg ggtcgacctc gaaacttgtt tattgcagct tataatggtt    3480
acaaataaag caatagcatc acaaatttca caaataaagc attttttca ctgcattcta     3540 gttgtggttt gtccaaactc atcaatgtat cttatcatgt cttcacgtaa taagtgtgcg    3600
gctagcagtc aactactagt gaatgcccta ctagaagatg tgtgttgcac aaaatgtccc    3660
tggaataacc aatttgaagt gcagatagca gtaaacgtaa gctaatatga atattattta    3720
actgtaatgt tttaatatcg ctggacatta ctaataaacc cactataaac acatgtacat    3780
atgtatgttt tggcatacaa tgagtagttg gggaaaaaat gtgtaaaagc accgtgacca    3840
tcacagcata aagataacca gctgaagtat cgaatatgag taacccccaa attgaatcac    3900
atgccgcaac tgataggacc catggaagta cactcttcat ggcgatatac aagcacaca    3960 caagcacgaa cacccagttg cggaggaaat tctccgtaaa tgaaaccca atcggcgaac    4020 aattcatacc catatatggt aaaagttttg aacgcgagcg aacttaagag cgccggagta    4080
taaatagagg cgcttcgtct acggagcgac aattcaattc aaacaagcaa agtgaacacg    4140
tcgctaagcg aaagctaagc aaataaacaa gcgcagctga acaagctaaa caatctgcag    4200
aagcttggta ccctcgagct                                                4220
```

<210> SEQ ID NO 18
<211> LENGTH: 400
<212> TYPE: PRT
<213> ORGANISM: Plasmodium falciparum

<400> SEQUENCE: 18

```
Asp Val Lys Asn Asn Glu Asp Tyr Lys Asn Val Asp Tyr Lys Asn Val
1               5                   10                  15

Asn Phe Leu Gln Tyr His Phe Lys Glu Leu Ser Asn Tyr Asn Ile Ala
            20                  25                  30

Asn Ser Ile Asp Ile Leu Gln Glu Lys Glu Gly His Leu Asp Phe Val
        35                  40                  45

Ile Ile Pro His Tyr Thr Phe Leu Asp Tyr Tyr Lys His Leu Ser Tyr
    50                  55                  60

Asn Ser Ile Tyr His Lys Ser Ser Thr Tyr Gly Lys Cys Ile Ala Val
65                  70                  75                  80

Asp Ala Phe Ile Lys Lys Ile Asn Glu Thr Tyr Asp Lys Val Lys Ser
                85                  90                  95

Lys Cys Asn Asp Ile Lys Asn Asp Leu Ile Ala Thr Ile Lys Lys Leu
            100                 105                 110

Glu His Pro Tyr Asp Ile Asn Asn Lys Asn Asp Asp Ser Tyr Arg Tyr
        115                 120                 125
```

Asp Ile Ser Glu Glu Ile Asp Lys Ser Glu Thr Asp Asp Glu
    130                 135                 140

Thr Glu Glu Val Glu Asp Ser Ile Gln Asp Thr Asp Ser Asn His Thr
145                 150                 155                 160

Pro Ser Asn Lys Lys Asn Asp Leu Met Asn Arg Thr Phe Lys Lys
                165                 170                 175

Met Met Asp Glu Tyr Asn Thr Lys Lys Lys Leu Ile Lys Cys Ile
            180                 185                 190

Lys Asn His Glu Asn Asp Phe Asn Lys Ile Cys Met Asp Met Lys Asn
        195                 200                 205

Tyr Gly Thr Asn Leu Phe Glu Gln Leu Ser Cys Tyr Asn Asn Phe
210                 215                 220

Cys Asn Thr Asn Gly Ile Arg Tyr His Tyr Asp Glu Tyr Ile His Lys
225                 230                 235                 240

Leu Ile Leu Ser Val Lys Ser Lys Asn Leu Asn Lys Asp Leu Ser Asp
                245                 250                 255

Met Thr Asn Ile Leu Gln Gln Ser Glu Leu Leu Thr Asn Leu Asn
            260                 265                 270

Lys Lys Met Gly Ser Tyr Ile Tyr Ile Asp Thr Ile Lys Phe Ile His
        275                 280                 285

Lys Glu Met Lys His Ile Phe Asn Arg Ile Glu Tyr His Thr Lys Ile
290                 295                 300

Ile Asn Asp Lys Thr Lys Ile Ile Gln Asp Lys Ile Lys Leu Asn Ile
305                 310                 315                 320

Trp Arg Thr Phe Gln Lys Asp Glu Leu Leu Lys Arg Ile Leu Asp Met
                325                 330                 335

Ser Asn Glu Tyr Ser Leu Phe Ile Thr Ser Asp His Leu Arg Gln Met
            340                 345                 350

Leu Tyr Asn Thr Phe Tyr Ser Lys Glu Lys His Leu Asn Asn Ile Phe
        355                 360                 365

His His Leu Ile Tyr Val Leu Gln Met Lys Phe Asn Asp Val Pro Ile
370                 375                 380

Lys Met Glu Tyr Phe Gln Thr Tyr Lys Lys Asn Lys Pro Leu Thr Gln
385                 390                 395                 400

<210> SEQ ID NO 19
<211> LENGTH: 18
<212> TYPE: DNA
<213> ORGANISM: Artificial Sequence
<220> FEATURE:
<223> OTHER INFORMATION: Expression tag

<400> SEQUENCE: 19
caccaccatc accaccac                                                    18

<210> SEQ ID NO 20
<211> LENGTH: 24
<212> TYPE: DNA
<213> ORGANISM: Artificial Sequence
<220> FEATURE:
<223> OTHER INFORMATION: Expression tag

<400> SEQUENCE: 20
tggtcccacc cccagttcga gaaa                                             24

<210> SEQ ID NO 21
<211> LENGTH: 54

<212> TYPE: DNA
<213> ORGANISM: Artificial Sequence
<220> FEATURE:
<223> OTHER INFORMATION: Expression tag

<400> SEQUENCE: 21
atgaagctgt gcatcctgct ggccgtggtg gccttcgtgg gactgagtct ggga    54

<210> SEQ ID NO 22
<211> LENGTH: 24
<212> TYPE: DNA
<213> ORGANISM: Artificial Sequence
<220> FEATURE:
<223> OTHER INFORMATION: Expression tag

<400> SEQUENCE: 22
gactacaagg atgacgacga caag    24

<210> SEQ ID NO 23
<211> LENGTH: 6
<212> TYPE: PRT
<213> ORGANISM: Artificial Sequence
<220> FEATURE:
<223> OTHER INFORMATION: Expression tag

<400> SEQUENCE: 23

His His His His His His
1               5

<210> SEQ ID NO 24
<211> LENGTH: 8
<212> TYPE: PRT
<213> ORGANISM: Artificial Sequence
<220> FEATURE:
<223> OTHER INFORMATION: Expression tag

<400> SEQUENCE: 24

Trp Ser His Pro Gln Phe Glu Lys
1               5

<210> SEQ ID NO 25
<211> LENGTH: 18
<212> TYPE: PRT
<213> ORGANISM: Artificial Sequence
<220> FEATURE:
<223> OTHER INFORMATION: Expression tag

<400> SEQUENCE: 25

Met Lys Leu Cys Ile Leu Leu Ala Val Val Ala Phe Val Gly Leu Ser
1               5                   10                  15

Leu Gly

<210> SEQ ID NO 26
<211> LENGTH: 8
<212> TYPE: PRT
<213> ORGANISM: Artificial Sequence
<220> FEATURE:
<223> OTHER INFORMATION: Expression tag

<400> SEQUENCE: 26

Asp Tyr Lys Asp Asp Asp Asp Lys
1               5

<210> SEQ ID NO 27
<211> LENGTH: 511
<212> TYPE: PRT

<213> ORGANISM: Plasmodium falciparum

<400> SEQUENCE: 27

```
Gln Glu Ala Val Pro Glu Glu Ser Thr Glu Ile Ala His Arg Thr Glu
  1               5                  10                  15

Thr Arg Thr Asp Glu Arg Lys Asn Gln Glu Pro Ala Asn Lys Asp Leu
             20                  25                  30

Lys Asn Pro Gln Gln Ser Val Gly Glu Asn Gly Thr Lys Asp Leu Leu
         35                  40                  45

Gln Glu Asp Leu Gly Gly Ser Arg Ser Glu Asp Glu Val Thr Gln Glu
 50                  55                  60

Phe Gly Val Asn His Gly Ile Pro Lys Gly Glu Asp Gln Thr Leu Gly
 65                  70                  75                  80

Lys Ser Asp Ala Ile Pro Asn Ile Gly Glu Pro Glu Thr Gly Ile Ser
             85                  90                  95

Thr Thr Glu Glu Ser Arg His Glu Gly His Asn Lys Gln Ala Leu
         100                 105                 110

Ser Thr Ser Val Asp Glu Pro Glu Leu Ser Asp Thr Leu Gln Leu His
         115                 120                 125

Glu Asp Thr Lys Glu Asn Asp Lys Leu Pro Leu Glu Ser Ser Thr Ile
130                 135                 140

Thr Ser Pro Thr Glu Ser Gly Ser Ser Asp Thr Glu Glu Thr Pro Ser
145                 150                 155                 160

Ile Ser Glu Gly Pro Lys Gly Asn Glu Gln Lys Lys Arg Asp Asp Asp
                 165                 170                 175

Ser Leu Ser Lys Ile Ser Val Ser Pro Glu Asn Ser Arg Pro Glu Thr
             180                 185                 190

Asp Ala Lys Asp Thr Ser Asn Leu Leu Lys Leu Lys Gly Asp Val Asp
         195                 200                 205

Ile Ser Met Pro Lys Ala Val Ile Gly Ser Ser Pro Asn Asp Asn Ile
210                 215                 220

Asn Val Thr Glu Gln Gly Asp Asn Ile Ser Gly Val Asn Ser Lys Pro
225                 230                 235                 240

Leu Ser Asp Asp Val Arg Pro Asp Lys Asn His Glu Glu Val Lys Glu
                 245                 250                 255

His Thr Ser Asn Ser Asp Asn Val Gln Gln Ser Gly Gly Ile Val Asn
             260                 265                 270

Met Asn Val Glu Lys Glu Leu Lys Asp Thr Leu Glu Asn Pro Ser Ser
         275                 280                 285

Ser Leu Asp Glu Gly Lys Ala His Glu Glu Leu Ser Glu Pro Asn Leu
290                 295                 300

Ser Ser Asp Gln Asp Met Ser Asn Thr Pro Gly Pro Leu Asp Asn Thr
305                 310                 315                 320

Ser Glu Glu Thr Thr Glu Arg Ile Ser Asn Asn Glu Tyr Lys Val Asn
                 325                 330                 335

Glu Arg Glu Gly Glu Arg Thr Leu Thr Lys Glu Tyr Glu Asp Ile Val
             340                 345                 350

Leu Lys Ser His Met Asn Arg Glu Ser Asp Asp Gly Glu Leu Tyr Asp
         355                 360                 365

Glu Asn Ser Asp Leu Ser Thr Val Asn Asp Glu Ser Glu Asp Ala Glu
370                 375                 380

Ala Lys Met Lys Gly Asn Asp Thr Ser Glu Met Ser His Asn Ser Ser
385                 390                 395                 400
```

-continued

```
Gln His Ile Glu Ser Asp Gln Gln Lys Asn Asp Met Lys Thr Val Gly
                405                 410                 415

Asp Leu Gly Thr Thr His Val Gln Asn Glu Ile Ser Val Pro Val Thr
            420                 425                 430

Gly Glu Ile Asp Glu Lys Leu Arg Glu Ser Lys Glu Ser Lys Ile His
        435                 440                 445

Lys Ala Glu Glu Glu Arg Leu Ser His Thr Asp Ile His Lys Ile Asn
    450                 455                 460

Pro Glu Asp Arg Asn Ser Asn Thr Leu His Leu Lys Asp Ile Arg Asn
465                 470                 475                 480

Glu Glu Asn Glu Arg His Leu Thr Asn Gln Asn Ile Asn Ile Ser Gln
                485                 490                 495

Glu Arg Asp Leu Gln Lys His Gly Phe His Thr Met Asn Asn Leu
            500                 505                 510
```

MALARIA VACCINE AND METHODS FOR PRODUCING SAME

CROSS REFERENCE TO RELATED APPLICATIONS

The present invention is a national stage application which claims priority from PCT Application No. PCT/AU2018/050155 filed Feb. 23, 2018, and AU Application No. AU2017900648 filed Feb. 27, 2017. Applicants claim the benefits of 35 U.S.C. § 120 as to the said PCT application, and priority under 35 U.S.C. § 119 as to the said AU application, and the entire disclosures of all applications are incorporated herein by reference in their entireties.

CROSS REFERENCE TO RELATED APPLICATIONS

The present invention is a national stage application which claims priority from PCT Application No. PCT/AU2018/050155 filed Feb. 23, 2018, and AU Application No. AU2017900648 filed Feb. 27, 2017. Applicants claim the benefits of 35 U.S.C. § 120 as to the said PCT application, and priority under 35 U.S.C. § 119 as to the said AU application, and the entire disclosures of all applications are incorporated herein by reference in their entireties.

FIELD

The present description relates to malaria vaccines comprising *Plasmodium falciparum* (Pf) polypeptides and methods of producing the same.

BACKGROUND

Bibliographic details of references in the subject specification are also listed at the end of the specification.

Reference to any prior art in this specification is not, and should not be taken as, acknowledgement or any form of suggestion that this prior art forms part of the common general knowledge in any country.

Malaria in man is a tropical disease resulting from infection by one celled protozoan parasites of the genus *Plasmodium* which are deposited in to the blood stream when an infected mosquito takes a blood meal. *Plasmodium falciparum* and *Plasmodium vivax* are responsible for the most common and severe forms of malaria and despite recent significant reductions in the frequency of infection and deaths, last year it is estimated that over 200 million people were affected with approximately 400,000 deaths. Children in sub-Saharan Africa are particularly vulnerable to *P. falciparum* and account for most deaths from malaria. The parasite undergo a complex life cycle in man with rounds of infection and replication in erythrocytes or reticulocytes causing many of the early clinical symptoms of malaria, i.e., fever, shaking chills, headache, malaise, myalgia and fatigue. Current guidelines suggest that all new subjects with *P. falciparum* malaria should be admitted to hospital initially because of the speed with which patients can worse.

Subunit malaria vaccines are still in development 20 years after they were widely heralded as the most promising way forward for protecting vulnerable populations from Malaria. Much research has been undertaken during this period and knowledge concerning the molecular immunobiology of the host parasite relationship has accumulated. There are currently no available vaccines for malaria. The most advanced vaccine currently undergoing development is RTS,S which targets the liver stages of the parasite life cycle.

Another proposed vaccine approach is to target blood stage (merozoite) parasites. A large number of proteins are produced by the merozoite stage of the parasite that congregate at least in part at the apical end or complex of the merozoite prior to or at the time of erythrocyte engagement. *Plasmodium* merozoite proteins also form erythrocyte cell surface proteins that act as receptors for the invading merozoite. Illustrative merozoite proteins include MSP1, MSP2, MSP4, MSP5, MSP10, Pf12, Pf38, Pf92, Pf113, ASP, RAMA, EBA140, EBA175, EBA181, EBL1, AMA1, MTRAP, MSP5, MSP6, H101, H103, MSP7, Pf41, RAP1, RAP2, RAPS, RHopH1, RhopH3, Rh1, Rh4, Rh2b, Rh5, SPATR, PTRAMP, TLP, Pf34, PF14_0344, PF10_0323, PFF0335c, AARP, MSP3.4, MSP3.8, MSRP1, MSRP2, MSRP3, RON1, RON2, 4, 5 and 8) RON3, RON6, Pf12p, MSP5, GAMA, and PF11_0373. The merozoite surface proteins (MSPs) are thought to function early in merozoite invasion (a process which takes place in less than two minutes) and are highly polymorphic. The erythrocyte binding antigens (PfEBAs) and reticulocyte binding protein (PfRHs) are related to *P. virax* duffy binding proteins/reticulocyte binding proteins respectively and they orchestrate a variety of interations that result in host cell invasion by poorly defined pathways that display strain specific permutations. RH5 is more conserved PfRH merozoite secreted protein that binds the Ok blood group antigen, basagin. Improtantly antibodies raised against RH5 are able to prevent parasite growth in vitro and the blocking effect is not strain specific. In this case, the ability to produce a immunogenic RH5 able to engender inhibitory antibodies has been a problem for vaccine developers. Others have looked at the ability of antibodies against other merozoite proteins to enhance invasion blocking and found, for example that antibodies against PfRH4 and PfRH5 work synergistically to enhance invasion blocking effects.

These molecules are proposed as vaccine candidates based on their surface location as extracellular proteins and/or proposed role in host cell invasion and development within the host cell. One of the problems with this approach generally is the antigenic variability or allele polymorphism of the blood stage antigens which limits the ability of one allele of the protein to protect against different alleles present in the population of *Plasmodium* alleles. Another problem is redundancy in the host invasion pathway which means that blocking one pathway may not affect merozoite invasion levels.

Another set of problems faced by malaria vaccine developers in the field is the production of adequate amount of protein in a suitable form. For example, *Plasmodium* polynucleotides have a very high A:T content which leads to low codon usage compatibility in heterologous expression systems. The large size of some of these proteins and the presence of long stretches of repetitive amino acid sequences also hampers their expression in heterologous expression systems. Endogenous *Plasmodium* proteins are not modified by N-linked glycans thus expression in most available eukaryotic expression systems may lead to inappropriate or non-native glycosylations or disulfide bonding which foreshadow unpredictable effects on the immunogenicity of vaccine candidates. One approach with membrane proteins has been to express hydrophilic ectodomains without the more hydrophobic domain, or to express only about 200 bp fragments of the ectodomain recombinantly.

Accordingly, it remains challenging to develop and produce *Plasmodium* derived antigens, including modified or truncated forms that are able to engender effective immunity against blood stage forms of the parasite.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps. By "consisting of" is meant including, and limited to, whatever follows the phrase "consisting of. Thus, the phrase "consisting of" indicates that the listed elements are required or mandatory, and that no other elements may be present. By "consisting essentially of is meant including any elements listed after the phrase, and limited to other elements that do not interfere with or contribute to the activity or action specified in the disclosure for the listed elements. Thus, the phrase "consisting essentially of indicates that the listed elements are required or mandatory, but that no other elements are optional and may or may not be present depending upon whether or not they affect the activity or action of the listed elements.

As used herein the singular forms "a", "an" and "the" include plural aspects unless the context clearly dictates otherwise. Thus, for example, reference to "a composition" includes a single composition, as well as two or more compositions; reference to "an agent" includes one agent, as well as two or more agents; reference to "the disclosure" includes single and multiple aspects of the disclosure and so forth.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of sequence identifiers is provided after the brief description of the drawings. A sequence listing is provided after the claims.

*Plasmodium falciparum* (Pf) Ripr polypeptide is a peripheral membrane protein of over 1000 amino acids comprising 10 EGF domains mostly at the C-terminal portion of the polypeptide. EGF domains comprise multiple conserved cysteine residues which can lead to complex aggregate or multimer formation upon expression in vitro. Such polypeptides are typically difficult to express in prokaryotic expression systems and when expressed in *E. coli*, the present inventors identified that antibodies produced against the polypeptide were not inhibitory.

In one embodiment, the specification provides a modified arthropoda cell, modified to express a *Plasmodium falciparum* (Pf) Ripr polypeptide from a heterologous polynucleotide encoding a PfRipr polypeptide. In one embodiment, the cell is an insect cell. In one embodiment, the heterologous polypeptide comprises at least initially (prior to cleavage) a suitable signal sequence. In one embodiment, the polynucleotide is operably linked to an expression control sequence which induces PfRipr polypeptide expression in the cell. As determined herein, PfRipr polypeptide expressed in the insect cell induces parasite invasion inhibitory antibodies when administered to a subject.

In one embodiment, the specification provides a modified *Drosophila* derived cell modified to over express a *Plasmodium falciparum* (Pf) Ripr polypeptide (antigen) from a heterologous polynucleotide encoding a PfRipr polypeptide. In one embodiment, the heterologous polypeptide comprises at least initially (prior to cleavage) a suitable signal sequence. In one embodiment, the signal sequences is an insect signal sequence to direct the polypeptide through the host cell secretory pathway. In one embodiment, the polynucleotide is operably linked to an expression control sequence which induces PfRipr polypeptide expression in the cell. In one embodiment, insect promoter sequences are routinely employed. As determined herein, PfRipr polypeptide expressed in the *Drosophila* cell induces parasite and specifically merozoite invasion inhibitory antibodies when administered to a subject.

An illustrative *Drosophila* derived cell is a *Drosophila melanogaster* derived cell, such as a Scheider 2 cell line (S2), S3 cells or a derivative of the Kc cell line used for recombinant protein production. A wide variety of vectors in general allow for stable expression of recombinant proteins in insect cells. However, the production of such a large full length PfRipr polypeptide in *Drosophila* derived S2 cells was not a routine matter.

Other insect host cell expression systems are known in the art and include *Spodoptera frugiperda* derived cells, such as Sf9, Sf21 cell lines. Many types of viruses can infect insect cells and Baculovirus expression systems are widely employed to express recombinant proteins transiently or stably in insect cells.

Illustrative signal sequences include the insect BiP leader sequence, the honeybee melittin, signal peptide. As known to those of skill in the art, co-expression of BiP/Grp78 with a protein disulfide isomerase can enhance secreted expression in insect cells. Putative optimal signal sequences are tested to determine the optimal performance.

In one embodiment, the Pf polypeptides are expressed as soluble non-aggregated forms.

Expression may be transient or stable. Based upon the present disclosure, a wide range of selection procedures are known in the art to identify stable cell lines expressing high levels of antigenic Pf polypeptide, including a PfRipr polypeptide, and a PfRH5 polypeptide and a PfCyrPa polypeptide.

Expression control sequences promote optimal transcription, processing, RNA export and translation of the subject Pf polypeptide/s. Transcription regulatory sequences, i.e., promoters/enhancers are selected for high levels of transcription. Putative optimal expression control sequences are tested to determine the optimal performance. Illustrative promoters include the actin 5 promoter, and PpIE promoters, OpIE (OpIE1/OpIE2 for example) promoters, and KanR promoters.

In one embodiment, the insect cell line grows in suspension, is tolerant to osmolarity changes, and does not require $CO_2$ for cultivation. Protein is expressed into the culture media without requirement for cell lysis and thus purification steps are reduced.

Reference herein to a *Plasmodium* "polypeptide", includes reference to an "antigen" or "one or more epitopes" and refers to proteins or parts or portions thereof that comprise naturally occurring amino acid sequences, alleles, recombinantly produced modified forms, processed products, or modified or truncated (biologically active fragments) forms thereof which induce antibodies in a subject that are effective in inhibiting the invasion of host cells by merozoites. In one embodiment the Pf polypeptide is a polypeptide that is secreted from the merozoite. Illustrative truncated forms include the ectodomain together with all or part of a transmembrane domain/GPI anchor. Illustrative modified forms include polypeptides with one or more amino acid deleted, substituted or modified. In one embodiment, modified or truncated forms essentially retain or improve on the antigenicity and/or stability of the unmodified or naturally occurring polypeptide sequence. Modified forms may be modified to ensure certain host cell post-translational modifications are avoided or reduced in the Pf polypeptide while others are enhanced to allow optimal folding and antigenicity. In one illustrative embodiment, modified forms may have amino acid substitutions, for example to Ala or Gly, to reduce host cell glycosylation events or to enhance stability for example in the case of unpaired cysteines.

In one embodiment, modified and truncated forms of *Plasmodium* polypeptides display at least one characteristic selected from the group comprising (i) reduced binding to non-invasion inhibitory antibodies, (ii) at least substantially the same binding to invasion inhibitory antibodies, (iii) elicits the production of lower titers of non-neutralizing antibodies than invasion inhibitory antibodies, (iv) elicits the production of invasion inhibitory antibodies, (v) elicits the production of broadly invasion inhibitory antibodies against more than one allele of the antigen/s, (vi) optionally elicits the production of higher titers of invasion inhibitory antibodies; and (vii) optionally elicits the production of high titers of broadly invasion inhibitory antibodies. Specifically, in one embodiment a modified or truncated polypeptide displays an enhanced ability relative to the unmodified form to elicit antibodies that facilitate invasion inhibition. Inhibition by an antibody includes complete inhibition of invasion and a significant reduction in invasion such as 70%, 65%, 60%, 55%, 50%, 45%, 40%, 35%, 30% or less than 30% invasion. By co-administering *Plasmodium* polypeptides, PfRipr, PfRh5, PfCyrPa individually or as a mixture or or as a complex, combinations of antibodies are generated against PfRipr, PfRh5, PfCyrPa that effectively inhibit growth of *Plasmodium* blood stages within the host. In another embodiment, modified and truncated forms may also be modified to comprise expression, detection, purification or anchorage tags to facilitate their isolation, purification, detection or administration etc. Tags may individually perform several such as enhancing folding and stability and facilitating purification. Several tags are known in the art and all such forms may be tested and employed. Modified and truncated forms may also comprise linker sequences to aid, for example, in their presentation to the immune system.

Illustrative purification tags include N-terminal hexa-His tag, biotin, Fc and Strepll (SAWSHPQFEK).

Reference to a Pf polypeptide/protein means one or more of PfRipr, PfRh5, PfCyrPa and PfEBA175 polypeptides or antigens, and includes any allele of the protein or modified or truncated forms thereof which induce inhibitory antibodies in a subject. In one embodiment, a Pf polypeptide may be expressed as a monomer. In one embodiment, a Pf polypeptide may be expressed as a homodimer. In one embodiment, a Pf polypeptide may be expressed as a homotrimer.

Reference to a Pf polypeptide/protein means one or more of PfRipr, PfRh5, PfCyrPa and PfEBA175 polypeptides or antigens, and includes any allele of the protein or modified or truncated forms thereof which induce inhibitory antibodies in a subject. In one embodiment, a Pf polypeptide may be expressed as a monomer. In one embodiment, a Pf polypeptide may be expressed as a homodimer. In one embodiment, a Pf polypeptide may be expressed as a homotrimer.

Reference to a Pf protein complex, or Pf protein mixture means substantially a complex or substantially a mixture comprising two or more of PfRipr, PfRh5, PfCyrPa and PfEBA175 polypeptides or antigens, and includes any allele of the protein or modified or truncated forms thereof which induce inhibitory antibodies in a subject.

In one embodiment, the Pf protein may be glycosylated.

In one embodiment, the PfRipr is essentially full length, lacking its signal sequence. The PfRipr signal sequence (MKLCILLAVVAFVGLSLG) is cleaved and removed during secretion. In an embodiment, PfRipr is expressed as a soluble monomer, a soluble homodimer or a combination thereof.

Illustrative strains or genotypes from which the polypeptides or their sequences may be derived include 7G8, 3D7 (reference strain), DD2, HB3, W2MEF, D10, GHANA1, T994, CSL-2, EBB, MCAMP, PREICH, RO-33, V1_S, SANTALUCIA, SENEGAL3404, K1, FCR-3, FCC-2, and D6.

"Derived from" includes directly or indirectly derived from.

In an embodiment, PfRipr comprises the amino acid sequence set forth in SEQ ID NO: 6 or a sequence or at least 70%, or at least 75%, or at least 80%, or at least 85%, or at least 90%, or at least 95%, or at least 97%, or at least 98%, or at least 99% identical thereto, or a biologically or immunologically active fragment thereof.

In an embodiment, PfRh5 comprises the amino acid sequence set forth in SEQ ID NO: 8 or 9; or at least 70%, or at least 75%, or at least 80%, or at least 85%, or at least 90%, or at least 95%, or at least 97%, or at least 98%, or at least 99% identical to SEQ ID NO: 8 or 9; or a biologically or immunological active fragment thereof.

In an embodiment, PfCyrPa comprises the amino acid sequence set forth in SEQ ID NO: 7 or at least 70%, or at least 75%, or at least 80%, or at least 85%, or at least 90%, or at least 95%, or at least 97%, or at least 98%, or at least 99% identical thereto, or a biologically or immunologically active fragment thereof.

In an embodiment, PfEBA175 comprises the amino acid sequence set forth in SEQ ID NO: 10 or 27 or at least 70%, or at least 75%, or at least 80%, or at least 85%, or at least 90%, or at least 95%, or at least 97%, or at least 98%, or at least 99% identical thereto, or a biologically or immunologically active fragment thereof.

In one embodiment, the heterologous polynucleotide encoding a PfRipr polypeptide and a suitable signal sequence operably linked to a promoter which induces PfRipr polypeptide expression in the cell comprises the sequence set forth in SEQ ID NO: 14.

In another embodiment, the cell further comprises a heterologous polynucleotide encoding PfRh5 polypeptide and a suitable signal sequence operably linked to a promoter which induces polypeptide expression the cell. In an embodiment, the polynucleotide comprises the sequence set forth in SEQ ID NO: 15. In one embodiment, co-expression of PfRipr and PfRh5 polypeptides in a *Drosophila* culture cell induces increased yields of both polypeptides compared to mono-expression of either polypeptide in the same cells.

In one embodiment, the cell further comprises a heterologous polynucleotide encoding a PfCyrPa polypeptide and a suitable signal sequence operably linked to a promoter which induces high level of PfCyrPa polypeptide expression in the cell. In an embodiment, the polynucleotide comprises the sequence set forth in SEQ ID NO: 16.

In one embodiment PfEBA175 is expressed together with PfRipr, PfRh5, PfCyrPa in the expression host cell.

Thus in one embodiment, the cell of the present invention may express a PfRipr, a PfRh5, or a PfCyrPa polypeptide, individually, a PfRipr and a PfRh5 polypeptide together, a PfRh5 and a PfCyrPa polypeptide together, a PfRipr and a PfCyrPa polypeptide together, or a PfRipr and a PfRh5 and a PfCyrPa polypeptide together. Reference to "together" includes substantially as a complex and/or substantially as an uncomplexed mixture of protein.

In another embodiment, the expression host cell expresses a PfRipr, a PfRh5, a PfCyrPA or a PfEBA175 polypeptide individually, a PfRipr, a PfRh5 and a PfEBA175 polypeptide together, or a PfRh5, a PfCyrPa and a PfEBA175 polypeptide together, or a PfRipr, a PfCyrPa and a PfEBA175, or a PfRipr and a PfRh5 and a PfCyrPa polypeptide and a PfEBA175 polypeptide together.

In one embodiment, the heterologous polynucleotide or vector expressing the subject polypeptides encodes one or two or three or four heterologous polypeptides.

In one embodiment, A *Drosophila* derived cell modified to express a *Plasmodium falciparum* (Pf) Ripr polypeptide, a PfRh5 polypeptide and a PfCyrPa polypeptide from a heterologous polynucleotide encoding a PfRipr polypeptide and a suitable signal sequence operably linked to a promoter which induces high level of PfRipr polypeptide expression, a PfRh5 polypeptide and a suitable signal sequence operably linked to a promoter which induces high level of PfRh5 polypeptide expression and a PfCyrPa polypeptide and a suitable signal sequence operably linked to a promoter which induces high level of PfCyrPa polypeptide expression in a *Drosophila* derived cell wherein the PfRipr polypeptide, PfRh5 polypeptide and PfCyrPa polypeptide from said cell induces parasite invasion inhibitory antibodies when administered to a subject.

In one embodiment the cell further comprises a heterologous polynucleotide encoding a PfEBA175 polypeptide and a suitable signal sequence operably linked to a promoter which induces EBA175 polypeptide expression in the cell. In one embodiment amino acids 760-1298 of EBA175 allele derived from 3D7 strain are expressed (SEQ ID NO: 17). In one embodiment, amino acids 761-1271 of EBA175 allele derived from W2MEF are expressed (SEQ ID NO: 27).

Thus the cell of the present invention may express a PfRipr polypeptide and one or more of a PfRh5 polypeptide, a PfCyrPa polypeptide, and a PfEBA175 polypeptide. In one embodiment, the cell may express a PfRipr polypeptide and a PfRh5 polypeptide, or a PfRipr polypeptide and a PfCyrPa polypeptide, or a PfRipr polypeptide and a PfEBA175 polypeptide. In one embodiment, the cell may express a PfRipr polypeptide, a PfRh5 polypeptide and a PfCyrPa polypeptide.

In one embodiment PfRipr is expressed in a *Drosophila* cell. In one embodiment PfRh5 and/or PfCyraPa and/or PfEBA175 are expressed in an expression system other than a *Drosophila* cell. A wide range of expression systems are known in the art and some are described herein. Protein expression systems suitable for clinical biomanufacture include baculovirus expression systems and mammalian expression systems and prokaryotic expression systems.

In another aspect the description provides an expression vector comprising, a polynucleotide encoding a PfRipr polypeptide and a suitable signal sequence, said polynucleotide operably linked to a promoter which induces PfRipr polypeptide expression in a *Drosophila* continuous culture cell, wherein the PfRipr polypeptide from said cell induces parasite growth inhibitory antibodies when administered to a subject.

In another aspect the description provides an expression vector comprising, a polynucleotide encoding a PfRh5 polypeptide including a truncated form and a suitable signal sequence, said polynucleotide operably linked to a promoter which induces PfRh5 polypeptide expression in an expression host cell, wherein the PfRh5 polypeptide from said cell induces parasite growth inhibitory antibodies when administered to a subject.

In on embodiment, the PfRh5 polypeptide is a truncated from of PfRh5 polypeptide comprising amino acids D126 through to Q526 of full length PfRh5. In one embodiment the truncated form of PfRh5 is formed in S2 cell culture.

In another aspect the description provides an expression vector comprising, a polynucleotide encoding PfCyrPa polypeptide and a suitable signal sequence, said polynucleotide operably linked to a promoter which induces high level of PfCyrPa polypeptide expression in an expression host cell, wherein the PfCyrPa polypeptide from said cell induces parasite growth inhibitory antibodies when administered to a subject.

In one embodiment, the description provides an expression vector comprising, a polynucleotide encoding a PfEBA175 polypeptide and a suitable signal sequence, said polynucleotide operably linked to a promoter which induces PfEBA175 polypeptide expression in an expression host cell, wherein the PfEBA175 polypeptide from said cell induces parasite growth inhibitory antibodies when administered to a subject.

In one embodiment, the expression host cell and expression vector are compliant with current good manufacturing practices.

In another aspect the description provides an expression vector comprising, a polynucleotide encoding a PfRh5 polypeptide and a suitable signal sequence, said polynucleotide operably linked to a promoter which induces high level of PfRh5 polypeptide expression in a *Drosophila* continuous culture cell, wherein the PfRh5 polypeptide from said cell induces parasite growth inhibitory antibodies when administered to a subject, and wherein the polypeptide is a truncated from of PfRh5 polypeptide comprising amino acids D126 through to Q526 of full length PfRh5.

In another aspect the description provides an expression vector comprising, a polynucleotide encoding PfCyrPa polypeptide and a suitable signal sequence, said polynucleotide operably linked to a promoter which induces high level of PfCyrPa polypeptide expression in a *Drosophila* continuous culture cell, wherein the PfCyrPa polypeptide from said cell induces parasite growth inhibitory antibodies when administered to a subject.

In one embodiment, the description provides an expression vector comprising, a polynucleotide encoding a PfEBA175 polypeptide and a suitable signal sequence, said polynucleotide operably linked to a promoter which induces PfEBA175 polypeptide expression in a *Drosophila* continuous culture cell, wherein the PfEBA175 polypeptide from said cell induces parasite growth inhibitory antibodies when administered to a subject.

In one embodiment the polynucleotide encoding a PfEBA175 polypeptide and a suitable signal sequence operably linked to a promoter induces EBA175 polypeptide expression in a host cell. In an embodiment, the polynucleotide comprises the sequence set forth in SEQ ID NO: 17.

In one embodiment, amino acids 760-1298 of EBA175 allele derived from the 3D7 strain are encoded.

In one embodiment, amino acids 761-1271 of EBA175 allele derived from W2MEF are encoded.

In another aspect the description provides a *Drosophila* cell comprising one, two or three vectors selected from a vector as described herein. In an embodiment, the one, two or three vectors are stably transfected into the *Drosophila* cell. In an embodiment, the one, two or three vectors are transiently transfected into the *Drosophila* cell.

In another aspect the description provides a Pf polypeptide or Pf protein complex or Pf protein mixture purified from the cell as described herein.

In another aspect the description provides a purified Pf protein complex or mixture wherein the complex or mixture comprises PfRipr polypeptide, PfRh5 polypeptide comprising only amino acids D126 through to Q526 of full length PfRh5 (lacking amino acids 1 to 125), and PfCyrPa polypeptide, and wherein the purified Pf protein complex or mixture induces parasite invasion inhibitory antibodies when administered to a subject.

In another aspect the description provides an immunogenic composition comprising the purified Pf complex or mixture as described herein. Thus, in one embodiment, the immunogenic composition comprises a PfRipr polypeptide, a PfRh5 polypeptide, and a PfCyrPa polypeptide. In one embodiment, the PfRh5 polypeptide comprises only amino acids D126 through to Q526 of full length PfRh5 (lacking amino acids 1 to 125) or a modified form thereof. In one embodiment, the immunogenic composition further comprises a PfEBA175 polypeptide. In one embodiment, the EBA175 polypeptide comprises amino acids 760-1298 of EBA175 allele derived from the 3D7 strain. In one embodiment, the EBA175 polypeptide comprises amino acids 761-1271 of EBA175 allele derived from W2MEF.

In another aspect the description provides a Virus like particle (VLP) or virosome comprising the purified Pf protein or complex or mixture as described herein.

Thus in one embodiment, the description provides VLP or virosome comprising one or more of PfRipr polypeptide, a PfRh5 polypeptide, a PfCyrPa polypeptide, and a PfEBA175 polypeptide. In one embodiment, the VLP or virosome is assembled using a conjugation system to covalently attach the Pf protein to the surface of the VLP or virosome to form a medium or high density array of Pf polypeptide. VLP or virosome particles may be prepared using one, two, three or four Pf polypeptides, or complexes of two or three Pf polypeptides as described herein. Single Pf polypeptide VLPs or virosomes may then be combined to form substantially mixtures of Pf polypeptides as described herein.

Thus, in one embodiment, the VLP or virosome or mixture thereof comprises a PfRipr polypeptide, a PfRh5 polypeptide, and a PfCyrPa polypeptide. In one embodiment, the PfRh5 polypeptide comprises only amino acids D126 through to Q526 of full length PfRh5 (lacking amino acids 1 to 125) or a modified form thereof. In one embodiment, the VLP or virosome or substantially mixture thereof further comprises a PfEBA175 polypeptide. In one embodiment, the EBA175 polypeptide comprises amino acids 760-1298 of EBA175 allele derived from the 3D7 strain. In one embodiment, the EBA175 polypeptide comprises amino acids 761-1271 of EBA175 allele derived from W2MEF.

In one embodiment the description provides an immunogenic composition comprising the purified Pf protein or complex or mixture as described herein or the VLP or virosome as described herein, and a pharmaceutically acceptable carrier such as a diluent or excipient, or an adjuvant.

The term "carrier" applied to pharmaceutical compositions refers to a diluent, excipient, or vehicle with which the Pf protein mixture or complex is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like.

In one embodiment the description provides a method of producing a *Plasmodium falciparum* (Pf) Ripr polypeptide comprising transfecting a *Drosophila* derived cell with a vector of as described herein and isolating PfRipr from said cells. In one embodiment, the Pf polypeptides comprise one or more tags to facilitate isolation and purification.

In one embodiment the description provides a method of producing a *Plasmodium falciparum* (Pf) polypeptide mixture or complex comprising transfecting a population of *Drosophila* derived cells with one, two, three or four vectors of as described herein. In one embodiment, the method comprises culturing the cells to identify a stable cell line expressing one or more Pf polypeptides. In one embodiment, the method comprises culturing a *Drosophila* derived cell line comprising one or more vectors as described herein and isolating the Pf polypeptides or complex comprising same from cell culture media. In one embodiment, the Pf polypeptide/s comprise/s one or more tags to facilitate isolation and purification.

In one embodiment the description provides a method of producing an immune response in a subject, the method comprising a administering to the subject an effective amount of the immunogenic composition as described herein.

In one embodiment the description provides a method of treating and/or preventing malaria caused by *P. falciparum* in a subject, the method comprising administering to the subject an effective amount of the immunogenic composition as described herein.

In one embodiment the description provides an immunogenic composition comprising the Pf polypeptide or Pf protein complex or Pf protein mixture as described herein for use in the treatment and/or prophylaxis of *P. falciparum* malaria.

In one embodiment the description provides an immunogenic composition comprising the Pf polypeptide or Pf protein complex or Pf protein mixture as described herein for use in the manufacture of a preparation for the treatment or prophylaxis of *P. falciparum* malaria.

In another embodiment, the immunogenic composition further comprises a pharmaceutically or physiologically acceptable carrier or diluent.

In a further embodiment, the immunogenic composition further comprises an adjuvant. In one illustrative embodiment, the adjuvant is a saponin based adjuvant.

In one illustrative embodiment, the adjuvant is a Virus-like particle (VLP).

In a further embodiment the description provides a kit for detecting if a subject (a) has or had a *P. falciparum* malaria infection or (b) has been vaccinated against *P. falciparum* malaria, the kit comprising:

(i) a Pf polypeptide or Pf protein complex or Pf protein mixture as described herein capable of binding an anti-*P. falciparum* malaria antibody and forming and antigen-antibody complex, and (ii) one or more antigen-antibody complex detection reagents.

In a further embodiment the present description provides a method for producing a purified antibody against one or more of the herein described proteins produced in a *Drosophila* derived cell, comprising administering to a subject an immunologically effective amount of the protein, mixture or complex, and isolating and purifying the antibody produced.

In an embodiment the description provides an isolated antibody raised against the Pf polypeptide or Pf protein complex or Pf protein mixture as described herein.

In one embodiment, antibodies generated include those that at least partially neutralize an important part of the malaria life cycle such as host cell invasion or schizogony. In some embodiments, antibodies generated against the present Pf polypeptide mixture or complex, inhibit the formation of a complex between PfRipr, PfRh5, a PfCyrPa and thereby The present description also provides for use of the herein described proteins, mixtures or complex in, or in the manufacture of a diagnostic agent (such as an antibody or protein mixture) for, the diagnosis or monitoring of infection by *Plasmodium falciparum* or monitoring of an anti-malaria treatment protocol.

In other aspects, screening methods are provided employing the instant proteins, mixtures and complexes to identify binding molecules such as antibodies, antigen-binding fragments or molecules, ligands, peptides, organic or inorganic molecules.

In vitro expression of proteins PfRipr, PfRh5, a PfCyrPa which form a complex in vivo facilitates screening assays to identify and test binding agents or other molecules able to prevent the complex formation or subsequent erythrocyte cell invasion.

In another aspect, the present description provides a kit or a solid or semi-solid substrate comprising one or more of the herein described proteins, mixtures or complex. The kits or substrates of the present invention are contemplated for use in diagnostic, prognostic, therapeutic or prophylactic applications as well as for use in designing and/or screening *Plasmodium* binding molecules or *Plasmodium* receptor molecules. The kits and substrates are also useful in monitoring the efficacy of a treatment protocol against *Plasmodium falciparum*. In an embodiment the present description provides a kit for detecting if a subject has a *P. falciparum* infection, the kit comprising:

(i) an isolated antibody raised against the Pf polypeptide or Pf protein complex or Pf protein mixture as described herein capable of binding a *P. falciparum* malaria antigen, and (ii) one or more antigen-antibody complex detection reagents.

In an embodiment the present description provides a kit for monitoring treatment of a subject having a *P. falciparum* infection, the kit comprising:

(i) an isolated antibody raised against the Pf polypeptide or Pf protein complex or Pf protein mixture as described herein capable of binding a *P. falciparum* malaria antigen, and (ii) one or more antigen-antibody complex detection reagents.

In an embodiment the present description provides a kit as described herein, wherein the kit is for use in an immunoassay. In an embodiment the kit is an Enzyme Linked Immunosorbent Assay (ELISA)-type kit. In an embodiment the kit is an indirect ELISA type kit.

ELISA—type assays and kits are widely used in the art. In one illustrative embodiment kit comprise one or more detection reagents include/s a binding reagent which binds the antigen-antibody complex. In an embodiment the binding reagent is selected from: (i) protein G or a recombinant version thereof; (ii) protein A or a recombinant version thereof; (iii) isolated and/or recombinant protein A/G; (iv) protein L or a recombinant version thereof; or (v) an antibody or fragment thereof. In an embodiment the binding reagent is detectably labeled. In an embodiment the binding reagent is linked to an enzyme. In an embodiment the one or more detection reagents includes an enzyme substrate.

In an embodiment the present description provides a kit as described herein, wherein the Pf polypeptide, Pf protein complex, Pf protein mixture or isolated antibody raised against the Pf polypeptide, Pf protein complex or Pf protein mixture is conjugated to a solid support. In an embodiment the solid support is a microtitre well or part of a point of care device such as a microfluidic or immunographic device.

In an embodiment, the steps, features, integers, compositions and/or compounds disclosed herein or indicated in the specification of this application individually or collectively, and any and all combinations of two or more of said steps or features.

Any embodiment herein shall be taken to apply mutatis mutandis to any other embodiment unless specifically stated otherwise.

The above summary is not and should not be seen in any way as an exhaustive recitation of all embodiments of the present disclosure.

Many modifications will be apparent to those skilled in the art without departing from the scope of the present disclosure.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

BRIEF DESCRIPTION OF THE FIGURES

FIG. 3A to 3K shows the PfCyrPa, PfRipr PfRh5, PfEBA175 nucleotide and protein sequences and sequences of the pExpreS2-1, pExpreS2-2, pExpreS2-PAC expression vectors.

KEY TO SEQUENCE LISTING

SEQ ID NO: 1: PfRipr Full length (FL) nucleotide sequence;
SEQ ID NO: 2: PfCyrPa nucleotide sequence;
SEQ ID NO: 3: PfRh5 version 1 nucleotide sequence;
SEQ ID NO: 4: PfRh5 version 2 nucleotide sequence;
SEQ ID NO: 5: PfEBA175 nucleotide sequence;
SEQ ID NO: 6: PfRiprFL amino acid sequence;
SEQ ID NO: 7: PfCyrPa amino acid sequence;
SEQ ID NO: 8: PfRh5 Full length (FL) amino acid sequence;
SEQ ID NO: 9: PfRh5 version 1 amino acid sequence;
SEQ ID NO: 10: PfEBA175 amino acid sequence;

SEQ ID NO: 11: pExpreS2-1 vector nucleotide sequence;
SEQ ID NO: 12: pExpreS2-2 vector nucleotide sequence;
SEQ ID NO: 13: pExpreS2-PAC vector nucleotide sequence;
SEQ ID NO: 14: pExpreS2-1 vector comprising PfRiprFL;
SEQ ID NO: 15: pExpreS2-2 vector comprising PfRh5 version 1;
SEQ ID NO: 16: pExpreS2-PAC vector comprising PfCyrPa;
SEQ ID NO: 17: pExpreS2-1 vector comprising PfEBA175;
SEQ ID NO: 18: PfRh5 version 2 amino acid sequence;
SEQ ID NO: 19: His-tag nucleotide sequence;
SEQ ID NO: 20: StrepII purification tag nucleotide sequence;
SEQ ID NO: 21: N-terminal secretion signal nucleotide sequence;
SEQ ID NO: 22: Flag-tag nucleotide sequence;
SEQ ID NO: 23: His-tag amino acid sequence;
SEQ ID NO: 24: StrepII purification tag amino acid sequence;
SEQ ID NO: 25: N-terminal secretion signal amino acid sequence;
SEQ ID NO: 26: Flag-tag amino acid sequence;
SEQ ID NO: 27: PfEBA175 amino acid sequence (760-1271 W2MEF).

LIST OF TABLES

Figure 1:
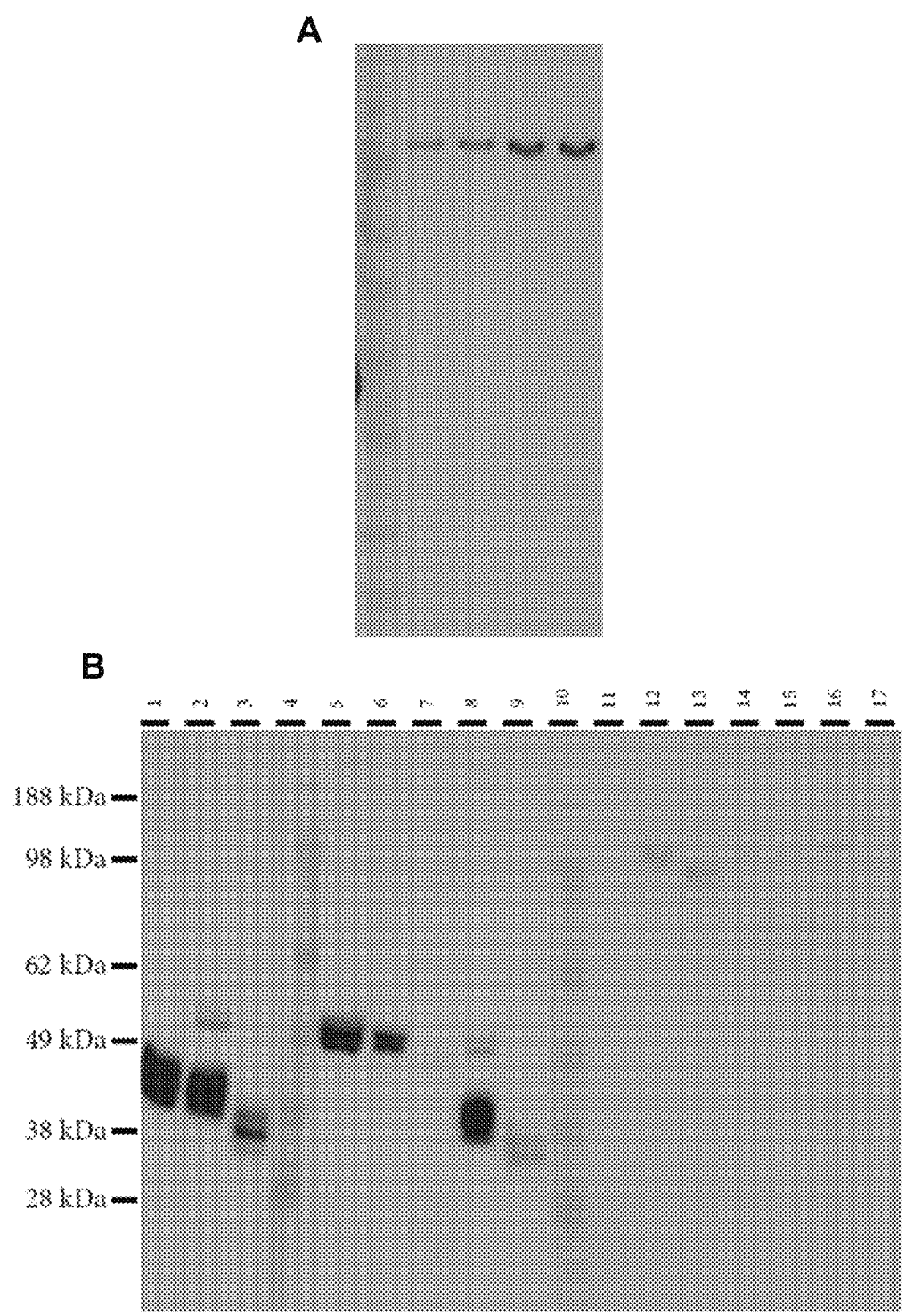
FIG. 1 show the analysis of gene expression from different vectors. (A) shows the comparison of PfRipr expression from a cell line comprising vectors expressing PfRiprFL only (lane 2 sample 1491, cell line WHTZ-04; lane 3 sample 1483, cell line WHTZ-04), PfRiprFL and PfRh5 (lane 4, sample 1320, cell line WHTZG-10), or PfRiprFL and PfRh5 and PfCypra (lane 5, sample 1482, cell line WHTZGP-13) compared to the See Blue Plus2 ladder (lane 1). (B) shows the comparison of expression of PfRiprFL and PfRh5 and PfCypra in cell lines expressing 1, 2 or 3 vectors. The samples run in each lane are listed in Table 3.
Figure 2:
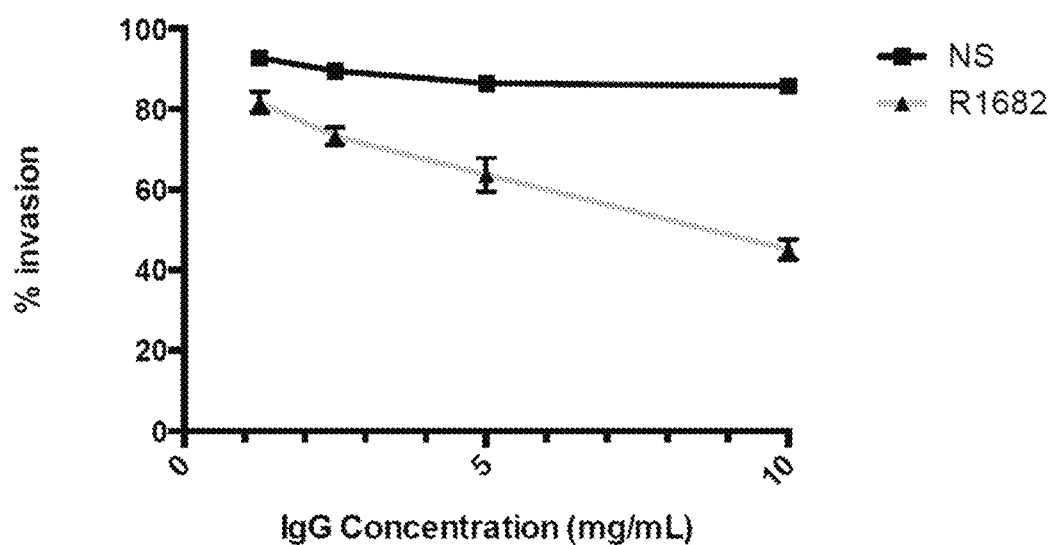
FIG. 2 shows that antibodies against full-length PfRipr inhibit the growth of *Plasmodium falciparum* parasites. *P. falciparum* 3D7 parasites were incubated with serially diluted purified IgG from either non-immune rabbit serum (NS) or anti-Ripr antiserum (R1682). The parasitaemia in triplicate wells was counted after 96 hours (2 invasion cycles) and error bars represent the standard deviation of the mean values in triplicate wells.

Table 1: Exemplary substitutions.
Table 2: Constructs present in each cell line.
Table 3: Lane order of gel from FIG. 2A.

DETAILED DISCUSSION OF EMBODIMENTS

The subject disclosure is not limited to particular screening procedures for agents, specific formulations of agents and various medical methodologies, as such may vary. Unless defined otherwise, all technical and scientific terms used herein have the same meanings as commonly understood by one of ordinary skill in the art to which this disclosure belongs. Any materials and methods similar or equivalent to those described herein can be used to practice or test the present disclosure. Practitioners are particularly directed to and Ausubel et al., Current Protocols in Molecular Biology, Supplement 47, John Wiley & Sons, New York, 1999; Colowick and Kaplan, eds., Methods In Enzymology, Academic Press, Inc.; Weir and Blackwell, eds., Handbook of Experimental Immunology, Vols. I-IV, Blackwell Scientific Publications, 1986; Remington's Pharmaceutical Sciences (18th ed., Mack Easton, Pa. (1990)), for definitions and terms of the art and other methods known to the person skilled in the art.

The term "and/or", e.g., "X and/or Y" shall be understood to mean either "X and Y" or "X or Y" and shall be taken to provide explicit support for both meanings or for either meaning.

As used herein "subjects" contemplated in the present description are humans or animals including laboratory or art-accepted test or vehicle animals. In an embodiment, the subject is a mammal. Preferably, the subject is a human, however the present description extends to treatment and/or prophylaxis of other mammalian patients including primates and laboratory test animals (e.g. mice, rabbits, rats, guinea pigs).

The terms "protein" and "polypeptide" are generally used interchangeably herein. A polypeptide may be defined by the extent of identity (% identity) of its amino acid sequence to a reference amino acid sequence, or by having a greater % identity to one reference amino acid sequence than to another. The % identity of a polypeptide to a reference amino acid sequence is typically determined by GAP analysis (Needleman and Wunsch, 1970; GCG program) with parameters of a gap creation penalty=5, and a gap extension penalty=0.3. In an embodiment, the query sequence is at least 50 amino acids in length and the GAP analysis aligns the two sequences over a region of at least 50 amino acids. In an embodiment, the query sequence is at least 100 amino acids in length and the GAP analysis aligns the two sequences over a region of at least 100 amino acids. In another embodiment, the query sequence is at least 150 amino acids in length and the GAP analysis aligns the two sequences over a region of at least 150 amino acids. Preferably, the GAP analysis aligns two sequences over their entire length. Preferably, the polypeptide has an antigenic activity of at least 10% of the activity of the reference polypeptide.

With regard to a defined polypeptide, it will be appreciated that % identity figures higher than those provided herein will encompass preferred embodiments. Thus, where applicable, in light of the minimum % identity figures, it is preferred that the polypeptide/protein comprises an amino acid sequence which is at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

As used herein, the term "Pf polypeptide" or "Pf protein" refers to a protein from *Plasmodium falciparum*, a protozoan parasite of the genus *Plasmodium* that causes malaria in humans.

As used herein, the term "Ripr" refers to the Rh5 interacting protein and "PfRipr" refers to the Rh5 interacting protein from *Plasmodium falciparum*. In an embodiment, the PfRipr protein is encoded by the nucleotide sequence set forth in SEQ ID NO: 1 or a nucleotide sequence that is at least 50%, or at least 60%, or at least 65%, or at least 70%, or at least 75%, or at least 80%, or at least 85%, or at least 90%, or at least 95%, or 100% identical to the nucleotide sequence set forth in SEQ ID NO: 1 or a biologically active fragment thereof. In an embodiment, PfRipr has an amino acid sequence that is at least 45%, or at least 50%, or at least 54%, or at least 60%, or at least 65%, or at least 70%, or at least 75%, or at least 80%, or at least 85%, or at least 90%, or at least 91%, or at least 92%, or at least 93%, or at least 94%, or at least 95%, or at least 96%, or at least 97%, or at least 98%, or at least 99% or 100% identical to the amino acid sequence set forth in SEQ ID NO: 6 or a biological active fragment thereof.

As used herein, the term "a Rh5 polypeptide" refers to reticulocyte-binding protein homolog 5 and "a PfRh5 polypeptide" refers to reticulocyte-binding protein homolog from *Plasmodium falciparum*. In an embodiment, the PfRh5 polypeptide is encoded by nucleotide sequence set forth in SEQ ID NO: 3 or 4 or a nucleotide sequence that is at least 50%, or at least 60%, or at least 65%, or at least 70%, or at least 75%, or at least 80%, or at least 85%, or at least 90%, or at least 95%, or 100% identical to the nucleotide sequence set forth in SEQ ID NO: 3 or 4 or a biologically active fragment thereof. In an embodiment, a PfRh5 polypeptide has an amino acid sequence that is at least 45%, or at least 50%, or at least 54%, or at least 60%, or at least 65%, or at least 70%, or at least 75%, or at least 80%, or at least 85%, or at least 90%, or at least 91%, or at least 92%, or at least 93%, or at least 94%, or at least 95%, or at least 96%, or at least 97%, or at least 98%, or at least 99% or 100% identical to the amino acid sequence set forth in SEQ ID NO: 8, 9 or 18 or a biological active fragment thereof. In an embodiment, the PfRh5 polypeptide comprising amino acids D126 through to Q526 of full length PfRh5 (SEQ ID NO: 18).

As used herein, the term "a CyrPa polypeptide" refers to the Plasmodium cysteine-rich protective antigen and "a PfCyrPa polypeptide" refers to the Plasmodium cysteine-rich protective antigen from Plasmodium falciparum. In an embodiment, the PfCyrPa polypeptide is encoded by the nucleotide sequence set forth in SEQ ID NO: 2 or a nucleotide sequence that is at least 50%, or at least 60%, or at least 65%, or at least 70%, or at least 75%, or at least 80%, or at least 85%, or at least 90%, or at least 95%, or 100% identical to the nucleotide sequence set forth in SEQ ID NO: 2 or a biologically active fragment thereof. In an embodiment, PfCyrPa has an amino acid sequence that is at least 45%, or at least 50%, or at least 54%, or at least 60%, or at least 65%, or at least 70%, or at least 75%, or at least 80%, or at least 85%, or at least 90%, or at least 91%, or at least 92%, or at least 93%, or at least 94%, or at least 95%, or at least 96%, or at least 97%, or at least 98%, or at least 99% or 100% identical to the sequence set forth in SEQ ID NO: 7 or a biological active fragment thereof.

As used herein, the term "a EBA175 polypeptide" refers to the Erythrocyte binding antigen-175 and PfEBA175" refers to the Plasmodium Erythrocyte binding antigen-175 from Plasmodium falciparum. In an embodiment, the PfEB175 protein is encoded by the nucleotide sequence set forth in SEQ ID NO: 5 or a nucleotide sequence that is at least 50%, or at least 60%, or at least 65%, or at least 70%, or at least 75%, or at least 80%, or at least 85%, or at least 90%, or at least 95%, or 100% identical to the nucleotide sequence set forth in SEQ ID NO: 5 or a biologically active fragment thereof. In an embodiment, PfEB175 has an amino acid sequence that is at least 45%, or at least 50%, or at least 54%, or at least 60%, or at least 65%, or at least 70%, or at least 75%, or at least 80%, or at least 85%, or at least 90%, or at least 91%, or at least 92%, or at least 93%, or at least 94%, or at least 95%, or at least 96%, or at least 97%, or at least 98%, or at least 99% or 100% identical the amino acid sequence set forth in SEQ ID NO: 10 or SEQ ID NO:11 or a biological active fragment thereof.

The biologically active fragment may have the same or similar activity as, or an enhanced activity/immunogenicity relative to a reference polypeptide.

The Pf proteins as described herein may comprise one or more mutations e.g. an amino acid substitution, deletion or insertion or may comprise a chemical analog not present in the naturally occurring protein. Chemical analogs contemplated include modification of side chains, incorporation of unnatural amino acids and/or their derivatives during synthesis and the use of linkers or cross-linkers or other methods to inter alia impose conformational constraints.

Amino acid sequence mutants of the polypeptides defined herein can be prepared by introducing appropriate nucleotide changes into a polynucleotide defined herein, or by in vitro synthesis of the desired polypeptide. Such mutants include for example, deletions, insertions, or substitutions of residues within the amino acid sequence. A combination of deletions, insertions and substitutions can be made to arrive at the final protein, provided that the final polypeptide product possesses the desired characteristics.

Mutant (altered) polypeptides can be prepared using any technique known in the art, for example, using directed evolution or rational design strategies.

In designing amino acid sequence mutants, the location of the mutation site and the nature of the mutation will depend on characteristic(s) to be modified. The sites for mutation can be modified individually or in series for example, by (1) substituting first with conservative amino acid choices and then with more radical selections depending upon the results achieved, (2) deleting the target residue, or (3) inserting other residues adjacent to the located site. Amino acid sequence deletions generally range from about 1 to 15 residues, more preferably about 1 to 10 residues and typically about 1 to 5 contiguous residues. Substitution mutants have at least one amino acid residue in the polypeptide removed and a different residue inserted in its place. Such conservative substitutions are shown in Table 1 under the heading of "exemplary substitutions".

TABLE 1

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

In one embodiment a mutant/variant polypeptide has only, or not more than, one or two or three or four conservative amino acid changes when compared to a naturally occurring polypeptide. Details of conservative amino acid changes are provided in Table 1. Mutants with desired activity may be engineered using standard procedures in the art such as by performing random mutagenesis, targeted mutagenesis, or saturation mutagenesis on known genes of interest, or by subjecting different genes to DNA shuffling.

Modified Pf polypeptides are tested for their ability to bind to, engender or compete for binding with invasion inhibitory or non-inhibitory antibodies (binding agents) that bind to Pf merozoites in vitro or in vivo. Such assays are commonly employed in the art.

In an embodiment the mutation may comprise the insertion of a "linker". The term "linker" is used herein to refer to a short, flexible, polypeptide sequence of one or more amino acid residues in length. In an embodiment, the mutation comprises removal of one or more amino acid residues in the polypeptide and replacement with one or more residues with a linker. In an embodiment, the linker permits disulfide bond linkages between cysteine residues leading to retention of the native or "wild-type" disulfide linkages, and in particular retention of the ability to bind to conformation dependent antibodies. Suitable linker sequences are discussed in review articles by George and Heringa, 2002, and Argos, 1990, and may consist of up to 20 amino acid residues such as Gly and Ser, and include, and comprise amino acids selected from the sequence group consisting of Gly, Ser, Ala, Thr and Arg, more particularly Gly- and Ser-Ser-Gly (GSSG). Suitable linkers include, by way of example, the sequences (Gly) 2-Ala-(Gly)2, (Gly)5 or (Gly)s (see Sabourin et al., 2007), (Gly)6, (Gly)7 or (Gly) lo, Gly-Ser-Gly-Ser-Gly (see Dipti et al., 2006), -21(Gly) 4 (see Gly-Ala-Gly, (Gly)2-Arg-(Gly) 2-Ser (see Bellamy-McIntyre et al., 2007), (Gly-Gly-Gly-Gly-Ser),=3~4 (see Arai et al., 2006), and Ser-(Gly) 2-Ser-Gly (see Bahrami et al., 2007). One linker may have the sequence Gly-(Ser)2-Gly disclosed herein. It will be understood that selection of suitable linker is a matter of routine experimentation for a person skilled in this field, and the modified polypeptide contemplated herein is not limited to the particular linker sequences disclosed herein.

As used herein, the term "Pf protein complex" refers to a complex comprising a PfRipr polypeptide, a PfCyrPa polypeptide and a PfRh5 polypeptide. The polypeptides co-localise microscopically and form a functional interacting complex during invasion in vivo and may be co-purified and migrate together in non-reducing SDS-PAGE.

In one embodiment, the complex or proteins are produced using the cells, expression vectors and methods as described herein. The Pf protein complex may comprise PfRipr and PfCyrPa. The Pf protein complex may comprise PfRipr and PfRh5. The Pf protein complex may comprise PfRipr, PfCyrPa and PfRh5. The Pf protein complex or mixture may comprise PfRipr, PfCyrPa and PfRh5. A mixture may include the three polypeptides in an uncomplexed arrangement or in a partially complexed arrangement.

Reference to "Co-expression" includes for example expression in a cell of two or more vectors per cell, and includes one vector expressing two or more *Plasmodium* polypeptides.

As used herein, the term "Pf protein mixture" refers to mixture comprising two or more Pf proteins wherein the two or more proteins are not present as a complex.

In one embodiment, the proteins are produced using the cells, expression vectors and methods as described herein. In one embodiment the Pf protein mixture or complex contains or consists essentially of PfRipr and PfCyrPa. In one embodiment, the Pf protein mixture or complex contains or consists essentially of PfRipr and PfRh5. In one embodiment the Pf protein mixture or complex contains or consists essentially of PfRipr, PfCyrPa and PfRh5.

The term "isolated" and "purified" isolated means material that is substantially or essentially free from other components that normally accompany it in its native state. For example, an "isolated nucleic acid molecule" refers to a nucleic acid or polynucleotide, isolated from the sequences which flank it in a naturally-occurring state, e.g., a DNA fragment which has been removed from the sequences that are normally adjacent to the fragment. In particular, an isolated Pf polypeptide, Pf protein complex or Pf protein mixture includes in vitro isolation and/or purification of a protein from its natural cellular environment, and from association with other components of the cell. Without limitation, an isolated nucleic acid, polynucleotide, peptide, or polypeptide can refer to a native sequence that is isolated by purification or to a sequence that is produced by recombinant or synthetic means. In an embodiment, the Pf polypeptides as described herein may be isolated or purified as a Pf protein complex. In an embodiment, the Pf polypeptides as described herein may be isolated individually or as a Pf protein mixture and subsequently folded into a Pf protein complex.

Polynucleotides

As used herein, the term "polynucleotide" or "nucleotide" refers to a polymeric form of nucleotides of any length, either deoxyribonucleotides or ribonucleotides, or analogs thereof. A "heterologous polynucleotide" of the invention may be of genomic, cDNA, semisynthetic, or synthetic origin, double-stranded or single-stranded and by virtue of its origin or manipulation: (1) is not associated with all or a portion of a polynucleotide with which it is associated in nature, (2) is linked to a polynucleotide other than that to which it is linked in nature, or (3) does not occur in nature. The following are non-limiting examples of polynucleotides: messenger RNA (mRNA), cDNA, recombinant polynucleotides, plasmids, vectors, isolated DNA of any sequence, isolated RNA of any sequence, chimeric DNA of any sequence.

As used herein, an "isolated polynucleotide" refers to a polynucleotide which has been separated from the polynucleotide sequences with which it is associated or linked in its native state, or a non-naturally occurring polynucleotide. As used herein, an "exogenous polynucleotide" or "heterologous polynucleotide" refers to a polynucleotide produced or originating outside a particular host organism or cell.

The heterologous polynucleotide described herein encoding Pf polypeptides comprise regulatory sequences and coding sequences that are derived from different sources, or regulatory sequences and coding sequences derived from the same source, but arranged in a manner different to that found in nature. Such sequences may include a promoter, nucleotides encoding a signal sequences or sequences comprising or encoding a tag to aid expression and/or purification. In one embodiment, the heterologous polynucleotide comprises a promoter which allows for a high level of polypeptide expression when in a cell. The heterologous polynucleotide may comprise an N-terminal secretion signal sequence. In an embodiment the N-terminal secretion signal comprises the amino acid sequence "MKLCIL-LAVVAFVGLSLG" (SEQ ID NO: 25). The heterologous polynucleotide may comprise or encode a tag to aid purification of the expressed polypeptide. In one embodiment the tag is a His-tag comprising the amino acid sequence "HHHHHH" (SEQ ID NO: 23). In an embodiment, the tag is a StrepII purification tag comprising the amino acid sequence "SAWSHPQFEK". In one embodiment the tag is a Flag-tag comprising the amino acid sequence "DYKDDDDK". In another embodiment, the heterologous polynucleotide may comprise a sequence which aids the formation of virus like particles. In an embodiment, the tag facilitates controlled assembly of one or more Pf proteins as described herein in desirable (such as immune-protective) proportions in a VLP.

Polynucleotides of the invention may possess, when compared to naturally occurring molecules, one or more mutations which are deletions, insertions, or substitutions of nucleotide residues. Polynucleotides which have mutations relative to a reference sequence can be either naturally occurring (that is to say, isolated from a natural source) or synthetic (for example, by performing site-directed mutagenesis or DNA shuffling on the nucleic acid as described above).

In an embodiment, the polynucleotide may be codon optimised to increase expression of the isolated and/or recombinant protein or antigenic fragment thereof in a particular host cell. For example, the polynucleotide may by codon optimised for expression in *Drosophila*. The term "codon optimised" refers to modification of the codon encoding a particular amino acid to increase the expression of a protein in a given host cell. In one embodiment, endogenous glycosylation sites are retained.

Expression Systems

The selection of a suitable host organism for expression purposes is determined by various factors which are well known in the art. Factors to be considered include, for example, compatibility with the selected vector, toxicity of the expression product, expression characteristics, immunogenicity of the expressed product, necessary biological safety precautions and costs.

In some instances it may be desirable to insert the heterologous polynucleotide into an expression vector. In an embodiment, the expression vector may be transferred into a cell and the cell used to produce a Pf protein, Pf protein complex, or Pf protein mixture as described herein.

As used herein, a "vector" or "expression vector" is a DNA or RNA vector that is capable of transforming a host cell and effecting expression of one or more polynucleotides. In one embodiment, the expression vector is also capable of replicating within the host cell. Expression vectors can be either prokaryotic or eukaryotic. Expression vectors include any vectors that function (i.e., direct gene expression) in host expression cells of the present invention. The vector may be, e.g., a plasmid, virus, artificial chromosome, or a bacteriophage. Such vectors include chromosomal, episomal and virus-derived vectors, e.g., vectors derived from bacterial plasmids, bacteriophages, and viruses, vectors derived from combinations thereof, such as those derived from plasmid and bacteriophage genetic elements, cosmids and phagemids. In an embodiment, the vector is suitable for expression of Pf protein, Pf protein complex, or Pf protein mixture in an Arthropoda host cell such as a *Drosophila* cell. In an embodiment, the vector is a DNA polynucleotide comprising a nucleotide sequence having promoter activity in a *Drosophila* derived cell. In an embodiment, the vector is a viral vector such as a baculovirus (such as for example, AcMNPV that infects Lepidopteran derived cells such as Sf- or Hi-5 cells) retrovirus, a lentivirus, an adenovirus, a herpes virus, a poxvirus or an adeno-associated viral vector. Viral infected cells have a finite life span due to lysis of infected cells. Non-lytic expression systems are also available where the expression vector is stably integrated into the insect genome. Here, expression and secretion does not require cell lysis, making purification straightforward. Expression may be induced or constitutive depending upon the expression control sequence employed. In an embodiment, the vector is pExpreS2-1, pExpreS2-2 pExpreS2-PAC (Expres2ion Biotecnologies, Denmark).

A person skilled in the art will appreciate that a Pf polypeptide, Pf protein complex or Pf protein mixture as described herein can be produced in cell culture by expression of a heterologous polynucleotide as described herein in a host cell. In an embodiment, the host cell is an Arthropoda cell. A person skilled in the art would appreciate that the Arthropoda cell can be any Arthropoda cell which can be cultured in vitro and in which Pf polypeptide, Pf protein complex or Pf protein mixture can be expressed. In one embodiment, the cells are from a "continuous cell line" or can be cultured in "continuous cell culture". As used herein, the term "continuous cell culture" refers to a culture comprising of a single cell type that can be serially propagated in cell culture for a limited number of cell divisions or indefinitely. The cells as described herein can be cultured in any cell culture medium that allows the expansion of the cells in vitro.

In one embodiment the Arthropoda cell is a *Drosophila* cell. Methods of culturing *Drosphila* cells, including large scale production using a bioreactor, are known in the art and are described for example in Swiech et al (2008). In one example, the cells are cultured in at least a 500 mL, a 1 L, a 1.5 L, a 2 L, a 2.5 L or a 3 L volume.

"Cells," "insect cells", "*Drosophila* derived cell" "host expression cells," "transformed host cells," and the like are terms that not only refer to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A person skilled in the art will appreciate that the Pf protein, Pf protein complex, or Pf protein mixture as described herein (which can include purified protein or a subunit thereof or a viral particle or subunit thereof comprising the isolated and/or recombinant protein or an antigenic fragment thereof) can be purified by any method known to a person skilled in the art, including, for example one or more of the following steps: centrifugation, microfiltration, antibody purification, depth filtration ultrafiltration, diafiltration, precipitation, bead chromatography (for example size exclusion chromatography, ion exchange chromatography or affinity chromatography), membrane adsorber (for example ion exchange chromatography or affinity chromatography). The Pf proteins as described herein may comprise a tag, such as a His-tag or Flag-tag, which aids purification of the isolated and/or recombinant protein or antigenic fragment thereof.

The present description enables a composition comprising a Pf polypeptide complex or mixture of polypeptides wherein the Pf polypeptide complex or mixture is substantially free of Pf molecules other than a soluble PfRipr polypeptide, a soluble PfCyrPa polypeptide and a soluble PfRh5 polypeptide.

As used herein the phrases "substantially free" refers to a composition comprising less than 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or less than 1% aggregated Pf polypeptide (by weight).

In one embodiment, the proportion of Pf non-monomeric forms is less than 15%, 14%, 13%, 12%, 11%, 10%, 9%, 8%, 7%, 6%, 5%, 4%, 3%, 2%, 1%, 0.5% or 0.1% by weight.

In a particular embodiment, the compositions are substantially free of aggregated Pf polypeptide having less than 1% or less than 0.1% aggregated Pf molecules.

In another embodiment, the present description enables a composition comprising a Pf polypeptide complex comprising or consisting of a PfRipr polypeptide, a PfCyrPa polypeptide and a PfRh5 polypeptide wherein the Pf polypeptide complex is substantially free or depleted of uncomplexed Pf molecules.

In another embodiment, the present description enables a composition comprising a Pf polypeptide complex comprising a PfRipr polypeptide and a PfCyrPa polypeptide, or a PfRipr polypeptide and a PfRh5 polypeptide, or a PfCyrPa and a PfRipr polypeptide, a wherein the composition further comprises a PfRipr polypeptide, a PfCyrPa polypeptide or a PfRh5 polypeptide in uncomplexed form.

As used herein the phrases "substantially free or depleted" refers to a composition comprising less than 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or less than 1% uncomplexed Pf polypeptide (by weight).

In one embodiment, the proportion of uncomplexed Pf polypeptide is less than 15%, 14%, 13%, 12%, 11%, 10%, 9%, 8%, 7%, 6%, 5%, 4%, 3%, 2%, 1%, 0.5% or 0.1% by weight.

In a particular embodiment, the immunogenic compositions are substantially free of uncomplexed Pf polypeptide having less than 1% or less than 0.1% uncomplexed Pf molecules.

In one embodiment reference to a "mixture of Pf polypeptides" includes a proportion of complex polypeptide such as a composition comprising from 0% to 80% complexed Pf polypeptide and more than 20% uncomplexed Pf polypeptide. In one embodiment reference to a "mixture of Pf polypeptides" includes a composition having more than 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% (by weight) of uncomplexed Pf polypeptide.

In a related aspect, the immunogenic composition or VLP is enriched for or comprises a Pf polypeptide complex comprising two or three of a PfRipr polypeptide, a PfCyrPa polypeptide and a PfRh5 polypeptide and includes preparations of the composition having more than 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% (by weight) of the Pf complex. In an embodiment, the composition or VLP further comprises up to 30% uncomplexed Pf polypeptide selected from one or more of a PfRipr polypeptide, a PfCyrPa polypeptide, PfRh5 polypeptide and an EBA175 polypeptide.

In another embodiment, the present description enables a composition comprising a Pf polypeptide complex comprising a PfRipr polypeptide, a PfCyrPa polypeptide and a PfRh5 polypeptide, wherein the Pf polypeptide complex is conjugated at high density to a virus like particle or virosome. In another embodiment individual polypeptides of the complex are displayed separately on the VLP. Illustrative VLPs are known in the art and includes those using conjugation systems such as the SpyTag/SpyCatcher system and variations thereof. In one illustrative embodiment one or more of the Pf polypeptides is genetically modified to comprise a c-terminal Spycatcher tag which is used to display the complex via covalent interaction with a Spytag attached to *Acinetobacter* phage AP205 VLPs modified to display at least one tag per VLP subunit.

In some embodiment, the mixture or complex or composition further comprises EBA175 as described herein.

The term "immunogenic composition", "vaccine" or "vaccine composition as used herein refers to a pharmaceutical composition comprising at least one immunologically active component that induces an immunological response in a subject and possibly but not necessarily one or more additional components that enhance the immunological activity of said active component (for example an adjuvant).

As used herein, the term "pharmaceutically acceptable carrier" includes any and all solids or solvents (such as phosphate buffered saline buffers, water, saline) dispersion media, coatings, antibacterial and antifungal agents, isotonic and absorption delaying agents, and the like, compatible with pharmaceutical administration. Supplementary active compounds can also be incorporated into the compositions. The use of such media and agents for pharmaceutically active substances is well known in the art. Immunogenic compositions are described in a number of sources that are well known and readily available to those skilled in the art, for example, Remington's Pharmaceutical Sciences (Martin E. W., Easton Pa., Mack Publishing Company, 19.sup.th ed., 1995).

An immunogenic composition is formulated to be compatible with its intended route of administration, e.g., local or systemic. Examples of routes of administration include parenteral, e.g., intravenous, intradermal, subcutaneous, oral, nasal, topical, transdermal, transmucosal, and rectal administration. Oral and nasal administration include administration via inhalation. Solutions or suspensions used for parenteral, intradermal, or subcutaneous application can include the following components: a sterile diluent, such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Immunogenic compositions suitable for injectable use include sterile aqueous solutions (where water soluble) or dispersions, non-aqueous solutions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. Isotonic agents, for example, sugars, polyalcohols such as manitol, sorbitol, sodium chloride can also be included in the composition. Prolonged absorption of the injectable compositions can be brought about by including in the composition an agent that delays absorption, such as aluminium monostearate or gelatine.

Oral compositions generally include an inert diluent or an edible carrier. For the purpose of oral therapeutic administration, the active compound can be incorporated with excipients and used in the form of tablets, troches, or capsules, e.g., gelatine capsules. The tablets, pills, capsules, troches and the like can contain any of the following ingredients, or compounds of a similar nature: a binder such as microcrystalline cellulose, gum tragacanth or gelatine; an excipient such as starch or lactose, a disintegrating agent such as alginic acid, PRIMOGEL, or corn starch; a lubricant such as magnesium stearate or sterotes; a glidant such as colloidal silicon dioxide; a sweetening agent such as sucrose or saccharin; or a flavouring agent such as peppermint, methyl salicylate, or orange flavouring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, drops, or suppositories. For transdermal administration, the active compound (e.g., polynucleotides of the description) are formulated into ointments, salves, gels, or creams, as generally known in the art.

The immunogenic compositions can also be prepared in the form of suppositories (e.g., with conventional suppository bases such as cocoa butter and other glycerides) or retention enemas for rectal delivery.

In one embodiment, the immunogenic composition further comprises an adjuvant. Subject responses to immunogens can be enhanced if administered as a mixture with one or more adjuvants. Immune adjuvants typically function in one or more of the following ways: (1) immunomodulation (2) enhanced presentation (3) CTL production (4) targeting; and/or (5) depot generation. Illustrative adjuvants include: particulate or non-particulate adjuvants, complete Freund's adjuvant (CFA), aluminum salts, emulsions, ISCOMS, LPS derivatives such as MPL and derivatives thereof such as 3D, mycobacterial derived proteins such as muramyl di- or tri-peptides, particular saponins from *Quillaja saponaria*, such as QS21 and ISCOPREP™ saponin, ISCOMATRIX™ adjuvant, and peptides, such as thymosin alpha 1 or a VLP. In some embodiments, a VLP includes proteins from one or more of the following: an influenza virus (e.g., a hemaglutinin (HA) or neuraminidase (NA) polyptide), Hepatitis B virus (e.g., a core or capsid polypeptide), Hepatitis E virus, measles virus, Sindbis virus, Rotavirus, Foot-and-Mouth Disease virus, Retrovirus, Norwalk virus, human papilloma virus, HIV, RNA-phages, Q-phage (e.g., a coat protein), GA-phage, fr-phage, AP205 phage, a Ty (e.g., retrotransposon Ty protein p1). See, e.g., WO03/024480, WO03/024481, WO08/061243, and WO07/098186. An extensive description of adjuvants can be found in Cox and Coulter, "Advances in Adjuvant Technology and Application", in Animal Parasite Control Utilizing Biotechnology, Chapter 4, Ed. Young, W. K., CRC Press 1992, and in Cox and Coulter, Vaccine 15(3): 248-256, 1997.

The description includes a method for prophylactic or therapeutic treatment of *Plasmodium* infection in a patient, which comprises administration to the patient of an effective amount of a composition as described herein. Reference herein to "treatment" is to be understood in its broadest context. Accordingly, the term "prophylactic treatment" includes treatment to protect the patient against infection or to reduce the likelihood of infection. Similarly, the term "therapeutic treatment" of infection does not necessarily imply that the patient is treated until total recovery from infection, and includes amelioration of the symptoms of infection as well as reducing the severity of, or eliminating, the infection.

The immunogenic composition as described herein is administered in an effective amount. An "effective amount" means an amount necessary at least partly to attain the desired response, or to delay the onset or inhibit progression or halt altogether, the onset or progression of the infection. The amount varies depending upon the health and physical condition of the individual to be treated, the racial background of the individual to be treated, the degree of protection desired, the formulation of the composition, the assessment of the medical situation, and other relevant factors. It is expected that the amount will fall in a relatively broad range that can be determined through routine trials. If necessary, the administration of an effective amount may be repeated one or several times. The actual amount administered will be determined both by the nature of the infection which is being treated and by the rate at which the active immunogen or composition as described herein is being administered.

With regard to "prophylactic treatment" which can include vaccination a subject may be administered with one or more doses to achieve an effective immune response.

In accordance with the present description, the composition as described herein is administered to a patient by a parenteral or non-parenteral routes of administration. Parenteral administration includes any route of administration that is not through the alimentary canal (that is, not enteral), including administration by injection, infusion and the like. Administration by injection includes, by way of example, into a vein (intravenous), an artery (intraarterial), a muscle (intramuscular) and under the skin (subcutaneous). The composition as described herein may also be administered in a depot or slow release formulation, for example, subcutaneously, intradermally or intramuscularly, in a dosage which is sufficient to obtain the desired pharmacological effect.

In accordance with the methods and uses as described herein, a subject may receive a therapeutically effective amount of the composition as described herein in one or more doses. A person skilled in the art will understand that the composition as described herein, in particular a vaccine composition may be administered to a subject more than once and can be administered on any appropriate schedule, e.g., from one or more times per day to one or more times per week; including once every 1 day, 2 days, 3 days, 4 days, 5 days, 6 days, 1 week, 10 days, 2 weeks, 3 weeks, 4 weeks, 5 weeks, 6 weeks, 7 weeks, 8 weeks, 2 months, 3 months, 6 months, or more, or any variation thereon. The skilled artisan will appreciate that certain factors may influence the dosage and timing required to effectively treat, prevent or ameliorate a condition in a subject, including but not limited to previous treatments, the general health and/or age of the subject, and other diseases present. The skilled person will further understand that the compositions as described herein may be administered with one or more other immunogens suitable for the methods and uses described herein.

Sustained-release preparations that may be prepared are particularly convenient for inducing immune responses. Examples of sustained-release preparations include semipermeable matrices of solid hydrophobic polymers containing the polypeptide, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers, and poly-D-(−)-3-hydroxybutyric acid. While polymers such as ethylene-vinyl acetate and lactic acid-glycolic acid enable release of molecules for over 100 days, certain hydrogels release proteins for shorter time periods. Liposomes may be used which are of the small (about 200-800 Angstroms) unilamellar type in which the lipid content is greater than about 30% cholesterol, the selected proportion being adjusted for the optimal therapy.

Stabilization of proteins may be achieved by modifying sulfhydryl residues, lyophilizing from acidic solutions, controlling moisture content, using appropriate additives, and developing specific polymer matrix compositions. The in vivo half-life of proteins may be extended using techniques known in the art, including, for example, by the attachment of other elements such as polyethyleneglycol (PEG) groups.

Prime-boost immunization strategies as disclosed in the art are contemplated. See for example International Publication No. WO/2003/047617. Thus, compositions may be in the form of a vaccine, priming or boosting agent.

The present description enables antibodies or antigen binding portions raised against the herein described Pf polypeptide or Pf protein complex or Pf protein mixture, and their derivatives, by routine protocols.

Immunoassay

A person skilled in the art will appreciate that a Pf protein, Pf protein complex, or Pf protein mixture as described herein or an isolated antibody raised against the Pf polypeptide or Pf protein complex or Pf protein mixture as described herein are suitable for use in an immunoassay. Exemplary immunoassay formats include immunoblot, Western blot, enzyme linked immunosorbent assay (ELISA), radioimmunoassay (RIA) and enzyme immunoassay and assays suitable for point of care such as microfluidic assays and immunochromatographic device formats.

In an embodiment an immunoassay as described herein may comprise immobilizing an antigen, for example a Pf protein, Pf protein complex, or Pf protein mixture as described herein, to a solid support e.g. a membrane or microtitre well. A sample from a subject is then brought into physical relation with the Pf protein, Pf protein complex, or Pf protein mixture, and anti-*P. falciparum* malaria antibody/antibodies in the sample are bound or 'captured' by Pf protein, Pf protein complex, or Pf protein mixture. Binding of an anti-*P. falciparum* malaria antibody/antibodies to the Pf protein, Pf protein complex, or Pf protein mixture results in an antigen-antibody complex. The antigen-antibody complex is then detected by one or more detection reagents.

In an alternate embodiment an immunoassay as described herein may comprise immobilizing an antibody, for example an isolated antibody raised against the Pf polypeptide or Pf protein complex or Pf protein mixture as described herein to a solid support. A sample from a subject is then brought into physical relation with the isolated antibodies and *P. falciparum* malaria antigens in the sample are bound or 'captured' by the isolated antibody forming an antigen-antibody complex. The antigen-antibody complex is then detected by one or more detection reagents.

In an embodiment, the immunoassay is an ELISA. A person skilled in the art will appreciate that the ELISA may be a colorimetric, chemiluminescent or fluorescent. Furthermore, a person skilled in the art will appreciate that the ELISA can be a direct or an indirect ELISA.

In a direct ELISA the antigen-antibody complex is bound (or detected) by a binding reagent that is detectably labelled. In an indirect ELISA the binding reagent may be conjugated to an enzyme which acts upon an enzyme substrate to produce a detectable signal. Alternatively, in an indirect ELISA the antigen-antibody complex is bound by a first binding reagent (e.g. a primary antibody), which is bound by a second binding reagent (e.g. a secondary antibody), wherein the second binding reagent is detectably labelled or is conjugated to an enzyme which acts upon an enzyme substrate to produce a detectable signal.

It will be appreciated by a person skilled in the art that detection reagents may include, but is not limited to, one or more of the following: a binding reagent, a binding reagent conjugated to a detectable label, a binding reagent conjugated to an enzyme, an enzyme substrate, a wash buffer, a blocking buffer, and a solution for stopping an enzymatic reaction.

As used herein the term "binding reagent" refers to any reagent that binds to the antigen-antibody complex as described herein. In an embodiment, the binding reagent is a native or isolated and/or recombinant protein of microbial origin that binds to mammalian immunoglobulin molecules. In an embodiment the binding reagent, may bind to an Fc region in the antigen-antibody complex. In an embodiment, the binding reagent may bind to a VL-kappa present in the antigen-antibody complex. In an embodiment, the binding reagent binds to IgG, IgM IgA, IgE and/or IgD immunoglobulins. In an embodiment, the binding reagent binds to IgG antibodies. In an embodiment, the binding reagent is protein G or a recombinant version thereof, protein A or a recombinant version thereof, isolated and/or recombinant protein A/G, protein L or a recombinant version thereof.

In an embodiment, the binding reagent is an antibody or an antigen binding fragment thereof. These include immunoglobulins, immunoglobulin fragments or non-immunoglobulin derived protein frameworks that exhibit antigen-binding activity. The term "antibody" as used herein includes monoclonal antibodies, bispecific antibodies, fusion diabodies, triabodies, heteroconjugate antibodies, chimeric antibodies including intact molecules as well as fragments thereof, and other antibody-like molecules. Antibodies include modifications in a variety of forms including, for example, but not limited to, domain antibodies including either the VH or VL domain, a dimer of the heavy chain variable region (VHH, as described for a camelid), a dimer of the light chain variable region (VLL), Fv fragments containing only the light (VL) and heavy chain (VH) variable regions which may be joined directly or through a linker, or Fd fragments containing the heavy chain variable region and the CH1 domain.

A scFv consisting of the variable regions of the heavy and light chains linked together to form a single-chain antibody (Bird et al., 1988; Huston et al., 1988) and oligomers of scFvs such as diabodies and triabodies are also encompassed by the term "antibody". Also encompassed are fragments of antibodies such as Fab, (Fab')2 and FabFc2 fragments which contain the variable regions and parts of the constant regions. Complementarity determining region (CDR)-grafted antibody fragments and oligomers of antibody fragments are also encompassed. The heavy and light chain components of an Fv may be derived from the same antibody or different antibodies thereby producing a chimeric Fv region. The antibody may be of animal (for example mouse, rabbit or rat) or may be chimeric (Morrison et al., 1984). The antibody may be produced by any method known in the art.

The antibodies may be Fv regions comprising a variable light (VL) and a variable heavy (VH) chain in which the light and heavy chains may be joined directly or through a linker. As used herein a linker refers to a molecule that is covalently linked to the light and heavy chain and provides enough spacing and flexibility between the two chains such that they are able to achieve a conformation in which they are capable of specifically binding the epitope to which they are directed. Protein linkers are particularly preferred as they may be expressed as an intrinsic component of the Ig portion of the fusion polypeptide.

In an embodiment, the binding reagent comprises a detectable label. In an embodiment, the binding reagent is conjugated to an enzyme. In an embodiment, the binding reagent is conjugated to a protein such as biotin or streptavidin so that it may interact with a detectable label or enzyme that is streptavidin or biotin conjugated.

In an embodiment, the detection reagent comprises an enzyme. In an embodiment, the enzyme, may be, but is not limited to being alkaline phosphatase (AP), a peroxidisae such as horseradish peroxidase enzyme (HRP), β-D-galactosidease. In an embodiment, the enzyme is HRP.

A person skilled in the art will appreciate that the enzyme substrate can be any enzyme substrate suitable for use with one of the aforementioned enzymes wherein when acted upon by an enzyme, a detectable signal is produced. A person skilled in the art will appreciate that the enzyme substrate may be, for example, a colorimetric substrate, chemiluminescent substrate or fluorescent substrate.

In an embodiment, the solid support may be, but is not limited to being a membrane or microtitre well. In an embodiment, the solid support may be polyethylene, polypropylene or glass. In an embodiment, the solid support is a microtitre well. In an embodiment, the microtitre well is the well of a 96-well or 384-well plate.

Kits

A person skilled in the art would appreciate that the a Pf protein, Pf protein complex, or Pf protein mixture as described herein may be packaged in a kit suitable for detecting the presence of a *P. falciparum* malaria infection or the presence or detecting vaccination against a *P. falciparum* malaria infection. A person skilled in the art would further appreciate that an isolated antibody raised against the Pf polypeptide or Pf protein complex or Pf protein mixture as described herein may be packaged in a kit suitable for detecting if a subject has a *P. falciparum* infection. Such kits may contain one or more immunoassays suitable for detecting a positive or negative marker.

In an embodiment, the kit is for use in an immunoassay. In an embodiment, the kit is an Enzyme Linked Immunosorbent Assay (ELISA) kit. In an embodiment, the kit is an indirect ELISA kit. In an embodiment, the one or more detection reagents of the kit at least includes a binding reagent which binds the antigen-antibody complex. In an embodiment, the kit as described herein is suitable for high-throughput screening. The term "high-throughput screening" refers to screening methods that can be used to test or assess more than one sample at a time and that can reduce the time for testing multiple samples.

The following methods are used in practising the present description.

Vectors.

The PfRiprFL (SEQ ID NO: 1) and PfEBA175 (SEQ ID NO: 5) nucleotide sequences were inserted into the pExpreS2-1 expression vector (ExpreS$^2$ion Biotechnologies, Denmark; SEQ ID NO: 11) which has a marker allowing for Zeocin selection. The PfRh5 sequence (SEQ ID NO: 4) was inserted in to the pExpreS2-2 expression vector (ExpreS$^2$ion Biotechnologies, Denmark; SEQ ID NO: 12) which has a marker allowing for G418 selection and the PfCyrPa sequence (SEQ ID NO: 2) was inserted into the pExpreS2-PAC expression vector (ExpreS$^2$ion Biotechnologies, Denmark; SEQ ID NO: 13) which has a marker allowing for Puromycin selection.

Cell Transfection.

The above vectors comprising PfRiprFL, PfEBA175, PfRh5 or PfCyrPa were transfected into *Drosophila melanogaster* ExpreS$^2$ S2 cells (ExpreS$^2$ion Biotechnologies, Denmark). On the day before transfection ExpreS$^2$ S2 cells were split by centrifugation and resuspended in Excell420 Serum-Free Medium for Insect Cells (Sigma Aldrich; 14420C) at a density of $8 \times 10^6$ cells/ml and incubated at 25° C. at 115 rpm. On the day of transfection the cells were split by centrifugation and resuspended in Excell420 medium at a concentration of $2 \times 10^6$ cells/mL. A volume of 5 mL of the cell suspension was transferred to a T25 T-flask (CELLSTAR; GR-690160) and 50 µl ExpreS$^2$ Insect-TR 5× (ExpreS2ion Biotechnologies, Denmark) was added to the cell suspension followed by 12.5 µg DNA of the above vectors comprising PfRiprFL, EBA175, PfRh5 or PfCyrPa and mixed. The cells were then incubated for 3 hours at 25° C. before 1 mL of FBS was added. The day after transfection selection was added at the following concentrations: Zeocin 2000 µg/mL; G418 4000 µg/mL; and Puromycin 100 µg/mL.

For the next two weeks the T-flask was counted every 3-4 day and the cells were diluted to $1 \times 10^6$ cells/ml by adding the appropriate amount of fresh Excell420 medium comprising 10% FBS and selection to a final volume of 6 mL. After two weeks the cell suspension was transferred to a T75 flask (CELLSTAR; GR-658170) and 4 mL of Excell420 comprising 10% FBS and selection added. After 4 days, an additional 5 mL of media with selection was added. The cells were then transferred to a 125 mL shake flask (Sigma-Aldrich; CLS431143) after the cells had recovered and 10 ml of Excell420 added. After 4 days, the cells were split by centrifugation and resuspended in 50 ml Excell420 at a density of $8 \times 10^6$ cells/ml in a 250 ml shake flask (Signma-Aldrich; CLS431144). The cells were subsequently frozen in CryoStor® CS10 (Sigma; C2874-100ML) for later use.

The cell lines for co-expression was created by retransfecting a cell line already comprising a vector expressing one of the proteins PfRiprFL, PfEBA175, PfRh5 or PfCyrPa as described above with a second vector. The retransfection was the same as the initial transfection protocol. In this manor Rh5 was transfected into the cell line expressing PfRiprFL. A triple expressing cell line was created by transfecting PfCyrPa in the PfRiprFL, and PfRh5 expressing cell line.

Production of PfRipr in WAVE Bioreactor.

The production of PfRipr was performed by expanding the S2 cell line in shake flasks to a final volume of 1200 mL in Excell420 media (Sigma Aldrich; 14420C) in a 5 l shake flask (Thomson Instrument Company; 931116). The disposable WAVE Bioreactor system (GE Healthcare; WAVE Base 20/50) was used for the final production. The bag (GE Healthcare; CB0050L10-01) was inoculated to a density of $8 \times 10^6$ cells/mL with a volume of 5000 mL Excell420 at 25° C. The system parameters were set to 20 rpm, 8° angle, and 0.85 l/min of atmospheric air. After three days, an additional 20 mL of Excell420 was added to the bag and the parameters adjusted to 26 rpm, 9° angle, and 1.50 l/min of atmospheric air for 3 days. The contents of the bag were harvested by centrifugation and subsequently sterile filtered using 0.22 um filters.

Immunization Protocol for Raising Antibodies Against the PfRIPR/PfRh5/PfCyrPa complex.

Antigens were prepared for immunization by mixing the three individual proteins (PfRIPR/P/Rh5/PfCyrPa) expressed separately in equal molar ratio (1.1.1) based on quantitation of the individual proteins by UV spectroscopy. For each immunization the total antigen quantity of the combined proteins was 100 µg. Since the molecular weight of Ripr is roughly twice that of PfRh5 and PfCyrPa to ensure 100 µg of assembled complex 55 µg of each of PfRh5 and PfCyrPa was added to 125 µg of PfRipr. All proteins are in PBS pH 7.4. Previous analyses showed that complex formation occurs immediately and with high affinity (data not shown). Alternatively, a complex or mixture of proteins isolated from a cell expressing PfRIPR, PfRh5 and PfCyrPa may be used for immunizations. The protein mixture was then mixed with Freund's adjuvant (FA) before injection into a rabbit. A three dose schedule was followed with one immunization in complete FA followed at 28-day intervals with two immunization in incomplete FA.

Analysis of Antibodies Raised Against the PfRIPR/PfRh5/PfCyrPa Complex.

Serum was obtained from blood taken two weeks after the third immunization in the immunization schedule and IgG prepared by protein A sepharose chromatography.

The following non-limiting examples are provided.

Example 1: Comparison of PfRipr Expression; PfRipr Synergistic Effect

Samples were taken from the three cell lines at day three of culture and analyzed by western blot to compare PfRipr expression as shown in FIG. 1A. The lane order is as follows: lane 1, SeeBlue Plus2 ladder (Life Technologies); lane 2, sample 1491, cell line WHTZ-04 expressing PfRiprFL only; lane 3, sample 1483, cell line WHTZ-04 expressing PfRiprFL only; lane 4, sample 1320, cell line WHTZG-10 expressing PfRiprFL and PfRh5; lane 5, sample 1482, cell line WHTZGP-13 expressing PfRiprFL and PfRh5 and PfCyrPa. The samples from each cell line were prepared by mixing with buffer and reducing agent and incubation at 95° C. for five minutes. The gel was loaded and run for 35 minutes at 165V and blotted with an iBlott (Life Technologies). The membrane was blotted with anti-Strep (QIAGEN; 34850) and anti-mouse-HRP (DAKO; P0447) as secondary antibody for detection of PfRipr. The blot was then detected by enhanced chemiluminescence. The two samples of WHTZ-04 (from two different productions) show similar expression level. Both WHTZG-10 and WHTZGP-13 show similar expression level and an increased level compared to WHTZ-04. Co-expression of PfRh5 appears to increase the expression of PfRipr. The addition of PfCyrPa does not seem to further increase the expression of PfRipr.

Example 2: Vector Expression Analysis

Vectors comprising PfRiprFL, PfRh5, PfCyrPa as outlined above in the Vectors section were transfected separately and in combination with each other in ExpreS2 S2 cells. Each established cell line with their respective expression constructs are listed in the Table 2. The theoretical size of the PfRiprFL, PfRh5, PfCyrPa proteins is 126.67 kDa, 53.80 kDa, and 40.18 kDa, respectively.

The samples from each cell line were prepared by mixing with buffer and reducing agent and incubation at 95° C. for five minutes. Reducing agent was omitted in the lanes noted as un-reduced. The samples were loaded in the order listed below in Table 3. The gel was run for 35 minutes at 165V and blotted with an iBlotter. The membrane was blotted with anti-His or anti-Strep and anti-mouse-HRP as secondary antibody. The blot was then detected by enhanced chemiluminescence and imaged. Results are shown in FIG. 1B.

TABLE 2

| Cell line | Constructs |
|---|---|
| WHTZ-04 | pExpreS2-1 vector comprising PfRiprFL |
| WHTG-09 | pExpreS2-2 vector comprising PfRh5 |

TABLE 2-continued

| Cell line | Constructs |
|---|---|
| WHTP-12 | pExpreS2-PAC vector comprising PfCyrPa |
| WHTZG-10 | pExpreS2-1 vector comprising PfRiprFL and pExpreS2-2 vector comprising PfRh5 |
| WHTZGP-13 | pExpreS2-1 vector comprising PfRiprFL, pExpreS2-2 vector comprising PfRh5 and pExpreS2-PAC vector comprising PfCyrPa |

TABLE 3

| Lane | Sample | Comment | Cell line | Construct | Tag |
|---|---|---|---|---|---|
| 1 | TJ1438 | | WHTP-12 | PfCyrPa | |
| 2 | TJ1463 | | WHTZGP-13 | PfRiprFL, PfRh5, PfCyrPa | |
| 3 | TJ1463 | Un-reduced | WHTZGP-13 | PfRiprFL, PfRh5, PfCyrPa | |
| 4 | | Seeblue Plus2 | | | |
| 5 | TJ1322 | | WHTG-09 | PfRh5 | His |
| 6 | TJ1320 | | WHTZG-10 | PfRiprFL, PfRh5 | |
| 7 | TJ1320 | Un-reduced | WHTZG-10 | PfRiprFL, PfRh5 | |
| 8 | TJ1463 | | WHTZGP-13 | PfRiprFL, PfRh5, PfCyrPa | |
| 9 | TJ1463 | Un-reduced | WHTZGP-13 | PfRiprFL, PfRh5, PfCyrPa | |
| 10 | | Seeblue Plus2 | | | |
| 11 | TJ1343 | | WHTZ-04 | PfRiprFL | |
| 12 | TJ1463 | | WHTZGP-13 | PfRiprFL, PfRh5, PfCyrPa | |
| 13 | TJ1463 | Un-reduced | WHTZGP-13 | PfRiprFL, PfRh5, PfCyrPa | Strep |
| 14 | TJ1483 | Control | WHTZ-04 | PfRiprFL | |
| 15 | TJ1484 | Additive 1 | WHTZ-04 | PfRiprFL | |
| 16 | TJ1485 | Additive 2 | WHTZ-04 | PfRiprFL | |
| 17 | | Empty | | | |

Lane 1, 5, and 11 of FIG. 1B shows PfCyrPa, PfRh5 and PfRiprFL expressed individually from vectors. The observed size of the proteins corresponds to the theoretical size outlined above. The co-expression of PfRipr and PfRh5 (Lane 6 and 7) also shows expression. The reduced samples in lane 6 shows a clear band of WRh5. For the un-reduced sample (Lane 7), the band of PfRh5 is still visible though not as bright as the reduced sample. The high molecular weight bands is a normal background we see for our cells in His-tag western blots.

The triple-expression of PfRipr, PfRh5, and PfCyrPa (Lane 2, 3, 8, 9, 12, and 13) is also positive for all three constructs. The His-tag shows a positive band for both Rh5 and PfCyrPa in the reduced samples (Lane 2 and 8) while only, what is presumably PfCyrPa, one band is visible in the un-reduced samples (Lane 3 and 9). The band appears as a triplet and is slightly smaller compared to the reduced sample.

The Strep-tag shows a clear band in both the reduced and un-reduced samples. The un-reduced sample appears to be slightly smaller compared to the reduced sample.

Two additives were evaluated to determine if the expression level of PfRipr could be improved. No obvious difference in intensity is observed for the three samples (Lane 14 through 16).

All three constructs are expressed individually and confirmed by western blot and the observed size of each construct correspond to the theoretical size. The co-transfection of PfRipr and PfRh5 was successfully performed and stable cell line expressing both constructs was created.

The triple-expression of PfRipr, PfRh5, and PfCyrPa was successful and the cell line expresses all three constructs. The two additives tested did not have any obvious effect on the yield of PfRipr.

Example 3: Antibodies Against Full-Length Ripr Inhibit the Growth of Plasmodium falciparum Parasites Anti-Ripr antibodies were raised by immunizing a rabbit three times with 100 ug purified Ripr_FL protein in Freund's complete/incomplete adjuvant at day 0, 28 and 56. Serum was obtained from blood taken two weeks after the third immunization and IgG prepared by protein A sepharose chromatography.

To assess if antibodies raised against full-length Ripr inhibit the growth of *P. falciparum, P. falciparum* 3D7 parasites were incubated with serially diluted purified IgG from either non-immune rabbit serum (NS) or anti-Ripr antiserum (R1682). The parasitaemia in triplicate wells was counted after 96 hours (2 invasion cycles). In the presence of anti-Ripr IgG, merozoite invasion of erythrocytes was inhibited by 55% compared with non-immune rabbit IgG (FIG. 2).

The growth inhibition single cycle assay was performed according to methods described in Malkin et al. 2005.

REFERENCES

Argos J, 1990, Mol Biol 20; 211(4):943-58.
Bahrami et al., 2007, Virol 5; 363(2):303-9.
Bird et al., 1988, Science 242:423-426.
George and Heringa, 2002, Protein Eng 15(11):871-9.
Huston et al., 1988, Proc Natl Acad Sci USA 85:5879-5883.
Malkin et al., 2005, Infect Immun 73: 3677-3685.
Morrison et al., 1984, Proc Natl Acad Sci USA 81:6851-6855.
Sabourin et al., 2007, Yeast 24(1):39-45).
Swiech et al., 2008, Cytotechnology 57:61-66.

The invention claimed is:

1. An expression vector comprising a polynucleotide encoding PfRipr polypeptide and a suitable signal sequence, said polynucleotide operably linked to an expression control sequence which induces the PfRipr polypeptide expression in a *Drosophila* derived cell wherein the polynucleotide comprises SEQ ID NO:14, wherein the PfRipr polypeptide from said cell induces parasite growth inhibitory antibodies when administered to a subject.

2. A *Drosophila* cell comprising the expression vector of claim 1.

3. An immunogenic composition comprising the vector of claim 1 and a physiologically or pharmaceutically acceptable carrier, diluent or excipient.

4. The immunogenic composition of claim 3 further comprising an adjuvant.

5. A method of producing *Plasmodium falciparum* (Pf) Ripr polypeptide comprising transfecting a *Drosophila* cell with a vector of claim 1 and isolating PfRipr from said cells.

* * * * *